(12) United States Patent
Achmüller et al.

(10) Patent No.: US 11,851,666 B2
(45) Date of Patent: Dec. 26, 2023

(54) MULTI-COPY GENE PROTEIN EXPRESSION SYSTEM

(71) Applicant: Novartis AG, Basel (CH)

(72) Inventors: Clemens Achmüller, Kundl (AT); Norbert Lamping, Holzkirchen (DE); Matjaz Vogelsang, Ljubljana (SI)

(73) Assignee: NOVARTIS AG

( * ) Notice: Subject to any disclaimer, the term of this patent is extended or adjusted under 35 U.S.C. 154(b) by 31 days.

(21) Appl. No.: 16/640,776

(22) PCT Filed: Aug. 22, 2018

(86) PCT No.: PCT/EP2018/072687
§ 371 (c)(1),
(2) Date: Feb. 21, 2020

(87) PCT Pub. No.: WO2019/038338
PCT Pub. Date: Feb. 28, 2019

(65) Prior Publication Data
US 2022/0025387 A1    Jan. 27, 2022

(30) Foreign Application Priority Data
Aug. 23, 2017 (EP) .................................. 17187552

(51) Int. Cl.
| | | |
|---|---|---|
| C12N 15/08 | (2006.01) | |
| C12N 15/85 | (2006.01) | |
| C07K 14/705 | (2006.01) | |
| C07K 16/00 | (2006.01) | |
| C12P 21/02 | (2006.01) | |
| C12N 15/81 | (2006.01) | |

(52) U.S. Cl.
CPC ...... C12N 15/815 (2013.01); C07K 14/70578 (2013.01); C07K 16/00 (2013.01); C12N 15/85 (2013.01); C12P 21/02 (2013.01); C07K 2317/622 (2013.01); C07K 2319/30 (2013.01)

(58) Field of Classification Search
CPC ........ C12N 15/10; C12N 15/12; C12N 15/17; C12N 15/62; C12P 21/02
See application file for complete search history.

(56) References Cited

U.S. PATENT DOCUMENTS

2010/0120623 A1    5/2010    Jorgensen

FOREIGN PATENT DOCUMENTS

| WO | 2003018771 A2 | 3/2003 |
|---|---|---|
| WO | 2004033693 A1 | 4/2004 |
| WO | 2008077881 A1 | 7/2008 |
| WO | 2014088693 A1 | 6/2014 |
| WO | 2016005931 A1 | 1/2016 |
| WO | 2016139279 A1 | 9/2016 |
| WO | 2016073794 A1 | 5/2017 |

OTHER PUBLICATIONS

Kudla et al. 2009; Codon-sequence determinants of gene expression in Escherichia coli. Science 324; 255-258 plus Supporting Online Material pp. 1-21.*
Mitra et al. 2016; Synonymous codons influencing gene expression in organisms, Research and Reports in Biochemistry. 2016:6 pp. 57-65.*
Altschul, Stpehen F., et al., Nucleic Acids Research, 1997, vol. 25, No. 17, pp. 3389-3402.
Brachmann, Carrie Baker, et. al., Yeast, 1998, vol. 14, pp. 115-132.
Ho, Steven C.L., et al, PLOS, 2013, vol. 8, Issue 5.
Kudla, Grzegorz, et al, Science, 2009, vol. 324, pp. 255-258.
Kueberl, Andreas, et al., Journal of Biotechnology, 2011, No. 154, pp. 312-320.
Lee, Jung-Lim, et al., Journal of Microbiology and Technology, vol. 18, No. 5, 2008, pp. 926-932.
Sturmberger, Lukas, et al., Journal of Biotechnology., 2016, No. 235, pp. 121-131.
International Search Report and Written Opinion for PCT/EP2018/072687, 15 pages.

* cited by examiner

*Primary Examiner* — Marsha Tsay
(74) *Attorney, Agent, or Firm* — Luedeka Neely, P.C.

(57) ABSTRACT

The present invention belongs to the field of biotechnology, specifically to the field of recombinant protein expression. The present invention focuses on two problems commonly encountered during recombinant protein expression, low quantity of protein expression and genetic instability of cell lines used for recombinant protein expression. The basic principle of the present invention is to introduce several expression cassettes into a cell which expression cassettes all code for the same mature recombinant protein of interest, but which expression cassettes have different nucleotide sequences. Expression cassette means a polynucleotide sequence which comprises at least a promoter sequence, a start codon, a polynucleotide sequence coding for a protein which is intended to be recombinant expressed (POI), a stop codon and a terminator.

13 Claims, 27 Drawing Sheets
Specification includes a Sequence Listing.

Figure 1: Vector used for expression in yeast cells
Figure 1A: yeast vector Y391_1xGOI with one GOI (scFv):
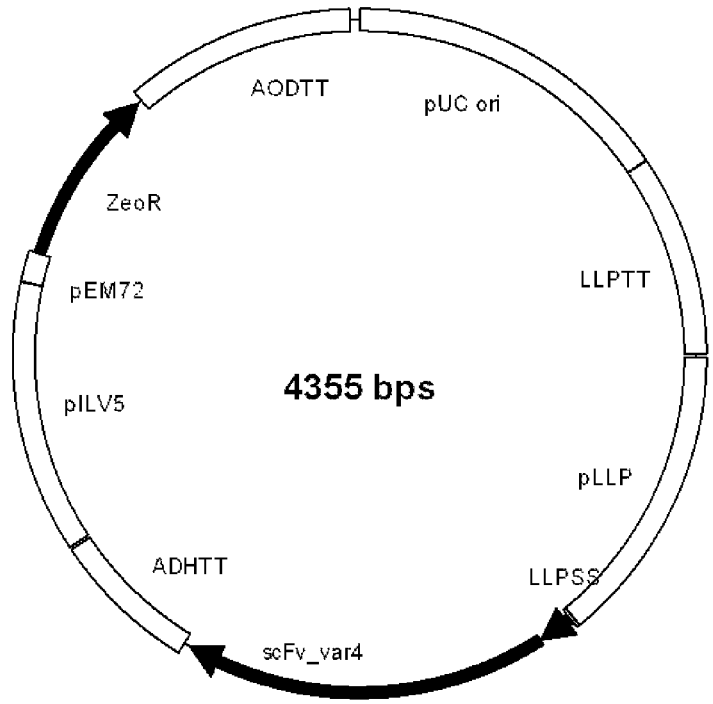
Figure 1B: yeast vector Y393_2xGOI with two GOI (scFv_var1, scFv_var2)
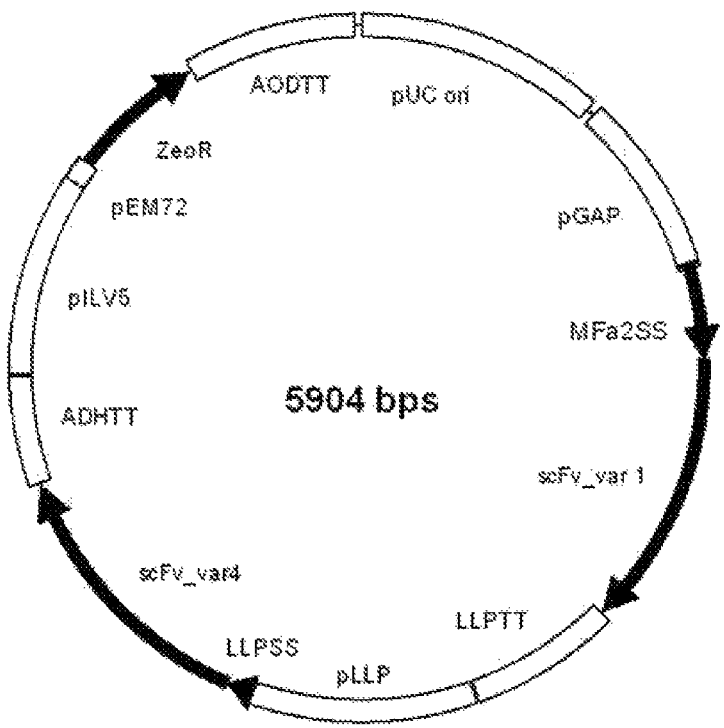

Figure 1C: yeast vector Y394_3xGOI with 3 GOI (scFv_var1, scFv_var2, scFv_var3):
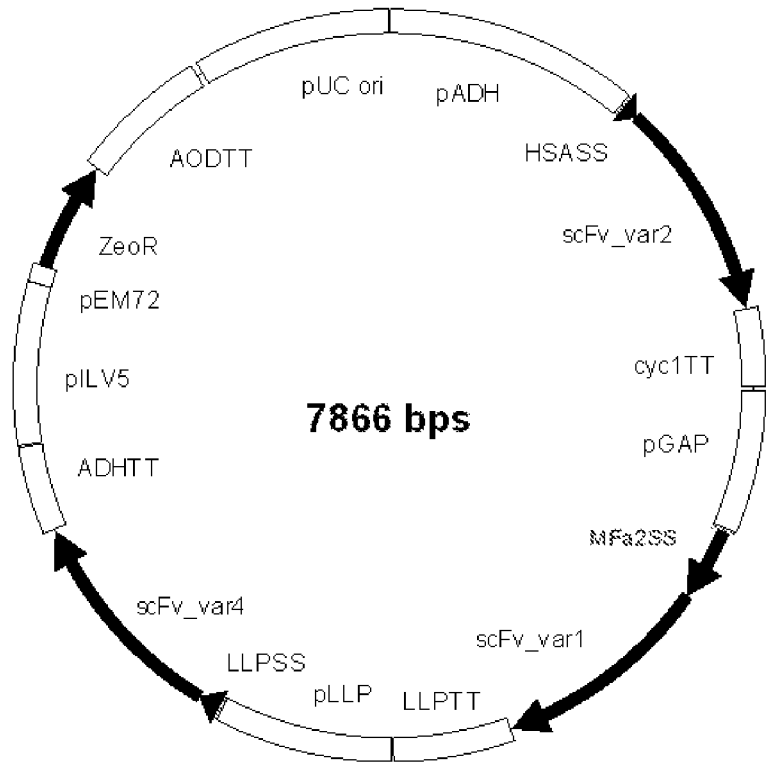
Figure 1D: yeast vector Y395_4xGOI with 4 GOI (scFv_var1, scFv_var2, scFv_var3, scFv_var4)
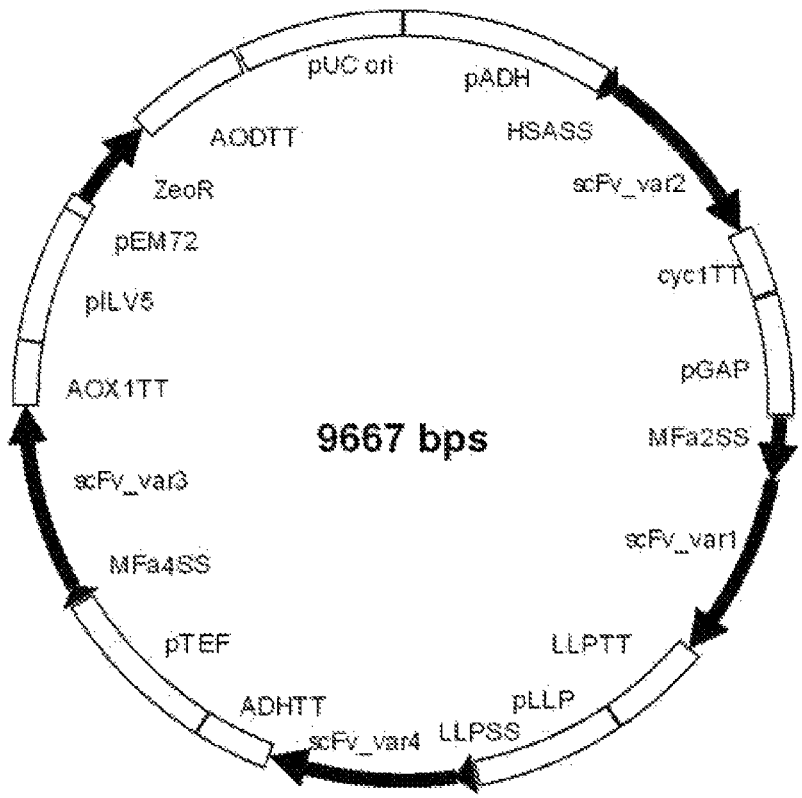

Figure 2:

Sequences of the yeast-vectors of Fig. 1A to Fig. 1D coding for one, two, three or four copies of the same POI

Figure 2A: yeast vector Y391_1xGOI (SEQ-ID NO. 1)

```
CCCGTAGAAAAGATCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTTCTTCTAGTGTAGCCG
TAGTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGATAG
TTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGGTACCC
AGATCCAATTCCCGCTTTGACTGCCTGAAATCTCCATCGCCTACAATGATGACATTTGGATTT
GGTTGACTCATGTTGGTATTGTGAAATAGACGCAGATCGGGAACACTGAAAAATACACAGTTA
TTATTCATTTAAATCACGGTCTTGGAGTCATCAGGCTCTGACTGGGCAGCTGCTGCAACTGGA
ACTTCCCAAGCCTCCCACCAAACAGCAGGTGTAGCCGAAAGTATTCACGTGTCCCAGAATGAG
GCCCACAGTACATCTGTCACCGTTTCTCAACCCCTTCAACGGTTTCTTTGCAAATTGGAGAA
GCAAATACCCTGAAATGGTCAGCTTTCTTTGGAGTAGTAGTTCCGCTGCTCAACGTACTCTTC
GTTTAAAAGCCCTCCTAGGACAAAATGGCCAAGCTGGGAAACGGGATTTGGTGGAACTTTATT
ATTCTTTCTACGATCCAAGCATTATGTTGTGGAACAAAGCGAATACTCTTATTAGCTGGTAAT
TGAGCGAGTTGAAAAAATCAAGTCTATTGGAGGGTATGGTCAGAGTACTGATAGAGATCCCTG
TTAAGATAATCGATCTTTTTCAAATATCCAATTTCATTCCATCTTGCCATCGGGTCTTGGCTT
CTTACATCAATAATTAAAACTACTTACTCTATTAGTGCCAAAAATGGTAAACCGTATTCAAAT
TGCTGCAAGCATATGCTTAAAAGGATCGCGTTGCGAGCTTCTTTTGAGATTCGCAAGCTTGAT
TTTATGCTCTTGTGGGAAGAAAAGCAACCCACTGAATTCCAGATTTGTTGTGTTTTCATGCAT
GGACGACATACTTTGAGTAATACCGTTACTGAGATTTTACCGAATTCGCATTGCGTTGAGGCG
TGAAGTTTCTTAATGCTGTGCCATATGGTTAAGTTGCGTTTCAAGATGGTCCACAAGTATTTT
TGTATTTAAGCAGTGTCAATTCAAGCCTAACTGCTCATAAAAACTACACGGTTTGCTGATATC
AAAAACGATGTTTGAAGAGTAAATTTGTGGTTTCGTTTCTGCTTTTACTCCAGCTATTTTG
TGTCCTTGGTGTACATGGAGAAATTGTCATGACCCAAAGTCCATCAACTCTTTCTGCCTCAGT
TGGTGATAGAGTTATCATTACTTGTCAGAGTTCTCAATCTGTGTTCAACAATTACTTGAGCTG
GTACCAACAAAAACCTGGTAGAGCCCCAAACTGTTAATCTACGATGCATCCAAACTGGCTAG
CGGAGTACCTTCTAGGTTTAGCGGTTCCGGATCAGGTGCAGAATTTACACTGACAATATCCTC
TTTGCAACCAGACGACTTTGCCACATACTATTGCCAAGGTTCGGATTATAGCGGTGGTTGGGA
CTCCGCGTTTGGTCAAGGTACCAAGTTGACTGTTCTCGGTGGAGGTGGAGGTTCTGGTGGTGG
AGGATCAGGTGGTGGCGGATCTGGCGGTGGAGGGTCCGAGGTGCAGTTGGTAGAGTCGGGCGG
TGGATCAGTCCAGCCTGGTGGATCCTTGAGACTTTCCTGTACCGCTTCTGGTATCGACTTATC
CAGTTATCCCATGTCGTGGGTTAGACAAGCTCCGGGAAAGGGTTTGGAATGGGTTGGTATCAT
```

Figure 2A (continued)

```
CAGCACTAGAGGAAATACTTACTACGCTACTTGGGCTAAGGGACGTTTTACAATTAGTAGAGA
TACGTCTAAAAACACTGTGTATTTGCAGATGAATTCACTAAGAGCCGAGGACACTGCAACTTA
CTACTGTGCACGTGGTCTTTACGGTAATAACTATTATGGAGCTTTCAATTTGTGGGGACAAGG
CACAACTGTAACGGTGTCCTCATAATAAGCGGCCGCAGCGAATTTCTTATGATTTATGATTTT
TATTATTAAATAAGTTATAAAAAAAATAAGTGTATACAAATTTTAAAGTGACTCTTAGGTTTT
AAAACGAAAATTCTTATTCTTGAGTAACTCTTTCCTGTAGGTCAGGTTGCTTTCTCAGGTATA
GCATGAGGTCGCTCTTATTGACCACACCTCTACCGGCATGCCGAGCAAATGCCTGCAAATCGC
TCCCCATTTCACCCAATTGTAGATATGCTAACTCCAGCAATGAGTTGATGAATCTCGGTGTGT
ATTTTATGTCCTCAGAGGACAAGGATCCTTCAGTAATGTCTTGTTTCTTTTGTTGCAGTGGTG
AGCCATTTTGACTTCGTGAAAGTTTCTTTAGAATAGTTGTTTCCAGAGGCCAAACATTCCACC
CGTAGTAAAGTGCAAGCGTAGGAAGACCAAGACTGGCATAAATCAGGTATAAGTGTCGAGCAC
TGGCAGGTGATCTTCTGAAAGTTTCTACTAGCAGATAAGATCCAGTAGTCATGCATATGGCAA
CAATGTACCGTGTGGATCTAAGAACGCGTCCTACTAACCTTCGCATTCGTTGGTCCAGTTTGT
TGTTATCGATCAACGTGACAAGGTTGTCGATTCCGCGTAAGCATGCATACCCAAGGACGCCTG
TTGCAATTCCAAGTGAGCCAGTTCCAACAATCTTTGTAATATTAGAGCACTTCATTGTGTTGC
GCTTGAAAGTAAAATGCGAACAAATTAAGAGATAATCTCGAAACCGCGACTTCAAACGCCAAT
ATGATGTGCGGCACACAATAAGCGTTCATATCCGCTGGGTGACTTTCTCGCTTTAAAAAATTA
TCCGAAAAAATTTTCTAGAGTGTTGACACTTTATACTTCCGGCTCGTATAATACGACAAGGTG
TAAGGAGGACTAAACCATGGCTAAACTCACCTCTGCTGTTCCAGTCCTGACTGCTCGTGATGT
TGCTGGTGCTGTTGAGTTCTGGACTGATAGACTCGGTTTCTCCCGTGACTTCGTAGAGGACGA
CTTTGCCGGTGTTGTACGTGACGACGTTACCCTGTTCATCTCCGCAGTTCAGGACCAGGTTGT
GCCAGACAACACTCTGGCATGGGTATGGGTTCGTGGTCTGGACGAACTGTACGCTGAGTGGTC
TGAGGTCGTGTCTACCAACTTCCGTGATGCATCTGGTCCAGCTATGACCGAGATCGGTGAACA
GCCCTGGGGTCGTGAGTTTGCACTGCGTGATCCAGCTGGTAACTGCGTGCATTTCGTCGCAGA
AGAGCAGGACTAACCTCTAGGACACCTTACGATTATTTAGAGAGTATTTATTAGTTTTATTGT
ATGTATACGGATGTTTTATTATCTATTTATGCCCTTATATTCTGTAACTATCCAAAAGTCCTA
TCTTATCAAGCCAGCAATCTATGTCCGCGAACGTCAACTAAAAATAAGCTTTTTATGCTCTTC
TCTCTTTTTTTCCCTTCGGTATAATTATACCTTGCATCCACAGATTCTCCTGCCAAATTTTGC
ATAATCCTTTACAACATGGCTATATGGGAGCACTTAGCGCCCTCCAAAACCCATATTGCCTAC
GCATGTATAGGTGTTTTTTCCACAATATTTTCTCTGTGCTCTCTTTTATTAAAGAGAAGCTC
TATATCGGAGAAGCTTCTGTGGCCGTTATATTCGGCCTTATCGTGGGACCACATTGCCTGAAT
TGGTTTGCCCCGGAAGATTGGGGAAACTTGGATCTGATTACCTTAGCTGCAGGTACCACTGAG
CGTCAGAC
```

Figure 2B: yeast vector Y393_2xGOI (SEQ-ID NO. 2)

```
CCCGTAGAAAAGATCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTTCTTCTAGTGTAGCCG
TAGTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGATAG
TTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATCGCGATAGAATAGCCGTAT
```

Figure 2B (continued)

```
GGGCTTTTTGTAGAAATGTCTTGGTGTCCTCGTCCAATCAGGTAGCCATCTCTGAAATATCTG
GCTCCGTTGCAACTCCGAACGACCTGCTGGCAACGTAAAATTCTCCGGGGTAAAACTTAAATG
TGGAGTAATGGAACCAGAAACGTCTCTTCCCTTCTCTCTCCTTCCACCGCCCGTTACCGTCAC
TAGGAAATTTTACTCTGCTGGAGAGCTTCTTCTACGGCCCCCTTGCAGCAATGCTCTTCCCAG
CATTACGTTGCGGGTAAAACGGAGGTCGTGTACCCGACCTAGCAGCCCAGGGATGGAAAAGTC
CCGGCCGTCGCTGGCAATAATAGCGGGCGGACGCATGTCATGAGATTATTGGAAACCACCAGA
ATCGAATATAAAAGGCGAACACCTTTCCCAATTTTGGTTTCTCCTGACCCAAAGACTTTAAAT
TTAATTTATTTGTCCCTATTTCAATCAATTGAACAACTATCAAAACACACTCGAGCAAAACGA
TGCGTTTCCCATCGATTTTCACAGCTGTTCTGTTTGCAGCTTCATCTGCTTTAGCTGCACCTG
TTAACACAACTACAGAGGACGAAACGGCCCAGATCCCAGCTGAGGCAGTCATTGGTTATTCCG
ATTTGGAAGGTGATTTCGATGTCGCTGTGTTACCATTCAGTAATTCCACAAATAACGGTTTGC
TGTTCATTAACACCACTATAGCAAGCATCGCTGCAAAAGAGGAAGGTGTTTCCCTAGAAAAGA
GGGAGATTGTTATGACGCAGTCCCCAGTACTTTGTCTGCTTCCGTTGGAGATAGAGTAATCA
TAACTTGTCAATCCTCTCAATCTGTCTTTAACAATTACCTTTCTTGGTACCAACAGAAACCAG
GCAGGGCTCCAAAGTTGCTAATCTATGATGCATCTAAACTGGCCTCCGGTGTTCCATCACGTT
TTTCAGGTTCAGGATCCGGTGCTGAGTTCACTTTAACGATTTCCTCGTTGCAACCGGATGACT
TTGCCACATATTACTGTCAAGGTTCTGACTACTCAGGTGGTTGGGACTCTGCTTTCGGTCAAG
GTACCAAACTGACTGTATTGGGAGGAGGTGGAGGTAGCGGCGGTGGAGGTTCAGGAGGTGGTG
GATCCGGAGGGGGTGGAAGTGAAGTTCAATTGGTGGAAAGCGGTGGTGGTTCCGTTCAGCCTG
GAGGTAGCTTGCGTCTGTCGTGCACTGCAAGTGGTATTGACTTAAGCTCATATCCTATGTCTT
GGGTCAGACAAGCACCTGGTAAGGGTTTGGAGTGGGTCGGCATCATTAGCACTAGAGGTAACA
CATACTATGCTACATGGGCAAAGGGAAGATTCACAATCTCACGTGATACATCTAAAAATACAG
TTTATCTTCAGATGAATAGTCTCAGAGCTGAAGATACAGCTACCTACTACTGTGCCAGAGGAT
TATACGGTAATAACTATTATGGTGCATTCAATCTATGGGGCCAAGGTACTACTGTGACCGTGT
CCTCGTAATAGAGGCCTTGTTCTTTCCTGCGGTACCCAGATCCAATTCCGCTTTGACTGCCT
GAAATCTCCATCGCCTACAATGATGACATTTGGATTTGGTTGACTCATGTTGGTATTGTGAAA
TAGACGCAGATCGGGAACACTGAAAAATACACAGTTATTATTCATTTAAATCACGGTCTTGGA
GTCATCAGGCTCTGACTGGGCAGCTGCTGCAACTGGAACTTCCCAAGCCTCCCACCAAACAGC
AGGTGTAGCCGAAAGTATTCACGTGTCCCAGAATGAGGCCCACAGTACATCTGTCACCGTTTC
TCAACCCCCTTCAACGGTTTCTTTGCAAATTGGAGAAGCAAATACCCTGAAATGGTCAGCTTT
CTTTGGAGTAGTAGTTCCGCTGCTAACGTACTCTTCGTTTAAAAGCCCTCCTAGGACAAAAT
GGCCAAGCTGGGAAACGGGATTTGGTGGAACTTTATTATTCTTTCTACGATCCAAGCATTATG
TTGTGGAACAAAGCGAATACTCTTATTAGCTGGTAATTGAGCGAGTTGAAAAAATCAAGTCTA
TTGGAGGGTATGGTCAGAGTACTGATAGAGATCCCTGTTAAGATAATCGATCTTTTTCAAATA
TCCAATTTCATTCCATCTTGCCATCGGGTCTTGGCTTCTTACATCAATAATTAAAACTACTTA
CTCTATTAGTGCCAAAAATGGTAAACCGTATTCAAATTGCTGCAAGCATATGCTTAAAGGAT
CGCGTTGCGAGCTTCTTTTGAGATTCGCAAGCTTGATTTTATGCTCTTGTGGGAAGAAAAGCA
ACCCACTGAATTCCAGATTTGTTGTGTTTTCATGCATGGACGACATACTTTGAGTAATACCGT
TACTGAGATTTTACCGAATTCGCATTGCGTTGAGGCGTGAAGTTTCTTAATGCTGTGCCATAT
GGTTAAGTTGCGTTTCAAGATGGTCCACAAGTATTTTTGTATTTAAGCAGTGTCAATTCAAGC
CTAACTGCTCATAAAAACTACACGGTTTGCTGATATCAAAAACGATGTTTGAGAAGAGTAAAT
TTGTGGTTTCGTTTCTGCTTTTACTCCAGCTATTTTGTGTCCTTGGTGTACATGGAGAAATTG
TCATGACCCAAAGTCCATCAACTCTTTCTGCCTCAGTTGGTGATAGAGTTATCATTACTTGTC
AGAGTTCTCAATCTGTGTTCAACAATTACTTGAGCTGGTACCAACAAAAACCTGGTAGAGCCC
CCAAACTGTTAATCTACGATGCATCCAAACTGGCTAGCGGAGTACCTTCTAGGTTTAGCGGTT
CCGGATCAGGTGCAGAATTTACACTGACAATATCCTCTTTGCAACCAGACGACTTTGCCACAT
ACTATTGCCAAGGTTCGGATTATAGCGGTGGTTGGGACTCCGCGTTTGGTCAAGGTACCAAGT
TGACTGTTCTCGGTGGAGGTGGAGGTTCTGGTGGTGGAGGATCAGGTGGTGGCGGATCTGGCG
```

Figure 2B (continued)

```
GTGGAGGGTCCGAGGTGCAGTTGGTAGAGTCGGGCGGTGGATCAGTCCAGCCTGGTGGATCCT
TGAGACTTTCCTGTACCGCTTCTGGTATCGACTTATCCAGTTATCCCATGTCGTGGGTTAGAC
AAGCTCCGGGAAAGGGTTTGGAATGGGTTGGTATCATCAGCACTAGAGGAAATACTTACTACG
CTACTTGGGCTAAGGGACGTTTTACAATTAGTAGAGATACGTCTAAAAACACTGTGTATTTGC
AGATGAATTCACTAAGAGCCGAGGACACTGCAACTTACTACTGTGCACGTGGTCTTTACGGTA
ATAACTATTATGGAGCTTTCAATTTGTGGGACAAGGCACAACTGTAACGGTGTCCTCATAAT
AAGCGGCCGCAGCGAATTTCTTATGATTTATGATTTTTATTATTAAATAAGTTATAAAAAAA
TAAGTGTATACAAATTTTAAAGTGACTCTTAGGTTTTAAAACGAAAATTCTTATTCTTGAGTA
ACTCTTTCCTGTAGGTCAGGTTGCTTTCTCAGGTATAGCATGAGGTCGCTCTTATTGACCACA
CCTCTACCGGCATGCCGAGCAAATGCCTGCAAATCGCTCCCCATTTCACCCAATTGTAGATAT
GCTAACTCCAGCAATGAGTTGATGAATCTCGGTGTGTATTTATGTCCTCAGAGGACAAGGAT
CCTTCAGTAATGTCTTGTTTCTTTTGTTGCAGTGGTGAGCCATTTTGACTTCGTGAAAGTTTC
TTTAGAATAGTTGTTTCCAGAGGCCAAACATTCCACCCGTAGTAAAGTGCAAGCGTAGGAAGA
CCAAGACTGGCATAAATCAGGTATAAGTGTCGAGCACTGGCAGGTGATCTTCTGAAAGTTTCT
ACTAGCAGATAAGATCCAGTAGTCATGCATATGGCAACAATGTACCGTGTGGATCTAAGAACG
CGTCCTACTAACCTTCGCATTCGTTGGTCCAGTTTGTTGTTATCGATCAACGTGACAAGGTTG
TCGATTCCGCGTAAGCATGCATACCCAAGGACGCCTGTTGCAATTCCAAGTGAGCCAGTTCCA
ACAATCTTTGTAATATTAGAGCACTTCATTGTGTTGCGCTTGAAAGTAAAATGCAACAAATT
AAGAGATAATCTCGAAACCGCGACTTCAAACGCCAATATGATGTGCGGCACACAATAAGCGTT
CATATCCGCTGGGTGACTTTCTCGCTTTAAAAAATTATCCGAAAAATTTTCTAGAGTGTTGA
CACTTTATACTTCCGGCTCGTATAATACGACAAGGTGTAAGGAGGACTAAACCATGGCTAAAC
TCACCTCTGCTGTTCCAGTCCTGACTGCTCGTGATGTTGCTGGTGCTGTTGAGTTCTGGACTG
ATAGACTCGGTTTCTCCCGTGACTTCGTAGAGGACGACTTTGCCGGTGTTGTACGTGACGACG
TTACCCTGTTCATCTCCGCAGTTCAGGACCAGGTTGTGCCAGACAACACTCTGGCATGGGTAT
GGGTTCGTGGTCTGGACGAACTGTACGCTGAGTGGTCTGAGGTCGTGTCTACCAACTTCCGTG
ATGCATCTGGTCCAGCTATGACCGAGATCGGTGAACAGCCCTGGGGTCGTGAGTTTGCACTGC
GTGATCCAGCTGGTAACTGCGTGCATTTCGTCGCAGAAGAGCAGGACTAACCTCTAGGACACC
TTACGATTATTTAGAGAGTATTTATTAGTTTTATTGTATGTATACGGATGTTTTATTATCTAT
TTATGCCCTTATATTCTGTAACTATCCAAAAGTCCTATCTTATCAAGCCAGCAATCTATGTCC
GCGAACGTCAACTAAAAATAAGCTTTTTATGCTCTTCTCTCTTTTTTTCCCTTCGGTATAATT
ATACCTTGCATCCACAGATTCTCCTGCCAAATTTTGCATAATCCTTTACAACATGGCTATATG
GGAGCACTTAGCGCCCTCCAAAACCCATATTGCCTACGCATGTATAGGTGTTTTTTCCACAAT
ATTTTCTCTGTGCTCTCTTTTTATTAAAGAGAAGCTCTATATCGGAGAAGCTTCTGTGGCCGT
TATATTCGGCCTTATCGTGGGACCACATTGCCTGAATTGGTTTGCCCCGGAAGATTGGGGAAA
CTTGGATCTGATTACCTTAGCTGCAGGTACCACTGAGCGTCAGAC
```

Figure 2C: yeast vector Y394_3xGOI (SEQ-ID NO. 3)

```
CGATTTATTATGTTACAATATGGAAGGGAACTTTACACTTCTCCTATGCACATATATTAATTA
AAGTCCAATGCTAGTAGAGAAGGGGGGTAACACCCCTCCGCGCTCTTTTCCGATTTTTTTCTA
AACCGTGGAATATTTCGCATATCCTTTTGTTGTTTCCGGGTGTACAATATGGACTTCCTCTTT
TCTGGCAACCAAACCCATACATCGGGATTCCTATAATACCTTCGTTGGTCTCCCTAACATGTA
GGTGGCGGAGGGGAGATATACAATAGAACAGATACCAGACAAGACATAATGGGCTAAACAAGA
CTACACCAATTACACTGCCTCATTGATGGTGGTACATAACGAACTAATACTGTAGCCCTAGAC
TTGATAGCCATCATCATATCGAAGTTTCACTACCCTTTTTCCATTTGCCATCTATTGAAGTAA
TAATAGGCGCATGCAACTTCTTTTCTTTTTTTTCTTTTCTCTCTCCCCGTTGTTGTCTCAC
CATATCCGCAATGACAAAAAATGATGGAAGACACTAAAGGAAAAATTAACGACAAGACAG
CACCAACAGATGTCGTTGTTCCAGAGCTGATGAGGGGTATCTCGAAGCACACGAAACTTTTC
CTTCCTTCATTCACGCACACTACTCTCTAATGAGCAACGGTATACGGCCTTCCTTCCAGTTAC
```

Figure 2C (continued)

```
TTGAATTTGAAATAAAAAAAAGTTTGCTGTCTTGCTATCAAGTATAAATAGACCTGCAATTAT
TAATCTTTTGTTTCCTCGTCATTGTTCTCGTTCCCTTTCTTCCTTGTTTCTTTTTCTGCACAA
TATTTCAAGCTATACCAAGCATACAATCAACTATCTCATATACAGTCGACCAAAACGATGAAG
TGGGTCACTTTCATCTCGCTGCTATTTTGTTCTCCAGCGCCTATAGCGAGATTGTGATGACT
CAATCCCCTTCCACTCTAAGCGCTTCTGTCGGTGACCGTGTTATCATTACCTGTCAATCCTCT
CAATCGGTTTTCAACAATTACTTATCCTGGTATCAACAGAAGCCAGGTCGTGCACCTAAACTT
CTGATTTACGATGCTTCAAAATTGGCTAGTGGTGTCCCAAGCAGATTTTCGGGATCTGGTTCC
GGTGCCGAGTTTACACTCACGATCTCCTCACTTCAACCCGATGATTTCGCAACATACTATTGT
CAAGGTAGCGACTATAGTGGAGGTTGGGACTCTGCCTTTGGACAAGGTACTAAGCTAACAGTT
TTGGGTGGAGGCGGAGGTTCGGGTGGTGGTGGATCAGGAGGAGGTGGTAGTGGCGGAGGAGGC
TCAGAAGTGCAACTGGTTGAAAGTGGTGGAGGTTCCGTTCAGCCAGGGGGTTCCTTGAGATTG
TCTTGCACTGCTTCTGGTATCGACCTGTCATCATACCCAATGAGCTGGGTAAGACAGGCTCCT
GGTAAAGGTTTGGAATGGGTTGGAATTATCTCTACTCGTGGTAATACATATTACGCAACATGG
GCTAAGGGTAGATTCACAATATCCAGGGATACTTCCAAAAACACAGTATACTTACAAATGAAT
TCTTTGAGAGCCGAGGATACCGCTACCTATTACTGTGCAAGGGGTCTGTATGGTAACAATTAC
TATGGAGCATTCAATTTGTGGGGTCAGGGCACGACTGTGACTGTCAGCTCATAATAGAGATCT
CCTTTTCCTTTGTCCATATCATGTAATTAGTTATGTCACGCTTACATTCACGCCCTCCCCCCA
CATCCGCTCTAACCGAAAAGGAAGGAGTTAGACAACCTGAAGTCTAGGTCCCTATTTATTTTT
TTATAGTTATGTTAGTATTAAGAACGTTATTTATATTTCAAATTTTTCTTTTTTTTCTGTACA
GACGCGTGTACGCATGTAACATTATACTGAAAACCTTGCTTGAGAAGGTTTTGGGACGCTCGA
AGGCTTTAATTTGCAAGCTGCCGTATGGGCTTTTTGTAGAAATGTCTTGGTGTCCTCGTCCAA
TCAGGTAGCCATCTCTGAAATATCTGGCTCCGTTGCAACTCCGAACGACCTGCTGGCAACGTA
AAATTCTCCGGGGTAAAACTTAAATGTGGAGTAATGGAACCAGAAACGTCTCTTCCCTTCTCT
CTCCTTCCACCGCCCGTTACCGTCACTAGGAAATTTTACTCTGCTGGAGAGCTTCTTCTACGG
CCCCCTTGCAGCAATGCTCTTCCCAGCATTACGTTGCGGGTAAAACGGAGGTCGTGTACCCGA
CCTAGCAGCCCAGGGATGGAAAAGTCCCGGCCGTCGCTGGCAATAATAGCGGGCGGACGCATG
TCATGAGATTATTGGAAACCACCAGAATCGAATATAAAAGGCGAACACCTTTCCCAATTTTGG
TTTCTCCTGACCCAAAGACTTTAAATTTAATTTATTTGTCCCTATTTCAATCAATTGAACAAC
TATCAAAACACACTCGAGCAAAACGATGCGTTTCCCATCGATTTTCACAGCTGTTCTGTTTGC
AGCTTCATCTGCTTTAGCTGCACCTGTTAACACAACTACAGAGGACGAAACGGCCCAGATCCC
AGCTGAGGCAGTCATTGGTTATTCCGATTTGGAAGGTGATTTCGATGTCGCTGTGTTACCATT
CAGTAATTCCACAAATAACGGTTTGCTGTTCATTAACACCACTATAGCAAGCATCGCTGCAAA
AGAGGAAGGTGTTTCCCTAGAAAAGAGGGAGATTGTTATGACGCAGTCCCCCAGTACTTTGTC
TGCTTCCGTTGGAGATAGAGTAATCATAACTTGTCAATCCTCTCAATCTGTCTTTAACAATTA
CCTTTCTTGGTACCAACAGAAACCAGGCAGGGCTCCAAAGTTGCTAATCTATGATGCATCTAA
ACTGGCCTCCGGTGTTCCATCACGTTTTTCAGGTTCAGGATCCGGTGCTGAGTTCACTTTAAC
GATTTCCTCGTTGCAACCGGATGACTTTGCCACATATTACTGTCAAGGTTCTGACTACTCAGG
TGGTTGGGACTCTGCTTTCGGTCAAGGTACCAAACTGACTGTATTGGGAGGAGGTGGAGGTAG
CGGCGGTGGAGGTTCAGGAGGTGGTGGATCCGGAGGGGTGGAAGTGAAGTTCAATTGGTGGA
AAGCGGTGGTGGTTCCGTTCAGCCTGGAGGTAGCTTGCGTCTGTCGTGCACTGCAAGTGGTAT
TGACTTAAGCTCATATCCTATGTCTTGGGTCAGACAAGCACCTGGTAAGGGTTTGGAGTGGGT
CGGCATCATTAGCACTAGAGGTAACACATACTATGCTACATGGGCAAAGGGAAGATTCACAAT
CTCACGTGATACATCTAAAAATACAGTTTATCTTCAGATGAATAGTCTCAGAGCTGAAGATAC
AGCTACCTACTACTGTGCCAGAGGATTATACGGTAATAACTATTATGGTGCATTCAATCTATG
GGGCCAAGGTACTACTGTGACCGTGTCCTCGTAATAGAGGCCTTGTTCTTTCCTGCGGTACCC
AGATCCAATTCCCGCTTTGACTGCCTGAAATCTCCATCGCCTACAATGATGACATTTGGATTT
GGTTGACTCATGTTGGTATTGTGAAATAGACGCAGATCGGGAACACTGAAAAATACACAGTTA
TTATTCATTTAAATCACGGTCTTGGAGTCATCAGGCTCTGACTGGGCAGCTGCTGCAACTGGA
```

Figure 2C (continued)

```
ACTTCCCAAGCCTCCCACCAAACAGCAGGTGTAGCCGAAAGTATTCACGTGTCCCAGAATGAG
GCCCACAGTACATCTGTCACCGTTTCTAACCCCCTTCAACGGTTTCTTTGCAAATTGGAGAA
GCAAATACCCTGAAATGGTCAGCTTTCTTTGGAGTAGTAGTTCCGCTGCTCAACGTACTCTTC
GTTTAAAAGCCCTCCTAGGACAAAATGGCCAAGCTGGGAACGGGATTTGGTGGAACTTTATT
ATTCTTTCTACGATCCAAGCATTATGTTGTGGAACAAAGCGAATACTCTTATTAGCTGGTAAT
TGAGCGAGTTGAAAAAATCAAGTCTATTGGAGGGTATGGTCAGAGTACTGATAGAGATCCCTG
TTAAGATAATCGATCTTTTTCAAATATCCAATTTCATTCCATCTTGCCATCGGGTCTTGGCTT
CTTACATCAATAATTAAAACTACTTACTCTATTAGTGCCAAAAATGGTAAACCGTATTCAAAT
TGCTGCAAGCATATGCTTAAAAGGATCGCGTTGCGAGCTTCTTTTGAGATTCGCAAGCTTGAT
TTTATGCTCTTGTGGGAAGAAAAGCAACCCACTGAATTCCAGATTTGTTGTGTTTTCATGCAT
GGACGACATACTTTGAGTAATACCGTTACTGAGATTTTACCGAATTCGCATTGCGTTGAGGCG
TGAAGTTTCTTAATGCTGTGCCATATGGTTAAGTTGCGTTTCAAGATGGTCCACAAGTATTTT
TGTATTTAAGCAGTGTCAATTCAAGCCTAACTGCTCATAAAAACTACACGGTTTGCTGATATC
AAAAACGATGTTTGAGAAGAGTAAATTTGTGGTTTCGTTTCTGCTTTTACTCCAGCTATTTTG
TGTCCTTGGTGTACATGGAGAAATTGTCATGACCCAAAGTCCATCAACTCTTTCTGCCTCAGT
TGGTGATAGAGTTATCATTACTTGTCAGAGTTCTCAATCTGTGTTCAACAATTACTTGAGCTG
GTACCAACAAAACCTGGTAGAGCCCCAAACTGTTAATCTACGATGCATCCAAACTGGCTAG
CGGAGTACCTTCTAGGTTTAGCGGTTCCGGATCAGGTGCAGAATTTACACTGACAATATCCTC
TTTGCAACCAGACGACTTTGCCACATACTATTGCCAAGGTTCGGATTATAGCGGTGGTTGGGA
CTCCGCGTTTGGTCAAGGTACCAAGTTGACTGTTCTCGGTGGAGGTGGAGGTTCTGGTGGTGG
AGGATCAGGTGGTGGCGGATCTGGCGGTGGAGGGTCCGAGGTGCAGTTGGTAGAGTCGGGCGG
TGGATCAGTCCAGCCTGGTGGATCCTTGAGACTTTCCTGTACCGCTTCTGGTATCGACTTATC
CAGTTATCCCATGTCGTGGGTTAGACAAGCTCCGGGAAAGGGTTTGGAATGGGTTGGTATCAT
CAGCACTAGAGGAAATACTTACTACGCTACTTGGGCTAAGGGACGTTTTACAATTAGTAGAGA
TACGTCTAAAAACACTGTGTATTTGCAGATGAATTCACTAAGAGCCGAGGACACTGCAACTTA
CTACTGTGCACGTGGTCTTTACGGTAATAACTATTATGGAGCTTTCAATTTGTGGGGACAAGG
CACAACTGTAACGGTGTCCTCATAATAAGCGGCCGCAGCGAATTTCTTATGATTTATGATTTT
TATTATTAAATAAGTTATAAAAAAAATAAGTGTATACAAATTTTAAAGTGACTCTTAGGTTTT
AAAACGAAAATTCTTATTCTTGAGTAACTCTTTCCTGTAGGTCAGGTTGCTTTCTCAGGTATA
GCATGAGGTCGCTCTTATTGACCACACCTCTACCGGCATGCCGAGCAAATGCCTGCAAATCGC
TCCCCATTTCACCCAATTGTAGATATGCTAACTCCAGCAATGAGTTGATGAATCTCGGTGTGT
ATTTTATGTCCTCAGAGGACAAGGATCCTTCAGTAATGTCTTGTTTCTTTTGTTGCAGTGGTG
AGCCATTTTGACTTCGTGAAAGTTTCTTTAGAATAGTTGTTTCCAGAGGCCAAACATTCCACC
CGTAGTAAAGTGCAAGCGTAGGAAGACCAAGACTGGCATAAATCAGGTATAAGTGTCGAGCAC
TGGCAGGTGATCTTCTGAAAGTTTCTACTAGCAGATAAGATCCAGTAGTCATGCATATGGCAA
CAATGTACCGTGTGGATCTAAGAACGCGTCCTACTAACCTTCGCATTCGTTGGTCCAGTTTGT
TGTTATCGATCAACGTGACAAGGTTGTCGATTCCGCGTAAGCATGCATACCCAAGGACGCCTG
TTGCAATTCCAAGTGAGCCAGTTCCAACAATCTTTGTAATATTAGAGCACTTCATTGTGTTGC
GCTTGAAAGTAAAATGCGAACAAATTAAGAGATAATCTCGAAACCGCGACTTCAAACGCCAAT
ATGATGTGCGGCACACAATAAGCGTTCATATCCGCTGGGTGACTTTCTCGCTTTAAAAAATTA
TCCGAAAAATTTTCTAGAGTGTTGACACTTTATACTTCCGGCTCGTATAATACGACAAGGTG
TAAGGAGGACTAAACCATGGCTAAACTCACCTCTGCTGTTCCAGTCCTGACTGCTCGTGATGT
TGCTGGTGCTGTTGAGTTCTGGACTGATAGACTCGGTTTCTCCCGTGACTTCGTAGAGGACGA
CTTTGCCGGTGTTGTACGTGACGACGTTACCCTGTTCATCTCCGCAGTTCAGGACCAGGTTGT
GCCAGACAACACTCTGGCATGGGTATGGGTTCGTGGTCTGGACGAACTGTACGCTGAGTGGTC
TGAGGTCGTGTCTACCAACTTCCGTGATGCATCTGGTCCAGCTATGACCGAGATCGGTGAACA
GCCCTGGGGTCGTGAGTTTGCACTGCGTGATCCAGCTGGTAACTGCGTGCATTTCGTCGCAGA
AGAGCAGGACTAACCTCTAGGACACCTTACGATTATTTAGAGAGTATTTATTAGTTTTATTGT
```

Figure 2C (continued)

```
ATGTATACGGATGTTTTATTATCTATTTATGCCCTTATATTCTGTAACTATCCAAAAGTCCTA
TCTTATCAAGCCAGCAATCTATGTCCGCGAACGTCAACTAAAAATAAGCTTTTTATGCTCTTC
TCTCTTTTTTTCCCTTCGGTATAATTATACCTTGCATCCACAGATTCTCCTGCCAAATTTTGC
ATAATCCTTTACAACATGGCTATATGGGAGCACTTAGCGCCCTCCAAAACCCATATTGCCTAC
GCATGTATAGGTGTTTTTTCCACAATATTTTCTCTGTGCTCTCTTTTTATTAAAGAGAAGCTC
TATATCGGAGAAGCTTCTGTGGCCGTTATATTCGGCCTTATCGTGGGACCACATTGCCTGAAT
TGGTTTGCCCCGGAAGATTGGGGAAACTTGGATCTGATTACCTTAGCTGCAGGTACCACTGAG
CGTCAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAG
TGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAAAGCGCCA
CGCTTCCCGAAGGGAGAAAGGCGGACAGGTATCCGGTAAGCGGCAGGGTCGGAACAGGAGAGC
GCACGAGGGAGCTTCCAGGGGAAACGCCTGGTATCTTTATAGTCCTGTCGGGTTTCGCCACC
TCTGACTTGAGCGTCGATTTTGTGATGCTCGTCAGGGGGCGGAGCCTATGGAAAAACGCCA
GCAACGCGGCCTTTTTACGGTTCCTGGCCTTTTGCTGGCCTTTTGCTCACATCG
```

Figure 2D: yeast vector Y395_4xGOI (SEQ-ID NO. 4)

```
CGATTTATTATGTTACAATATGGAAGGGAACTTTACACTTCTCCTATGCACATATATTAATTA
AAGTCCAATGCTAGTAGAGAAGGGGGGTAACACCCCTCCGCGCTCTTTTCCGATTTTTTTCTA
AACCGTGGAATATTTCGCATATCCTTTTGTTGTTTCCGGGTGTACAATATGGACTTCCTCTTT
TCTGGCAACCAAACCCATACATCGGGATTCCTATAATACCTTCGTTGGTCTCCCTAACATGTA
GGTGGCGGAGGGGAGATATACAATAGAACAGATACCAGACAAGACATAATGGGCTAAACAAGA
CTACACCAATTACACTGCCTCATTGATGGTGGTACATAACGAACTAATACTGTAGCCCTAGAC
TTGATAGCCATCATCATATCGAAGTTTCACTACCCTTTTTCCATTTGCCATCTATTGAAGTAA
TAATAGGCGCATGCAACTTCTTTTCTTTTTTTTTCTTTTCTCTCTCCCCGTTGTTGTCTCAC
CATATCCGCAATGACAAAAAAATGATGGAAGACACTAAAGGAAAAAATTAACGACAAAGACAG
CACCAACAGATGTCGTTGTTCCAGAGCTGATGAGGGGTATCTCGAAGCACACGAAACTTTTTC
CTTCCTTCATTCACGCACACTACTCTCTAATGAGCAACGGTATACGGCCTTCCTTCCAGTTAC
TTGAATTTGAAATAAAAAAAAGTTTGCTGTCTTGCTATCAAGTATAAATAGACCTGCAATTAT
TAATCTTTTGTTTCCTCGTCATTGTTCTCGTTCCCTTTCTTCCTTGTTTCTTTTTCTGCACAA
TATTTCAAGCTATACCAAGCATACAATCAACTATCTCATATACAGTCGACCAAAACGATGAAG
TGGGTCACTTTCATCTCGCTGCTATTTTTGTTCTCCAGCGCCTATAGCGAGATTGTGATGACT
CAATCCCCTTCCACTCTAAGCGCTTCTGTCGGTGACCGTGTTATCATTACCTGTCAATCCTCT
CAATCGGTTTTCAACAATTACTTATCCTGGTATCAACAGAAGCCAGGTCGTGCACCTAAACTT
CTGATTTACGATGCTTCAAAATTGGCTAGTGGTGTCCCAAGCAGATTTTCGGGATCTGGTTCC
GGTGCCGAGTTTACACTCACGATCTCCTCACTTCAACCCGATGATTTCGCAACATACTATTGT
CAAGGTAGCGACTATAGTGGAGGTTGGGACTCTGCCTTTGGACAAGGTACTAAGCTAACAGTT
TTGGGTGGAGGCGGAGGTTCGGGTGGTGGTGGATCAGGAGGAGGTGGTAGTGGCGGAGGAGGC
TCAGAAGTGCAACTGGTTGAAAGTGGTGGAGGTTCCGTTCAGCCAGGGGGTTCCTTGAGATTG
TCTTGCACTGCTTCTGGTATCGACCTGTCATCATACCCAATGAGCTGGGTAAGACAGGCTCCT
GGTAAAGGTTTGGAATGGGTTGGAATTATCTCTACTCGTGGTAATACATATTACGCAACATGG
GCTAAGGGTAGATTCACAATATCCAGGGATACTTCCAAAAACACAGTATACTTACAAATGAAT
TCTTTGAGAGCCGAGGATACCGCTACCTATTACTGTGCAAGGGGTCTGTATGGTAACAATTAC
```

Figure 2D (continued)

```
TATGGAGCATTCAATTTGTGGGGTCAGGGCACGACTGTGACTGTCAGCTCATAATAGAGATCT
CCTTTTCCTTTGTCCATATCATGTAATTAGTTATGTCACGCTTACATTCACGCCCTCCCCCCA
CATCCGCTCTAACCGAAAAGGAAGGAGTTAGACAACCTGAAGTCTAGGTCCCTATTTATTTTT
TTATAGTTATGTTAGTATTAAGAACGTTATTTATATTTCAAATTTTTCTTTTTTTCTGTACA
GACGCGTGTACGCATGTAACATTATACTGAAAACCTTGCTTGAGAAGGTTTTGGGACGCTCGA
AGGCTTTAATTTGCAAGCTGCCGTATGGGCTTTTTGTAGAAATGTCTTGGTGTCCTCGTCCAA
TCAGGTAGCCATCTCTGAAATATCTGGCTCCGTTGCAACTCCGAACGACCTGCTGGCAACGTA
AAATTCTCCGGGGTAAAACTTAAATGTGGAGTAATGGAACCAGAAACGTCTCTTCCCTTCTCT
CTCCTTCCACCGCCCGTTACCGTCACTAGGAAATTTTACTCTGCTGGAGAGCTTCTTCTACGG
CCCCCTTGCAGCAATGCTCTTCCCAGCATTACGTTGCGGGTAAAACGGAGGTCGTGTACCCGA
CCTAGCAGCCCAGGGATGGAAAAGTCCCGGCCGTCGCTGGCAATAATAGCGGGCGGACGCATG
TCATGAGATTATTGGAAACCACCAGAATCGAATATAAAAGGCGAACACCTTTCCCAATTTTGG
TTTCTCCTGACCCAAAGACTTTAAATTTAATTTATTTGTCCCTATTTCAATCAATTGAACAAC
TATCAAAACACACTCGAGCAAAACGATGCGTTTCCCATCGATTTTCACAGCTGTTCTGTTTGC
AGCTTCATCTGCTTTAGCTGCACCTGTTAACACAACTACAGAGGACGAAACGGCCCAGATCCC
AGCTGAGGCAGTCATTGGTTATTCCGATTTGGAAGGTGATTTCGATGTCGCTGTGTTACCATT
CAGTAATTCCACAAATAACGGTTTGCTGTTCATTAACACCACTATAGCAAGCATCGCTGCAAA
AGAGGAAGGTGTTTCCCTAGAAAAGAGGGAGATTGTTATGACGCAGTCCCCAGTACTTTGTC
TGCTTCCGTTGGAGATAGAGTAATCATAACTTGTCAATCCTCTCAATCTGTCTTTAACAATTA
CCTTTCTTGGTACCAACAGAAACCAGGCAGGGCTCCAAAGTTGCTAATCTATGATGCATCTAA
ACTGGCCTCCGGTGTTCCATCACGTTTTTCAGGTTCAGGATCCGGTGCTGAGTTCACTTTAAC
GATTTCCTCGTTGCAACCGGATGACTTTGCCACATATTACTGTCAAGGTTCTGACTACTCAGG
TGGTTGGGACTCTGCTTTCGGTCAAGGTACCAAACTGACTGTATTGGGAGGAGGTGGAGGTAG
CGGCGGTGGAGGTTCAGGAGGTGGTGGATCCGGAGGGGGTGGAAGTGAAGTTCAATTGGTGGA
AAGCGGTGGTGGTTCCGTTCAGCCTGGAGGTAGCTTGCGTCTGTCGTGCACTGCAAGTGGTAT
TGACTTAAGCTCATATCCTATGTCTTGGGTCAGACAAGCACCTGGTAAGGGTTTGGAGTGGGT
CGGCATCATTAGCACTAGAGGTAACACATACTATGCTACATGGGCAAAGGGAAGATTCACAAT
CTCACGTGATACATCTAAAAATACAGTTTATCTTCAGATGAATAGTCTCAGAGCTGAAGATAC
AGCTACCTACTACTGTGCCAGAGGATTATACGGTAATAACTATTATGGTGCATTCAATCTATG
GGGCCAAGGTACTACTGTGACCGTGTCCTCGTAATAGAGGCCTTGTTCTTTCCTGCGGTACCC
AGATCCAATTCCCGCTTTGACTGCCTGAAATCTCCATCGCCTACAATGATGACATTTGGATTT
GGTTGACTCATGTTGGTATTGTGAAATAGACGCAGATCGGGAACACTGAAAAATACACAGTTA
TTATTCATTTAAATCACGGTCTTGGAGTCATCAGGCTCTGACTGGGCAGCTGCTGCAACTGGA
ACTTCCCAAGCCTCCCACCAAACAGCAGGTGTAGCCGAAAGTATTCACGTGTCCCAGAATGAG
GCCCACAGTACATCTGTCACCGTTTCTCAACCCCCTTCAACGGTTTCTTTGCAAATTGGAGAA
GCAAATACCCTGAAATGGTCAGCTTTCTTTGGAGTAGTAGTTCCGCTGCTCAACGTACTCTTC
GTTTAAAAGCCCTCCTAGGACAAAATGGCCAAGCTGGGAAACGGGATTTGGTGGAACTTTATT
ATTCTTTCTACGATCCAAGCATTATGTTGTGGAACAAAGCGAATACTCTTATTAGCTGGTAAT
TGAGCGAGTTGAAAAAATCAAGTCTATTGGAGGGTATGGTCAGAGTACTGATAGAGATCCCTG
TTAAGATAATCGATCTTTTTCAAATATCCAATTTCATTCCATCTTGCCATCGGGTCTTGGCTT
CTTACATCAATAATTAAAACTACTTACTCTATTAGTGCCAAAAATGGTAAACCGTATTCAAAT
TGCTGCAAGCATATGCTTAAAAGGATCGCGTTGCGAGCTTCTTTTGAGATTCGCAAGCTTGAT
TTTATGCTCTTGTGGGAAGAAAAGCAACCCACTGAATTCCAGATTTGTTGTGTTTTCATGCAT
GGACGACATACTTTGAGTAATACCGTTACTGAGATTTTACCGAATTCGCATTGCGTTGAGGCG
TGAAGTTTCTTAATGCTGTGCCATATGGTTAAGTTGCGTTTCAAGATGGTCCACAAGTATTTT
TGTATTTAAGCAGTGTCAATTCAAGCCTAACTGCTCATAAAAACTACACGGTTTGCTGATATC
AAAAACGATGTTTGAGAAGAGTAAATTTGTGGTTTCGTTTCTGCTTTTACTCCAGCTATTTTG
TGTCCTTGGTGTACATGGAGAAATTGTCATGACCCAAAGTCCATCAACTCTTTCTGCCTCAGT
```

Figure 2D (continued)

```
TGGTGATAGAGTTATCATTACTTGTCAGAGTTCTCAATCTGTGTTCAACAATTACTTGAGCTG
GTACCAACAAAAACCTGGTAGAGCCCCCAAACTGTTAATCTACGATGCATCCAAACTGGCTAG
CGGAGTACCTTCTAGGTTTAGCGGTTCCGGATCAGGTGCAGAATTTACACTGACAATATCCTC
TTTGCAACCAGACGACTTTGCCACATACTATTGCCAAGGTTCGGATTATAGCGGTGGTTGGGA
CTCCGCGTTTGGTCAAGGTACCAAGTTGACTGTTCTCGGTGGAGGTGGAGGTTCTGGTGGTGG
AGGATCAGGTGGTGGCGGATCTGGCGGTGGAGGGTCCGAGGTGCAGTTGGTAGAGTCGGGCGG
TGGATCAGTCCAGCCTGGTGGATCCTTGAGACTTTCCTGTACCGCTTCTGGTATCGACTTATC
CAGTTATCCCATGTCGTGGGTTAGACAAGCTCCGGGAAAGGGTTTGGAATGGGTTGGTATCAT
CAGCACTAGAGGAAATACTTACTACGCTACTTGGGCTAAGGGACGTTTTACAATTAGTAGAGA
TACGTCTAAAAACACTGTGTATTTGCAGATGAATTCACTAAGAGCCGAGGACACTGCAACTTA
CTACTGTGCACGTGGTCTTTACGGTAATAACTATTATGGAGCTTTCAATTTGTGGGGACAAGG
CACAACTGTAACGGTGTCCTCATAATAAGCGGCCGCAGCGAATTTCTTATGATTTATGATTTT
TATTATTAAATAAGTTATAAAAAAATAAGTGTATACAAATTTTAAAGTGACTCTTAGGTTTT
AAAACGAAAATTCTTATTCTTGAGTAACTCTTTCCTGTAGGTCAGGTTGCTTTCTCAGGTATA
GCATGAGGTCGCTCTTATTGACCACACCTCTACCGGCATGCCGAGCAAATGCCTGCAAATCGC
TCCCCATTTCACCCAATTGTAGATATGCTAACTCCAGCAATGAGTTGATGAATCTCGGTGTGT
ATTTTATGTCCTCAGAGGACAAGGATCCCTTGCCAACAGGGAGTTCTTCAGAGACATGGAGGC
TCAAAACGAAATTATTGACAGCCTAGACATCAATAGTCATACAACAGAAAGCGACCACCCAAC
TTTGGCTGATAATAGCGTATAAACAATGCATACTTTGTACGTTCAAAATACAATGCAGTAGAT
ATATTTATGCATATTACATATAATACATATCACATAGGAAGCAACAGGCGCGTTGGACTTTTA
ATTTTCGAGGACCGCGAATCCTTACATCACACCCAATCCCCCACAAGTGATCCCCCACACACC
ATAGCTTCAAAATGTTTCTACTCCTTTTTTACTCTTCCAGATTTTCTCGGACTCCGCGCATCG
CCGTACCACTTCAAAACACCCAAGCACAGCATACTAAATTTCCCCTCTTTCTTCCTCTAGGGT
GTCGTTAATTACCCGTACTAAAGGTTTGGAAAAGAAAAAGAGACCGCCTCGTTTCTTTTTCT
TCGTCGAAAAAGGCAATAAAAATTTTTATCACGTTTCTTTTTCTTGAAAATTTTTTTTTTGA
TTTTTTTCTCTTTCGATGACCTCCCATTGATATTTAAGTTAATAAACGGTCTTCAATTTCTCA
AGTTTCAGTTTCATTTTTCTTGTTCTATTACAACTTTTTTTACTTCTTGCTCATTAGAAAGAA
AGCATAGCAATCTAATCTAAGTTTTAATTACAAAACTAGTCAAAACGATGAGATTTCCTTCAA
TTTTTACTGCTGTTTTATTCGCAGCATCCTCCGCATTAGCTGAAATTGTCATGACCCAAAGCC
CATCCACTCTGTCTGCTTCCGTTGGTGACCGTGTTATCATAACATGTCAGTCAAGCCAATCGG
TTTTCAATAACTATCTATCATGGTATCAACAAAAACCTGGACGTGCACCAAAGTTACTTATCT
ACGATGCTAGTAAACTGGCAAGTGGAGTACCTTCGAGATTCAGCGGCTCCGGTTCTGGTGCTG
AATTCACATTGACGATTTCCAGTCTACAACCAGATGACTTTGCTACTTACTACTGCCAAGGTT
CAGACTATTCCGGAGGATGGGACTCCGCATTTGGTCAGGGAACAAAATTGACTGTGTTAGGTG
GGGGCGGAGGTAGCGGTGGAGGTGGTTCGGGAGGTGGCGGTTCCGGTGGTGGTGGTTCCGAAG
TGCAGTTGGTTGAGTCTGGTGGAGGTTCTGTCCAACCCGGAGGATCCCTTAGATTGTCATGTA
CAGCCTCTGGTATTGATTTGTCTAGTTACCCAATGTCATGGGTTAGGCAGGCCCCTGGTAAGG
GACTGGAGTGGGTAGGTATTATCTAACTAGAGGCAATACTTATTACGCAACGTGGGCAAAGG
GTAGATTTACCATCTCTAGGGATACCTCCAAAAACACAGTCTATCTGCAAATGAATAGCTTGA
GAGCTGAGGATACTGCTACATATTACTGTGCCCGTGGATTGTATGGTAACAATTACTACGGTG
CTTTCAATCTCTGGGGTCAAGGTACAACTGTGACTGTTTCATCTTAATAGGAGCTCTCAAGAG
GATGTCAGAATGCCATTTGCCTGAGAGATGCAGGCTTCATTTTTGATACTTTTTATTTGTAA
CCTATATAGTATAGGATTTTTTTTGTCATTTTGTTTCTTCTCGTACGAGCTTGCTCCTGATCA
GCCTATCTCGCAGCAGATGAATATCTTGTGGTAGGGGTTTGGGAAAATCATTCGAGTTTGATG
TTTTTCTTGGTATTTCCCACTCCTCTTCAGAGTACAGAAGATTAAGTGAGACCTTCGTTTGTG
CCTTCAGTAATGTCTTGTTTCTTTTGTTGCAGTGGTGAGCCATTTTGACTTCGTGAAAGTTTC
TTTAGAATAGTTGTTTCCAGAGGCCAAACATTCCACCCGTAGTAAAGTGCAAGCGTAGGAAGA
CCAAGACTGGCATAAATCAGGTATAAGTGTCGAGCACTGGCAGGTGATCTTCTGAAAGTTTCT
```

Figure 2D (continued)

ACTAGCAGATAAGATCCAGTAGTCATGCATATGGCAACAATGTACCGTGTGGATCTAAGAACG
CGTCCTACTAACCTTCGCATTCGTTGGTCCAGTTTGTTGTTATCGATCAACGTGACAAGGTTG
TCGATTCCGCGTAAGCATGCATACCCAAGGACGCCTGTTGCAATTCCAAGTGAGCCAGTTCCA
ACAATCTTTGTAATATTAGAGCACTTCATTGTGTTGCGCTTGAAAGTAAAATGCGAACAAATT
AAGAGATAATCTCGAAACCGCGACTTCAAACGCCAATATGATGTGCGGCACACAATAAGCGTT
CATATCCGCTGGGTGACTTTCTCGCTTTAAAAAATTATCCGAAAAAATTTTCTAGAGTGTTGA
CACTTTATACTTCCGGCTCGTATAATACGACAAGGTGTAAGGAGGACTAAACCATGGCTAAAC
TCACCTCTGCTGTTCCAGTCCTGACTGCTCGTGATGTTGCTGGTGCTGTTGAGTTCTGGACTG
ATAGACTCGGTTTCTCCCGTGACTTCGTAGAGGACGACTTTGCCGGTGTTGTACGTGACGACG
TTACCCTGTTCATCTCCGCAGTTCAGGACCAGGTTGTGCCAGACAACACTCTGGCATGGGTAT
GGGTTCGTGGTCTGGACGAACTGTACGCTGAGTGGTCTGAGGTCGTGTCTACCAACTTCCGTG
ATGCATCTGGTCCAGCTATGACCGAGATCGGTGAACAGCCCTGGGGTCGTGAGTTTGCACTGC
GTGATCCAGCTGGTAACTGCGTGCATTTCGTCGCAGAAGAGCAGGACTAACCTCTAGGACACC
TTACGATTATTTAGAGAGTATTTATTAGTTTTATTGTATGTATACGGATGTTTTATTATCTAT
TTATGCCCTTATATTCTGTAACTATCCAAAAGTCCTATCTTATCAAGCCAGCAATCTATGTCC
GCGAACGTCAACTAAAAATAAGCTTTTTATGCTCTTCTCTCTTTTTTTCCCTTCGGTATAATT
ATACCTTGCATCCACAGATTCTCCTGCCAAATTTTGCATAATCCTTTACAACATGGCTATATG
GGAGCACTTAGCGCCCTCCAAAACCCATATTGCCTACGCATGTATAGGTGTTTTTTCCACAAT
ATTTTCTCTGTGCTCTCTTTTTATTAAAGAGAAGCTCTATATCGGAGAAGCTTCTGTGGCCGT
TATATTCGGCCTTATCGTGGGACCACATTGCCTGAATTGGTTTGCCCCGGAAGATTGGGGAAA
CTTGGATCTGATTACCTTAGCTGCAGGTACCACTGAGCGTCAGACCCCGTAGAAAAGATCAAA
GGATCTTCTTGAGATCCTTTTTTTCTGCGCGTAATCTGCTGCTTGCAAACAAAAAAACCACCG
CTACCAGCGGTGGTTTGTTTGCCGGATCAAGAGCTACCAACTCTTTTTCCGAAGGTAACTGGC
TTCAGCAGAGCGCAGATACCAAATACTGTTCTTCTAGTGTAGCCGTAGTTAGGCCACCACTTC
AAGAACTCTGTAGCACCGCCTACATACCTCGCTCTGCTAATCCTGTTACCAGTGGCTGCTGCC
AGTGGCGATAAGTCGTGTCTTACCGGGTTGGACTCAAGACGATAGTTACCGGATAAGGCGCAG
CGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGA
TGCTCGTCAGGGGGCGGAGCCTATGGAAAAACGCCAGCAACGCGGCCTTTTTACGGTTCCTG
GCCTTTTGCTGGCCTTTTGCTCACATCG

Figure 3:

Vector for expression in mammalian cells, each vector with one GOI (fusion protein of constant antibody region with TNF-receptor 2 binding domain = Etanercept)

Figure 3A: mammalian vector pNT-MG001 (SEQ-ID NO.: 5)

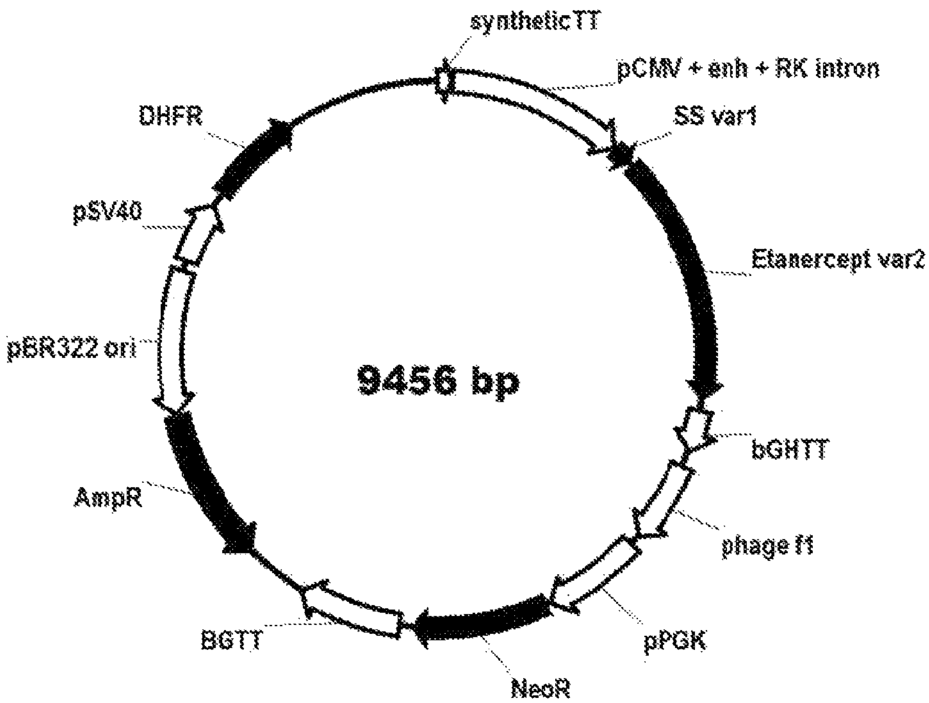

Figure 3B: mammalian vector pNT-MG002 (SEQ-ID NO.: 6)

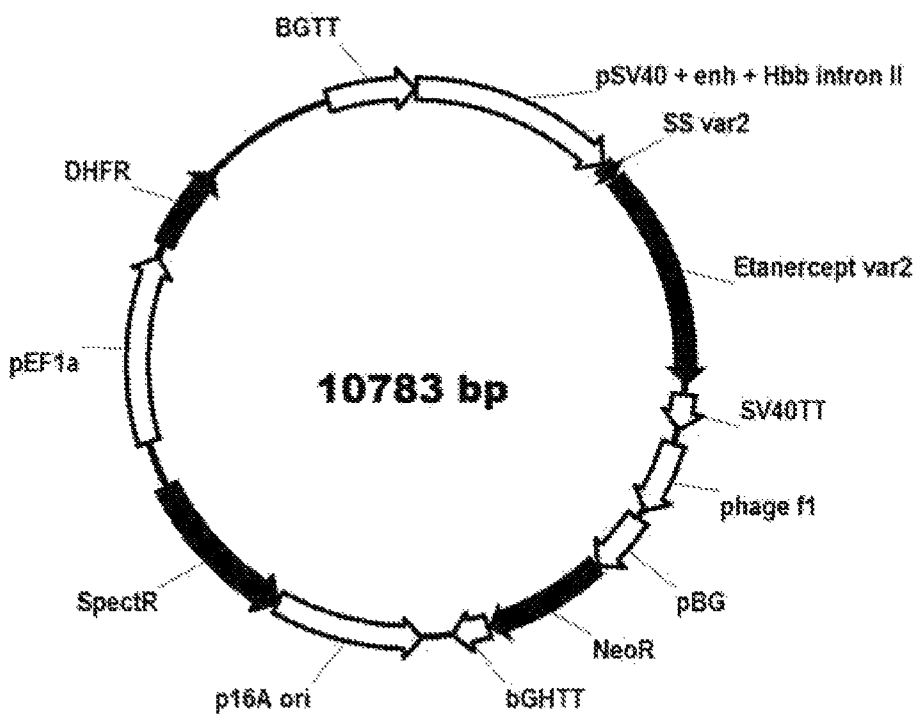

Figure 3C: mammalian vector pNT-MG003 (SEQ-ID NO.: 7)
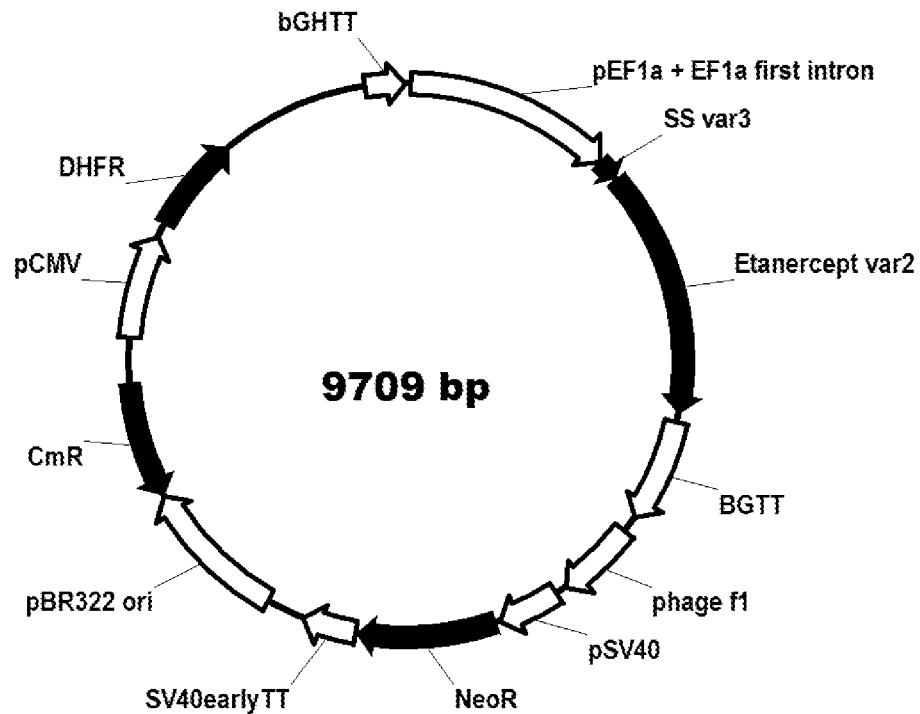
Figure 3D: mammalian vector pNT-MG004 (SEQ-ID NO.: 8)
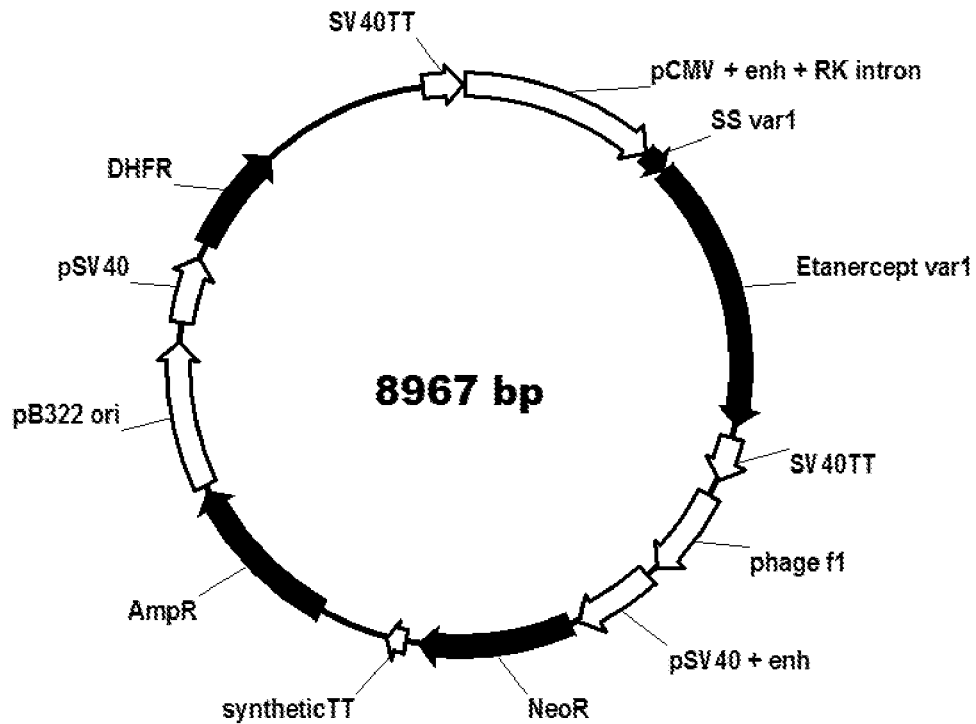

Figure 4:

Sequences of the mammalian vectors of Fig. 3A to Fig. 3D:

Figure 4A: pNT_MG001 (SEQ-ID NO: 5)

```
AATTCGGATCTAATAAAATATCTTTATTTTCATTACATCTGTGTGTTGGTTTTTTGTGTGGAT
CTTCAATATTGGCCATTAGCCATATTATTCATTGGTTATATAGCATAAATCAATATTGGCTAT
TGGCCATTGCATACGTTGTATCTATATCATAATATGTACATTTATATTGGCTCATGTCCAATA
TGACCGCCATGTTGGCATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGA
CCGCCCAACGACCCCGCCCATTGACGTCAATAATGACGTATGTTCCCATAGTAACGCCAATA
GGGACTTTCCATTGACGTCAATGGGTGGAGTATTTACGGTAAACTGCCCACTTGGCAGTACAT
CAAGTGTATCATATGCCAAGTACGCCCCCTATTGACGTCAATGACGGTAAATGGCCCGCCTGG
CATTATGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAAAAT
CAACGGGACTTTCCAAAATGTCGTAACAACTCCGCCCCATTGACGCAAATGGGCGGTAGGCGT
GTACGGTGGGAGGTCTATATAAGCAGAGCTCGTTTAGTGAACCGTCAGATCGCCTGGAGACGC
CATCCACGCTGTTTTGACCTCCATAGAAGACACCGGGACCGATCCAGCCTCCGCGGCCGGGAA
CGGTGCATTGGAACGCGGATTCCCCGTGCCAAGAGTGACGTAAGTACCGCCTATAGAGTCTAT
AGGCCCACCCCCTTGGCTTCGTTAGAACGCGGCTACAATTAATACATAACCTTATGTATCATA
CACATACGATTTAGGTGACACTATAGAATAACATCCACTTTGCCTTTCTCTCCACAGGTGTCC
ACTCCCAGGTCCAACTGCACCTCGGTTCTATCGAAAACGCGCCTCTAGACCTGCAGGCCACCA
TGGCCCCCGTGGCCGTGTGGGCCGCCCTGGCCGTGGGCCTGGAGCTGTGGGCCGCCGCCCACG
CCCTGCCCGCCCAGGTGGCCTTCACCCCCTACGCCCCCGAGCCCGGCTCCACCTGCCGGCTGC
GGGAGTACTACGACCAGACCGCCCAGATGTGCTGCTCCAAGTGCTCCCCCGGCCAGCACGCCA
AGGTGTTCTGCACCAAGACCTCCGACACCGTGTGCGACTCCTGCGAGGACTCCACCTACACCC
AGCTGTGGAACTGGGTGCCCGAGTGCCTGTCCTGCGGCTCCCGGTGCTCCTCCGACCAGGTGG
AGACCCAGGCCTGCACCCGGGAGCAGAACCGGATCTGCACCTGCCGGCCCGGCTGGTACTGCG
CCCTGTCCAAGCAGGAGGGCTGCCGGCTGTGCGCCCCCCTGCGGAAGTGCCGGCCCGGCTTCG
GCGTGGCCCGGCCCGGCACCGAGACCTCCGACGTGGTGTGCAAGCCCTGCGCCCCCGGCACCT
TCTCCAACACCACCTCCTCCACCGACATCTGCCGGCCCCACCAGATCTGCAACGTGGTGGCCA
TCCCCGGCAACGCCTCCATGGACGCCGTGTGCACCTCCACCTCCCCCACCCGGTCCATGGCCC
CCGGCGCCGTGCACCTGCCCCAGCCCGTGTCCACCCGGTCCCAGCACACCCAGCCCACCCCCG
AGCCCTCCACCGCCCCCTCCACCTCCTTCCTGCTGCCCATGGGCCCCTCCCCCCCGCCGAGG
GCTCCACCGGCGACGAGCCCAAGTCCTGCGACAAGACCCACACCTGCCCCCCCTGCCCCGCCC
CCGAGCTGCTGGGCGGCCCCTCCGTGTTCCTGTTCCCCCCAAGCCCAAGGACACCCTGATGA
TCTCCCGGACCCCCGAGGTGACCTGCGTGGTGGTGGACGTGTCCCACGAGGACCCCGAGGTGA
AGTTCAACTGGTACGTGGACGGCGTGGAGGTGCACAACGCCAAGACCAAGCCCCGGGAGGAGC
AGTACAACTCCACCTACCGGGTGGTGTCCGTGCTGACCGTGCTGCACCAGGACTGGCTGAACG
GCAAGGAGTACAAGTGCAAGGTGTCCAACAAGGCCCTGCCCGCCCCCATCGAGAAGACCATCT
CCAAGGCCAAGGGCCAGCCCCGGGAGCCCCAGGTGTACACCCTGCCCCCCTCCCGGGAGGAGA
TGACCAAGAACCAGGTGTCCCTGACCTGCCTGGTGAAGGGCTTCTACCCCTCCGACATCGCCG
TGGAGTGGGAGTCCAACGGCCAGCCCGAGAACAACTACAAGACCACCCCCCCGTGCTGGACT
CCGACGGCTCCTTCTTCCTGTACTCCAAGCTGACCGTGGACAAGTCCCGGTGGCAGCAGGGCA
ACGTGTTCTCCTGCTCCGTGATGCACGAGGCCCTGCACAACCACTACACCCAGAAGTCCCTGT
```

Figure 4A (continued)

```
CCCTGTCCCCCGGCAAGTGATGAGGCGCGCCCCTAGAGTCGACCCGGGCGGCCGCTTCCCTTT
AGTGAGGGTTAATGCTTCGAGCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTCTATGGAAA
TCCGATAAGGATCGATCCGGGCTGGCGTAATAGCGAAGAGGCCCGCACCGATCGCCCTTCCCA
ACAGTTGCGCAGCCTGAATGGCGAATGGACGCGCCCTGTAGCGGCGCATTAAGCGCGGCGGGT
GTGGTGGTTACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCGGGGCTC
CCTTTAGGGTTCCGATTTAGAGCTTTACGGCACCTCGACCGCAAAAAACTTGATTTGGGTGAT
GGTTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGTCTATTCT
TTTGATTTATAAGGGATTTTGCCGATTTCGGCCTATTGGTTAAAAAATGAGCTGATTTAACAA
ATATTTAACGCGAATTTTAACAAAATATTAACGTTTACAATTTCGCCTGATGCGGTATTTTCT
CCTTACGCATCTGTGCGGTATTTCACACCGCATACGCGGATCTTTGGGGTTGCGCCTTTTCCA
AGGCAGCCCTGGGTTTGCGCAGGGACGCGGCTGCTCTGGGCGTGGTTCCGGGAAACGCAGCGG
CGCCGACCCTGGGTCTCGCACATTCTTCACGTCCGTTCGCAGCGTCACCCGGATCTTCGCCGC
TACCCTTGTGGGCCCCCGGCGACGCTTCCTGCTCCGCCCCTAAGTCGGGAAGGTTCCTTGCG
GTTCGCGGCGTGCCGGACGTGACAAACGGAAGCCGCACGTCTCACTAGTACCCTCGCAGACGG
ACAGCGCCAGGGAGCAATGGCAGCGCGCCGACCGCGATGGGCTGTGGCCAATAGCGGCTGCTC
AGCAGGGCGCGCCGAGAGCAGCGGCCGGGAAGGGGCGGTGCGGGAGGCGGGGTGTGGGCGGT
AGTGTGGGCCCTGTTCCTGCCCGCGCGGTGTTCCGCATTCTGCAAGCCTCCGGAGCGCACGTC
GGCAGTCGGCTCCCTCGTTGACCGAATCACCGACCTCTCTCCCCAGGGGGATCCACCGGAGCT
TACCATGACCGAGTACAAGCCCACGGTGCGCGCTAGCGCTACCGGTCGCCACCATGATTGAAC
AAGATGGATTGCACGCAGGTTCTCCGGCCGCTTGGGTGGAGAGGCTATTCGGCTATGACTGGG
CACAACAGACAATCGGCTGCTCTGATGCCGCCGTGTTCCGGCTGTCAGCGCAGGGGCGCCCGG
TTCTTTTTGTCAAGACCGACCTGTCCGGTGCCCTGAATGAACTGCAGGACGAGGCAGCGCGGC
TATCGTGGCTGGCCACGACGGGCGTTCCTTGCGCAGCTGTGCTCGACGTTGTCACTGAAGCGG
GAAGGGACTGGCTGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGCTTGATCCGGCTA
CCTGCCCATTCGACCACCAAGCGAAACATCGCATCGAGCGAGCACGTACTCGGATGGAAGCCG
GTCTTGTCGATCAGGATGATCTGGACGAAGAGCATCAGGGGCTCGCGCCAGCCGAACTGTTCG
CCAGGCTCAAGGCGCGCATGCCCGACGGCGAGGATCTCGTCGTGACCCATGGCGATGCCTGCT
TGCCGAATATCATGGTGGAAAATGGCCGCTTTTCTGGATTCATCGACTGTGGCCGGCTGGGTG
TGGCGGACCGCTATCAGGACATAGCGTTGGCTACCCGTGATATTGCTGAAGAGCTTGGCGGCG
AATGGGCTGACCGCTTCCTCGTGCTTTACGGTATCGCCGCTCCCGATTCGCAGCGCATCGCCT
TCTATCGCCTTCTTGACGAGTTCTTCTGAGCGGGACTCTGGGGTTCGAAATGACCGACCAAGC
GACGCCCAACCTGCCATCACGATGGCCGCGATGAGTCGACCCGGGCGGCCGCTTCCCTTTAGT
GAGGGTTAATGCTTCGAGACTCCTCAGGTGCAGGCTGCCTATCAGAAGGTGGTGGCTGGTGTG
GCCAATGCCCTGGCTCACAAATACCACTGAGATCTTTTTCCCTCTGCCAAAAATTATGGGGAC
ATCATGAAGCCCCTTGAGCATCTGACTTCTGGCTAATAAAGGAAATTTATTTTCATTGCAATA
GTGTGTTGGAATTTTTTGTGTCTCTCACTCGGAAGGACATATGGGAGGGCAAATCATTTAAAA
CATCAGAATGAGTATTTGGTTTAGAGTTTGGCAACATATGCCCATATGCTGGCTGCCATGAAC
AAAGGTTGGCTATAAAGAGGTCATCAGTATATGAAACAGCCCCCTGCTGTCCATTCCTTATTC
CATAGAAAAGCCTTGACTTGAGGTTAGATTTTTTTATATTTTGTTTTGTGTTATTTTTTTCT
TTAACATCCCTAAAATTTTCCTTACATGTTTTACTAGCCAGATTTTTCCTCCTCTCCTGACTA
CTCCCAGTCATAGCTGTCCCTCTTCTCTTATGGAGATCCCTCGACAATCGATAGCGATAAGGA
TCCGCGTATGGTGCACTCTCAGTACAATCTGCTCTGATGCCGCATAGTTAAGCCAGCCCCGAC
```

Figure 4A (continued)

```
ACCCGCCAACACCCGCTGACGCGCCCTGACGGGCTTGTCTGCTCCCGGCATCCGCTTACAGAC
AAGCTGTGACCGTCTCCGGGAGCTGCATGTGTCAGAGGTTTTCACCGTCATCACCGAAACGCG
CGAGACGAAAGGGCCTCGTGATACGCCTATTTTTATAGGTTAATGTCATGATAATAATGGTTT
CTTAGACGTCAGGTGGCACTTTTCGGGGAAATGTGCGCGGAACCCCTATTTGTTTATTTTTCT
AAATACATTCAAATATGTATCCGCTTACCAATGCTTAATCAGTGAGGCACCTATCTCAGCGAT
CTGTCTATTTCGTTCATCCATAGTTGCCTGACTCCCCGTCGTGTAGATAACTACGATACGGGA
GGGCTTACCATCTGGCCCCAGTGCTGCAATGATACCGCGGGACCCACGCTCACCGGCTCCAGA
TTTATCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGTATGGC
TTCATTCAGCTCCGGTTCCCAACGATCAAGGCGAGTTACATGATCCCCATGTTGTGCAAAAA
AGCGGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCGAGTTGCTCTTG
CCCGGCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGATGTA
ACCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAAAGT
GCCACCTGTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCAAAC
AAAAAAACCACCGCTACCAGCGGTGGTTTGTTTGCCGGATCAAGAGCTACCAACTCTTTTTCC
GAAGGTAACTGGCTTCAGCAGAGCGCAGATACCAAATACTGTTCTTCTAGTGTAGCCGTAGTT
AGGCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCTCTGACTTGAGCG
TCGATTTTTGTGATGCTCGTCAGGGGGCGGAGCCTATGGAAAAACGCCAGCAACGCGGGCTC
GACAGATCCATTTAAATTTTCACCGTCATCACCGAAACGCGCGAGGCAGCTGTGGAATGTGTG
TCAGTTAGGGTGTGGAAAGTCCCCAGGCTCCCCAGCAGGCAGAAGTATGCAAAGCATGCATCT
CAATTAGTCAGCAACCAGGTGTGGAAAGTCCCCAGGCTCCCCAGCAGGCAGAAGTATGCAAAG
CATGCATCTCAATTAGTCAGCAACCATAGTCCCGCCCCTAACTCCGCCCATCCCGCCCCTAAC
TCCGCCCAGTTCCGCCCATTCTCCGCCCCATGGCTGACTAATTTTTTTATTTATGCAGAGGC
CGAGGCCGCCTCGGCCCTCTGAGCTATTCCAGAAGTAGTGAGGAGGCTTTTTTGGAGGCCTAG
GCTTTTGCAAAAAGCTAATTCGAGCTCGGTACCCCAAACTTGACGGCAATCCTAGCGTGAAG
GCTGGTAGGATTTTATCCCCGCTGCCATCATGGTTCGACCATTGAACTGCATCGTCGCCGTGT
CCCAAAATATGGGGATTGGCAAGAACGGAGACCGACCCTGGCCTCCGCTCAGGAACGAGTTCA
AGTACTTCCAAAGAATGACCACAACCTCTTCAGTGGAAGGTAAACAGAATCTGGTGATTATGG
GTAGGAAAACCTGGTTCTCCATTCCTGAGAAGAATCGACCTTTAAAGGACAGAATTAATATAG
TTCTCAGTAGAGAACTCAAAGAACCACCACGAGGAGCTCATTTTCTTGCCAAAAGTTTGGATG
ATGCCTTAAGACTTATTGAACAACCGGAATTGGCAAGTAAAGTAGACATGGTTTGGATAGTCG
GAGGCAGTTCTGTTTACCAGGAAGCCATGAATCAACCAGGCCACCTCAGACTCTTTGTGACAA
GGATCATGCAGGAATTTGAAAGTGACACGTTTTTCCCAGAAATTGATTTGGGGAAATATAAAC
TTCTCCCAGAATACCCAGGCGTCCTCTCTGAGGTCCAGGAGGAAAAAGGCATCAAGTATAAGT
TTGAAGTCTACGAAGAAAGACTAACAGGAAGATGCTTTCAAGTTCTCTGCTCCCTCCTAA
```

Figure 4A (continued)

```
AGCTATGCATTTTTATAAGACCATGGGGGATGCTCGATCCCCTCGCGAGTTGGTTCAGCTGCT
GCCTGAGGCTGGACGACCTCGCGGAGTTCTACCGGCAGTGCAAATCCGTCGGCATCCAGGAAA
CCAGCAGCGGCTATCCGCGCATCCATGCCCCGAACTGCAGGAGTGGGGAGGCACGATGGCCG
CTTTGGTCCGGATCTTTGTGAAGGAACCTTACTTCTGTGGTGTGACATAATTGGACAAACTAC
CTACAGAGATTTAAAGCTCTAAGGTAAATATAAAATTTTTAAGTGTATAATGTGTTAAACTAC
TGATTCTAATTGTTTGTGTATTTTAGATTCCAACCTATGGAACTGATGAATGGGAGCAGTGGT
GGAATGCCTTTAATGAGGAAAACCTGTTTTGCTCAGAAGAAATGCCATCAGTGATGATGAGG
CTACTGCTGACTCTCAACATTCTACTCCTCCAAAAAGAAGAGAAAGGTAGAAGACCCCAAGG
ACTTTCCTTCAGAATTGCTAAGTTTTTTGAGTCATGCTGTGTTTAGTAATAGAACTCTTGCTT
GCTTTGCTATTTACACCACAAAGGAAAAGCTGCACTGCTATACAAGAAAATTATGGAAAAAT
ATTCTGTAACCTTTATAAGTAGGCATAACAGTTATAATCATAACATACTGTTTTTTCTTACTC
CACACAGGCATAGAGTGTCTGCTATTAATAACTATGCTCAAAAATTGTGTACCTTTAGCTTTT
TAATTTGTAAAGGGGTTAATAAGGAATATTTGATGTATAGTGCCTTGACTAGAGATCATAATC
AGCCAG
```

Figure 4B: pNT_MG002 (SEQ-ID NO. 6)

```
AATTCGGATCTGCGCAGCACCATGGCCTGAAATAACCTCTGAAAGAGGAACTTGGTTAGGTAC
CTTCTGAGGCGGAAAGAACCAGCTGTGGAATGTGTGTCAGTTAGGGTGTGGAAAGTCCCCAGG
CTCCCCAGCAGGCAGAAGTATGCAAAGCATGCATCTCAATTAGTCAGCAACCAGGTGTGGAAA
GTCCCCAGGCTCCCCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCGCCCATTCTCCGCC
CCATGGCTGACTAATTTTTTTATTTATGCAGAGGCCGAGGCCGCCTCGGCCTCTGAGCTATT
CCAGAAGTAGTGAGGAGGCTTTTTGGAGGCCTAGGCTTTTGCAAAAGCTTCTCGAGGAACT
TCAGGGTGAGTCTATGGGACCCTTGATGTTTTCTTTCCCCTTCTTTTCTATGGTTAAGTTCAT
GTCATAGGAAGGGGAGAAGTAACAGGGTACAGTTTAGAATGGGAAACAGACGAATGATTGCAT
CAGTGTGGAAGTCTCAGGATCGTTTTAGTTTCTTTTATTTGCTGTTCATAACAATTGTTTTCT
TTTGTTTAATTCTTGCTTTCTTTTTTTTCTTCTCCGCAATTTTTACTATTATACTTAATGCC
TTAACATTGTGTATAACAAAAGGAAATATCTCTGAGATACATTAAGTAACTTAAAAAAAAACT
TTACACAGTCTGCCTAGTACATTACTATTTGGAATATATGTGTGCTTATTTGCATATTCATAA
TCTCCCTACTTTATTTTCTTTTATTTTTAATTGATACATAATCATTATACATATTTATGGGTT
AAAGTGTAATGTTTTAATATGTGTACACATATTGACCAAATCAGGGTAATTTTGCATTTGTAA
TTTTAAAAAATGCTTTCTTCTTTTAATATACTTTTTTGTTTATCTTATTTCTAATACTTTCCC
TAATCTCTTTCTTTCAGGGCAATAATGATACAATGTATCATGCCTCTTTGCACCATTCTAAAG
AATAACAGTGATAATTTCTGGGTTAAGGCAATAGCAATATTTCTGCATATAAATATTTCTGCA
TATAAATTGTAACTGATGTAAGAGGTTTCATATTGCTAATAGCAGCTACAATCCAGCTACCAT
TCTGCTTTTATTTTATGGTTGGGATAAGGCTGGATTATTCTGAGTCCAAGCTAGGCCCTTTTG
CTAATCATGTTCATACCTCTTATCTTCCTCCCACAGCTCCTGGGCAGTGTCCACTCCCAGGTC
CAACTGCACCTCGGTTCTATCGAAAACGCGTCCACCATGAAGTGGGTGACCTTCATCTCCCTG
CTGTTCCTGTTCTCCTCCGCCTACTCCCTGCCCGCCCAGGTGGCCTTCACCCCCTACGCCCCC
GAGCCCGGCTCCACCTGCCGGCTGCGGGAGTACTACGACCAGACCGCCCAGATGTGCTGCTCC
AAGTGCTCCCCGGCCAGCACGCCAAGGTGTTCTGCACCAAGACCTCCGACACCGTGTGCGAC
TCCTGCGAGGACTCCACCTACACCCAGCTGTGGAACTGGGTGCCCGAGTGCCTGTCCTGCGGC
TCCCGGTGCTCCTCCGACCAGGTGGAGACCCAGGCCTGCACCCGGGAGCAGAACCGGATCTGC
ACCTGCCGGCCCGGCTGGTACTGCGCCCTGTCCAAGCAGGAGGGCTGCCGGCTGTGCGCCCCC
CTGCGGAAGTGCCGGCCCGGCTTCGGCGTGGCCCGGCCCGGCACCGAGACCTCCGACGTGGTG
```

Figure 4B (continued)

```
TGCAAGCCCTGCGCCCCGGCACCTTCTCCAACACCACCTCCTCCACCGACATCTGCCGGCCC
CACCAGATCTGCAACGTGGTGGCCATCCCCGGCAACGCCTCCATGGACGCCGTGTGCACCTCC
ACCTCCCCCACCCGGTCCATGGCCCCCGGCGCCGTGCACCTGCCCCAGCCCGTGTCCACCCGG
TCCCAGCACACCCAGCCCACCCCCGAGCCCTCCACCGCCCCCTCCACCTCCTTCCTGCTGCCC
ATGGGCCCCTCCCCCCCGCCGAGGGCTCCACCGGCGACGAGCCCAAGTCCTGCGACAAGACC
CACACCTGCCCCCCCTGCCCCGCCCCCGAGCTGCTGGGCGGCCCCTCCGTGTTCCTGTTCCCC
CCCAAGCCCAAGGACACCCTGATGATCTCCCGGACCCCCGAGGTGACCTGCGTGGTGGTGGAC
GTGTCCCACGAGGACCCCGAGGTGAAGTTCAACTGGTACGTGGACGGCGTGGAGGTGCACAAC
GCCAAGACCAAGCCCCGGGAGGAGCAGTACAACTCCACCTACCGGGTGGTGTCCGTGCTGACC
GTGCTGCACCAGGACTGGCTGAACGGCAAGGAGTACAAGTGCAAGGTGTCCAACAAGGCCCTG
CCCGCCCCCATCGAGAAGACCATCTCCAAGGCCAAGGGCCAGCCCCGGGAGCCCCAGGTGTAC
ACCCTGCCCCCCTCCCGGGAGGAGATGACCAAGAACCAGGTGTCCCTGACCTGCCTGGTGAAG
GGCTTCTACCCCTCCGACATCGCCGTGGAGTGGGAGTCCAACGGCCAGCCCGAGAACAACTAC
AAGACCACCCCCCCCGTGCTGGACTCCGACGGCTCCTTCTTCCTGTACTCCAAGCTGACCGTG
GACAAGTCCCGGTGGCAGCAGGGCAACGTGTTCTCCTGCTCCGTGATGCACGAGGCCCTGCAC
AACCACTACACCCAGAAGTCCCTGTCCCTGTCCCCGGCAAGTGATGAGGCGCGCCCCTAGAG
TCGACCCGGGCGGCCGCTTCCCTTTAGTGAGGGTTAATGCTTCGAGCAGACATGATAAGATAC
ATTGATGAGTTTGGACAAACCACAACTAGAATGCAGTGAAAAAAATGCTTTATTTGTGAAATT
TGTGATGCTATTGCTTTATTTGTAACCATTATAAGCTGCAATAAACAAGTTAACAACAACAAT
TGCATTCATTTTATGTTTCAGGTTCAGGGGGAGATGTGGGAGGTTTTTTAAAGCAAGTAAAAC
CTCTACAAATGTGGTAAAATCCGATAAGGATCGATCCGGGCTGGCGTAATAGCGAAGAGGCCC
GCACCGATCGCCCTTCCCAACAGTTGCGCAGCCTGAATGGCGAATGGAACGCGCCCTGTAGCG
GCGCATTAAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGAGCTTTACGGCACCTCGACCGCA
AAAAACTTGATTTGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAA
AAAATGAGCTGATTTAACAAATATTTAACGCGAATTTTAACAAAATATTAACGTTTACAATTT
CGCCTGATGCGGTATTTTCTCCTTACGCATCTGTGCGGTATTTCACACCGCATACGCGGATCT
GCTTTGCTTCTCAATTTCTTATTTGCATAATGAGAAAAAAAGGAAAATTAATTTTAACACCAA
TTCAGTAGTTGATTGAGCAAATGCGTTGCCAAAAAGGATGCTTTAGAGACAGTGTTCTCTGCA
CAGATAAGGACAAACATTATTCAGAGGGAGTACCCAGAGCTGAGACTCCTAAGCCAGTGAGTG
GCACAGCATTCTAGGGAGAAATATGCTTGTCATCACCGAAGCCTGATTCCGTAGAGCCACACC
TTGGTAAGGGCCAATCTGCTCACACAGGATAGAGAGGGCAGGAGCCAGGGCAGAGCATATAAG
GTGAGGTAGGATCAGTTGCTCCTCACATTTGCTTCTGACATAGTTGTGTTGGCTAGCGCTACC
GGTCGCCACCATGATTGAACAAGATGGATTGCACGCAGGTTCTCCGGCCGCTTGGGTGGAGAG
GCTATTCGGCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTGAATGAACT
GCAGGACGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGCAGGATCT
CCTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAGC
ACGTACTCGGATGGAAGCCGGTCTTGTCGATCAGGATGATCTGGACGAAGAGCATCAGGGGCT
CGCGCCAGCCGAACTGTTCGCCAGGCTCAAGGCGCGCATGCCCGACGGCGAGGATCTCGTCGT
GACCCATGGCGATGCCTGCTTGCCGAATATCATGGTGGAAAATGGCCGCTTTTCTGGATTCAT
CGACTGTGGCCGGCTGGGTGTGGCGGACCGCTATCAGGACATAGCGTTGGCTACCCGTGATAT
TGCTGAAGAGCTTGGCGGCGAATGGGCTGACCGCTTCCTCGTGCTTTACGGTATCGCCGCTCC
```

Figure 4B (continued)

```
CGATTCGCAGCGCATCGCCTTCTATCGCCTTCTTGACGAGTTCTTCTGACGACTGTGCCTTCT
AGTTGCCAGCCATCTGTTGTTTGCCCCTCCCCGTGCCTTCCTTGACCCTGGAAGGTGCCACT
CCCACTGTCCTTTCCTAATAAAATGAGGAAATTGCATCGCATTGTCTGAGTAGGTGTCATTCT
ATTCTGGGGGTGGGGTGGGGCAGGACAGCAAGGGGGAGGATTGGGAAGACAATAGCAGGCAT
GCTGGGGATGCGGTGGGCTCTATGGAATCGATAGCGATAAGGATCCGCGTATGGTGCACTCTC
GGTTGCCGCCGGGCGTTTTTTATTGGTGAGAATCCAAGCTAGAGGCATCAAATAAAACGAAAG
GCTCAGTCGAAAGACTGGGCCTTTCGTTTTATCTGTTGTTTGTCGGTAACGCTCTCCTGAGT
AGGACAAATCCGCCGCCCTAGACCTAGGGATATATTCCGCTTCCTCGCTCACTGACTCGCTAC
GCTCGGTCGTTCGACTGCGGCGAGCGGAAATGGCTTACGAACGGGGCGGAGATTTCCTGGAAG
ATGCCAGGAAGATACTTAACAGGGAAGTGAGAGGGCCGCGGCAAAGCCGTTTTTCCATAGGCT
CCGCCCCCTGACAAGCATCACGAAATCTGACGCTCAAATCAGTGGTGGCGAAACCCGACAGG
ACTATAAGATACCAGGCGTTTCCCCCTGGCGGCTCCTCGTGCGCTCTCCTGTTCCTGCCTT
TCGGTTTACCGGTGTCATTCCGCTGTTATGGCCGCGTTTGTCTCATTCCACGCCTGACACTCA
GTTCCGGGTAGGCAGTTCGCTCCAAGCTGGACTGTATGCACGAACCCCCGTTCAGTCCGACC
GCTGCGCCTTATCCGGTAACTATCGTCTTGAGTCCAACCCGGAAAGACATGCAAAAGCACCAC
TGGCAGCAGCCACTGGTAATTGATTTAGAGGAGTTAGTCTTGAAGTCATGCGCCGGTTAAGGC
TAAACTGAAAGGACAAGTTTTGGTGACTGCGCTCCTCCAAGCCAGTTACCTCGGTTCAAAGAG
TTGGTAGCTCAGAGAACCTTCGAAAAACCGCCCTGCAAGGCGGTTTTTTCGTTTTCAGAGCAA
GAGATTACGCGCAGACCAAAACGATCTCAAGAAGATCATCTTATTAATCAGATAAAATATTTC
TAGATTTCAGTGCAATTTATCTCTTCAAATGTAGCACCTGAAGTCAGCCCCATACGATATAAG
TTGTTACTAGTGCTTGGATTCTCACCAATAAAAACGCCCGGCGGCAACCGAGCGTTCTGAAC
AAATCCAGATGGAGTTCTGAGGTCATTACTGGATCTATCAACAGGAGTCCAAGCGAGCTCGAT
ATCCGTCGGCTTGAACGAATTGTTAGACATTATTTGCCGACTACCTTGGTGATCTCGCCTTTC
ACGTAGTGGACAAATTCTTCCAACTGATCTGCGCGCGAGGCCAAGCGATCTTCTTCTTGTCCA
AGATAAGCCTGTCTAGCTTCAAGTATGACGGGCTGATACTGGGCCGGCAGGCGCTCCATTGCC
CAGTCGGCAGCGACATCCTTCGGCGCGATTTTGCCGGTTACTGCGCTGTACCAAATGCGGGAC
AACGTAAGCACTACATTTCGCTCATCGCCAGCCCAGTCGGGCGGCGAGTTCCATAGCGTTAAG
GTTTCATTTAGCGCCTCAAATAGATCCTGTTCAGGAACCGGATCAAAGAGTTCCTCCGCCGCT
GGACCTACCAAGGCAACGCTATGTTCTCTTGCTTTTGTCAGCAAGATAGCCAGATCAATGTCG
ATCGTGGCTGGCTCGAAGATACCTGCAAGAATGTCATTGCGCTGCCATTCTCCAAATTGCAGT
TCGCGCTTAGCTGGATAACGCCACGGAATGATGTCGTCGTGCACAACAATGGTGACTTCTACA
GCGCGGAGAATCTCGCTCTCTCCAGGGGAAGCCGAAGTTTCCAAAAGGTCGTTGATCAAAGCT
CGCCGCGTTGTTTCATCAAGCCTTACGGTCACCGTAACCAGCAAATCAATATCACTGTGTGGC
TTCAGGCCGCCATCCACTGCGGAGCCGTACAAATGTACGGCCAGCAACGTCGGTTCGAGATGG
CGCTCGATGACGCCAACTACCTCTGATAGTTGAGTCGATACTTCGGCGATCACCGCTTCCCTC
ATGATGTTTAACTTTGTTTTAGGGCGACTGCCCTGCTGCGTAACATCGTTGCTGCTCCATAAC
ATCAAACATCGACCCACGGCGTAACGCGCTTGCTGCTTGGATGCCCGAGGCATAGACTGTACC
CCAAAAAAACAGTCATAACAAGCCATGAAAACCGCCACTGCGCCGTTACCACCGCTGCGTTCG
GTCAAGGTTCTGGACCAGTTGCGTGAGCGCATACGCTACTTGCATTACAGCTTACGAACCGAA
CAGGCTTATGTCCACTGGGTTCGTGCCTTCATCCGGATATCGACGTCTGTGTGGAATTGTGAG
CGGATAACAAATTCACACAGGGCCCTCGGACACCGAGGAGAATGTCAAGAGGCGAACACACAA
CGTCTTGGAGCGCCAGAGGAGGAACGAGCTAAAACGGAGCTTTTTGCCCTGCGTGACCAGAT
CCCGGAGTTGGAAAACAATGAAAATGGCTCGACAGATCCATTTAAATTTTCACCGTCATCACC
GAAACGCGCGAGGCAGCTGTGCGTGAGGCTCCGGTGCCCGTCAGTGGGCAGAGCGCACATCGC
CCACAGTCCCCGAGAAGTTGGGGGGAGGGGTCGGCAATTGAACCGGTGCCTAGAGAAGGTGGC
GCGGGGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCAGAA
CACAGGTAAGTGCCGTGTGTGGTTCCCGCGGGCCTGGCCTCTTTACGGGTTATGGCCCTTGCG
```

Figure 4B (continued)

```
TGCCTTGAATTACTTCCACCTGGCTGCAGTACGTGATTCTTGATCCCGAGCTTCGGGTTGGAA
GTGGGTGGGAGAGTTCGAGGCCTTGCGCTTAAGGAGCCCCTTCGCCTCGTGCTTGAGTTGAGG
CCTGGCCTGGGCGCTGGGGCCGCCGCGTGCGAATCTGGTGGCACCTTCGCGCCTGTCTCGCTG
CTTTCGATAAGTCTCTAGCCATTTAAAATTTTTGATGACCTGCTGCGACGCTTTTTTTCTGGC
AAGATAGTCTTGTAAATGCGGCCAAGATCTGCACACTGGTATTTCGGTTTTTGGGGCCGCGG
GCGGCGACGGGGCCCGTGCGTCCCAGCGCACATGTTCGGCGAGGCGGGGCCTGCGAGCGCGGC
CACCGAGAATCGGACGGGGGTAGTCTCAAGCTGGCCGGCCTGCTCTGGTGCCTGGCCTCGCGC
CGCCGTGTATCGCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCGGCGCTCGGGAG
AGCGGGCGGGTGAGTCACCCACACAAAGGAAAAGGGCCTTTCCGTCCTCAGCCGTCGCTTCAT
GTGACTCCACGGAGTACCGGGCGCCGTCCAGGCACCTCGATTAGTTCTCGAGCTTTTGGAGTA
CGTCGTCTTTAGGTTGGGGGGAGGGGTTTTATGCGATGGAGTTTCCCCACACTGAGTGGGTGG
AGACTGAAGTTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTCCATTTCAGG
TGTCGTGAAATTCGAGCTCGGTACCCCAAACTTGACGGCAATCCTAGCGTGAAGGCTGGTAG
GATTTTATCCCCGCTGCCATCATGGTTCGACCATTGAACTGCATCGTCGCCGTGTCCCAAAAT
ATGGGGATTGGCAAGAACGGAGACCGACCCTGGCCTCCGCTCAGGAACGAGTTCAAGTACTTC
CAAAGAATGACCACAACCTCTTCAGTGGAAGGTAAACAGAATCTGGTGATTATGGGTAGGAAA
ACCTGGTTCTCCATTCCTGAGAAGAATCGACCTTTAAAGGACAGAATTAATATAGTTCTCAGT
AGAGAACTCAAAGAACCACCACGAGGAGCTCATTTTCTTGCCAAAAGTTTGGATGATGCCTTA
AGACTTATTGAACAACCGGAATTGGCAAGTAAAGTAGACATGGTTTGGATAGTCGGAGGCAGT
TCTGTTTACCAGGAAGCCATGAATCAACCAGGCCACCTCAGACTCTTTGTGACAAGGATCATG
CAGGAATTTGAAAGTGACACGTTTTTCCCAGAAATTGATTTGGGGAAATATAAACTTCTCCCA
GAATACCCAGGCGTCCTCTCTGAGGTCCAGGAGGAAAAAGGCATCAAGTATAAGTTTGAAGTC
TACGAGAAGAAAGACTAACAGGAAGATGCTTTCAAGTTCTCTGCTCCCTCCTAAAGCTATGC
ATTTTTATAAGACCATGGGGGATGCTCGATCCCCTCGCGAGTTGGTTCAGCTGCTGCCTGAGG
CTGGACGACCTCGCGGAGTTCTACCGGCAGTGCAAATCCGTCGGCATCCAGGAAACCAGCAGC
GGCTATCCGCGCATCCATGCCCCCGAACTGCAGGAGTGGGGAGGCACGATGGCCGCTTTGGTC
CGGATCTTTGTGAAGGAACCTTACTTCTGTGGTGTGACATAATTGGACAAACTACCTACAGAG
ATTTAAAGCTCTAAGGTAAATATAAAATTTTTAAGTGTATAATGTGTTAAACTACTGATTCTA
ATTGTTTGTGTATTTTAGATTCCAACCTATGGAACTGATGAATGGGAGCAGTGGTGGAATGCC
TTTAATGAGGAAAACCTGTTTTGCTCAGAAGAAATGCCATCTAGTGATGATGAGGCTACTGCT
GACTCTCAACATTCTACTCCTCCAAAAAAGAAGAGAAAGGTAGAAGACCCCAAGGACTTTCCT
TCAGAATTGCTAAGTTTTTTGAGTCATGCTGTGTTTAGTAATAGAACTCTTGCTTGCTTTGCT
ATTTACACCACAAAGGAAAAAGCTGCACTGCTATACAAGAAAATTATGGAAAAATATTCTGTA
ACCTTTATAAGTAGGCATAACAGTTATAATCATAACATACTGTTTTTTCTTACTCCACACAGG
CATAGAGTGTCTGCTATTAATAACTATGCTCAAAAATTGTGTACCTTTAGCTTTTTAATTTGT
AAAGGGGTTAATAAGGAATATTTGATGTATAGTGCCTTGACTAGAACTCCTCAGGTGCAGGCT
GCCTATCAGAAGGTGGTGGCTGGTGTGGCCAATGCCCTGGCTCACAAATACCACTGAGATCTT
TTTCCCTCTGCCAAAAATTATGGGGACATCATGAAGCCCCTTGAGCATCTGACTTCTGGCTAA
TAAAGGAAATTTATTTTCATTGCAATAGTGTGTTGGAATTTTTTGTGTCTCTCACTCGGAAGG
ACATATGGAGGGCAAATCATTTAAAACATCAGAATGAGTATTTGGTTTAGAGTTTGGCAACA
TATGCCCATATGCTGGCTGCCATGAACAAAGGTTGGCTATAAAGAGGTCATCAGTATATGAAA
CAGCCCCCTGCTGTCCATTCCTTATTCCATAGAAAGCCTTGACTTGAGGTTAGATTTTTTTT
ATATTTTGTTTTGTGTTATTTTTTTCTTTAACATCCCTAAAATTTTCCTTACATGTTTTACTA
GCCAGATTTTTCCTCCTCTCCTGACTACTCCAGTCATAGCTGTCCCTCTTCTCTTATGGAGA
TCCCTCGACG
```

Figure 4C

```
AGTGATGAGGCGCGCCGGGCGGCCGCTTCCCTTTAGTGAGGGTTAATGCTTCGAGGATGAGTC
GACCCGGGCGGCCGCTTCCCTTTAGTGAGGGTTAATGCTTCGAGACTCCTCAGGTGCAGGCTG
CCTATCAGAAGGTGGTGGCTGGTGTGGCCAATGCCCTGGCTCACAAATACCACTGAGATCTTT
TTCCCTCTGCCAAAAATTATGGGGACATCATGAAGCCCCTTGAGCATCTGACTTCTGGCTAAT
AAAGGAAATTTATTTTCATTGCAATAGTGTGTTGGAATTTTTTGTGTCTCTCACTCGGAAGGA
CATATGGGAGGGCAAATCATTTAAAACATCAGAATGAGTATTTGGTTTAGAGTTTGGCAACAT
ATGCCCATATGCTGGCTGCCATGAACAAAGGTTGGCTATAAAGAGGTCATCAGTATATGAAAC
AGCCCCCTGCTGTCCATTCCTTATTCCATAGAAAGCCTTGACTTGAGGTTAGATTTTTTTA
TATTTTGTTTTGTGTTATTTTTTTCTTTAACATCCCTAAAATTTTCCTTACATGTTTTACTAG
CCAGATTTTTCCTCCTCTCCTGACTACTCCCAGTCATAGCTGTCCCTCTTCTCTTATGGAGAT
CCCTCGACAAATCCGATAAGGATCGATCCGGGCTGGCGTAATAGCGAAGAGGCCCGCACCGAT
CGCCCTTCCCAACAGTTGCGCAGCCTGAATGGCGAATGGACGCGCCCTGTAGCGGCGCATTAA
GCGCGGCGGGTGTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCAAGCTCTAA
ATCGGGGGCTCCCTTTAGGGTTCCGATTTAGAGCTTTACGGCACCTCGACCGCAAAAAACTTG
ATTTGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCT
CGGTCTATTCTTTTGATTTATAAGGGATTTTGCCGATTTCGGCCTATTGGTTAAAAAATGAGC
TGATTTAACAAATATTTAACGCGAATTTTAACAAAATATTAACGTTTACAATTTCGCCTGATG
CGGTATTTTCTCCTTACGCATCTGTGCGGTATTTCACACCGCATACGCGGATCTGGTGTGGAA
AGTCCCCAGGCTCCCCAGCAGGCAGAAGTATGCAAAGCATGCATCTCAATTAGTCAGCAACCA
GGTGTGGAAAGTCCCCAGGCTCCCCAGCAGGCAGAAGTATGCAAAGCATGCATCTCAATTAGT
CAGCAACCATAGTCCCGCCCCTAACTCCGCCCATCCCGCCCCTAACTCCGCCCAGTTCCGCCC
ATTCTCCGCCCCATGGCTGACTAATTTTTTTATTTATGCAGAGGCCGAGGCCGCCTCGGCCT
CTGAGCTATTCCAGAAGTAGTGAGGAGGCTTTTTGGAGGCCTAGGCTTTTGCAAAGATCGAT
CAAGAGACAGGATGAGGATCGTTTCGCGCTAGCGCTACCGGTCGCCACCATGATTGAACAAGA
TGGATTGCACGCAGGTTCTCCGGCCGCTTGGGTGGAGAGGCTATTCGGCTATGACTGGGCACA
ACAGACAATCGGCTGCTCTGATGCCGCCGTGTTCCGGCTGTCAGCGCAGGGGCGCCCGGTTCT
TTTTGTCAAGACCGACCTGTCCGGTGCCCTGAATGAACTGCAGGACGAGGCAGCGCGGCTATC
GTGGCTGGCCACGACGGGCGTTCCTTGCGCAGCTGTGCTCGACGTTGTCACTGAAGCGGGAAG
GGACTGGCTGCTATTGGGCGAAGTGCCGGGGCAGGATCTCCTGTCATCTCACCTTGCTCCTGC
CGAGAAAGTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAAGCCGGTCT
TGTCGATCAGGATGATCTGGACGAAGAGCATCAGGGGCTCGCGCCAGCCGAACTGTTCGCCAG
GCTCAAGGCGCGCATGCCCGACGGCGAGGATCTCGTCGTGACCCATGGCGATGCCTGCTTGCC
GAATATCATGGTGGAAAATGGCCGCTTTTCTGGATTCATCGACTGTGGCCGGCTGGGTGTGGC
GGACCGCTATCAGGACATAGCGTTGGCTACCCGTGATATTGCTGAAGAGCTTGGCGGCGAATG
GGCTGACCGCTTCCTCGTGCTTTACGGTATCGCCGCTCCCGATTCGCAGCGCATCGCCTTCTA
TCGCCTTCTTGACGAGTTCTTCTGAAAGCGGGACTCTGGGGTTCGAAATGACCGACCAAGCGA
CGCCCAACCTGCCATCACGAGATTTCGATTCCACCGCCGCCTTCTATGAAAGGTTGGGCTTCG
GAATCGTTTTCCGGGACGCCGGCTGGATGATCCTCCAGCGCGGGGATCTCATGCTGGAGTTCT
TCGCCCACCCCAACTTGTTTATTGCAGCTTATAATGGTTACAAATAAAGCAATAGCATCACAA
ATTTCACAAATAAAGCATTTTTTTCACTGCATTCTAGTTGTGGTTTGTCCAAACTCATCAATG
TATCTTATCATGTCTGAATCGATAGCGATAAGGATCCGCGTATGGTGCACTCTCGGTTGCCGC
CGGGCGTTTTTTATTGGTGAGAATCCTCAGGTTACTCATATATACTTTAGATTGATTTAAAAC
TTCATTTTTAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCAGCGG
```

Figure 4C (continued)

```
TGGTTTGTTTGCCGGATCAAGAGCTACCAACTCTTTTTCCGAAGGTAACTGGCTTCAGCAGAG
CGCAGATACCAAATACTGTCCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCT
GAACGGGGGGTTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTATTACCG
CCATGCATTAGTTATTAAGACCAATAAAAAACGCCCGGCGGCAACCGAGCGTTCTGAACAAAT
CCAGATGGAGTTCTGAGGTCATTACTGGATCTATCAACAGGAGTCCAAGCGAGCTCGATATCA
AATTACGCCCCGCCCTGCCACTCATCGCAGTACTGTTGTAATTCATTAAGCATTCTGCCGACA
TGGAAGCCATCACAAACGGCATGATGAACCTGAATCGCCAGCGGCATCAGCACCTTGTCGCCT
TGCGTATAATATTTGCCCATGGTGAAAACGGGGGCGAAGAAGTTGTCCATATTGGCCACGTTT
AAATCAAAACTGGTGAAACTCACCCAGGGATTGGCTGAAACGAAAAACATATTCTCAATAAAC
CCTTTAGGGAAATAGGCCAGGTTTTCACCGTAACACGCCACATCTTGCGAATATATGTGTAGA
AACTGCCGGAAATCGTCGTGGTATTCACTCCAGAGCGATGAAAACGTTTCAGTTTGCTCATGG
AAAACGGTGTAACAAGGGTGAACACTATCCCATATCACCAGCTCACCGTCTTTCATTGCCATA
CGAAATTCCGGATGAGCATTCATCAGGCGGGCAAGAATGTGAATAAAGGCCGGATAAAACTTG
TGCTTATTTTTCTTTACGGTCTTTAAAAAGGCCGTAATATCCAGCTGAACGGTCTGGTTATAG
GTACATTGAGCAACTGACTGAAATGCCTCAAAATGTTCTTTACGATGCCATTGGGATATATCA
ACGGTGGTATATCCAGTGATTTTTTCTCCATTTTAGCTTCCTTAGCTCCTGAAAATCTCGAT
AACTCAAAAAATACGCCCGGTAGTGATCTTATTTCATTATGGTGAAAGTTGGAACCTCTTACG
TGCCGATCAACGTCTCATTTTCGCCAAAAGTTGGCCCAGGGCTTCCCGGTATCAACAGGGACA
CCAGGATTTATTTATTCTGCGAAGTGATCTTCCGTCACAGGTATTTATTCGGATTTAAATTTT
CACCGTCATCACCGAAACGCGCGAGGCAGCTGTGTAGTTATTAATAGTAATCAATTACGGGGT
CATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAG
TACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTAT
TAGTCATCGCTATTACCATGGTGATGCGGTTTTGGCAGTACATCAATGGGCGTGGATAGCGGT
TTGACTCACGGGGATTTCCAAGTCTCCACCCCATTGACGTCAATGGGAGTTTGTTTTGGCACC
AAAATCAACGGGACTTTCCAAAATGTCGTAACAACTCCGCCCCATTGACGCAAATGGGCGGTA
GGCGTGTACGGTGGGAGGTCTATATAAGCAGAGCTGGTTTAGTGAACCGTCAGATCAATTCGA
GCTCGGTACCCCAAACTTGACGGCAATCCTAGCGTGAAGGCTGGTAGGATTTTATCCCCGCT
GCCATCATGGTTCGACCATTGAACTGCATCGTCGCCGTGTCCCAAAATATGGGGATTGGCAAG
AACGGAGACCGACCCTGGCCTCCGCTCAGGAACGAGTTCAAGTACTTCCAAAGAATGACCACA
ACCTCTTCAGTGGAAGGTAAACAGAATCTGGTGATTATGGGTAGGAAAACCTGGTTCTCCATT
CCTGAGAAGAATCGACCTTTAAAGGACAGAATTAATATAGTTCTCAGTAGAGAACTCAAAGAA
CCACCACGAGGAGCTCATTTTCTTGCCAAAAGTTTGGATGATGCCTTAAGACTTATTGAACAA
CCGGAATTGGCAAGTAAAGTAGACATGGTTTGGATAGTCGGAGGCAGTTCTGTTTACCAGGAA
GCCATGAATCAACCAGGCCACCTCAGACTCTTTGTGACAAGGATCATGCAGGAATTTGAAAGT
GACACGTTTTCCCAGAAATTGATTTGGGGAAATATAAACTTCTCCCAGAATACCCAGGCGTC
CTCTCTGAGGTCCAGGAGGAAAAAGGCATCAAGTATAAGTTTGAAGTCTACGAGAAGAAAGAC
TAACAGGAAGATGCTTTCAAGTTCTCTGCTCCCTCCTAAAGCTATGCATTTTTATAAGACCA
TGGGGGATGCTCGATCCCCTCGCGAGTTGGTTCAGCTGCTGCCTGAGGCTGGACGACCTCGCG
```

Figure 4C (continued)

```
GAGTTCTACCGGCAGTGCAAATCCGTCGGCATCCAGGAAACCAGCAGCGGCTATCCGCGCATC
CATGCCCCCGAACTGCAGGAGTGGGGAGGCACGATGGCCGCTTTGGTCCGGATCTTTGTGAAG
GAACCTTACTTCTGTGGTGTGACATAATTGGACAAACTACCTACAGAGATTTAAAGCTCTAAG
GTAAATATAAAATTTTTAAGTGTATAATGTGTTAAACTACTGATTCTAATTGTTTGTGTATTT
TAGATTCCAACCTATGGAACTGATGAATGGGAGCAGTGGTGGAATGCCTTTAATGAGGAAAAC
CTGTTTTGCTCAGAAGAAATGCCATCTAGTGATGATGAGGCTACTGCTGACTCTCAACATTCT
ACTCCTCCAAAAAAGAAGAGAAAGGTAGAAGACCCCAAGGACTTTCCTTCAGAATTGCTAAGT
TTTTTGAGTCATGCTGTGTTTAGTAATAGAACTCTTGCTTGCTTTGCTATTTACACCACAAAG
GAAAAGCTGCACTGCTATACAAGAAAATTATGGAAAAATATTCTGTAACCTTTATAAGTAGG
CATAACAGTTATAATCATAACATACTGTTTTTCTTACTCCACACAGGCATAGAGTGTCTGCT
ATTAATAACTATGCTCAAAAATTGTGTACCTTTAGCTTTTTAATTTGTAAAGGGGTTAATAAG
GAATATTTGATGTATAGTGCCTTGACTAGCGACTGTGCCTTCTAGTTGCCAGCCATCTGTTGT
TTGCCCCTCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGTGGGGTGGG
GCAGGACAGCAAGGGGGAGGATTGGGAAGACAATAGCAGGCATGCTGGGGATGCGGTGGGCTC
TATGGAG
```

Figure 4D: pNT_MG004 (SEQ-ID NO. 8)

```
TCAATATTGGCCATTAGCCATATTATTCATTGGTTATATAGCATAAATCAATATTGGCTATTG
GCCATTGCATACGTTGTATCTATATCATAATATGTACATTTATATTGGCTCATGTCCAATATG
ACCGCCATGTTGGCATTGATTATTGACTAGTTATTAATAGTAATCAATTACGGGGTCATTAGT
TCATAGCCCATATATGGAGTTCCGCGTTACATAACTTACGGTAAATGGCCCGCCTGGCTGACC
GCCCAACGACCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCA
AGTGTATCATATGCCAAGTACGCCCCCTATTGACGTCAATGACGGTAAATGGCCCGCCTGGCA
TTATGCCCAGTACATGACCTTATGGGACTTTCCTACTTGGCAGTACATCTACGTATTAGTCAT
CGCTATTACCATGGTGATGCGGTTTTGGCAGTACATCAATGGGCGTGGATAGCGGTTTGACTC
ACGGGGATTTCCAAGTCTCCACCCCATTGACGTCAATGGGAGTTTGTTTTGGCACCAAAATCA
ACGGGACTTTCCAAAATGTCGTAACAACTCCGCCCCATTGACGCAAATGGGCGGTAGGCGTGT
ACGGTGGGAGGTCTATATAAGCAGAGCTCGTTTAGTGAACCGTCAGATCGCCTGGAGACGCCA
TCCACGCTGTTTTGACCTCCATAGAAGACACCGGGACCGATCCAGCCTCCGCGGCCGGGAACG
GTGCATTGGAACGCGGATTCCCCGTGCCAAGAGTGACGTAAGTACCGCCTATAGAGTCTATAG
GCCCACCCCCTTGGCTTCGTTAGAACGCGGCTACAATTAATACATAACCTTATGTATCATACA
CATACGATTTAGGTGACACTATAGAATAACATCCACTTTGCCTTTCTCTCCACAGGTGTCCAC
TCCCAGGTCCAACTGCACCTCGGTTCTATCGAAACGCGTCCACCATGGCCCCGTGGCCGTG
TGGGCTGCCCTGGCCGTGGGCCTGGAACTGTGGGCCGCTGCCCACGCCNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
```

Figure 4D (continued)

```
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNAGGCGCGCCGGGCGGCCGCTTCCCTTTAGTGAGGGTTAATGCTTCGAGCAGACATGAT
AAGATACATTGATGAGTTTGGACAAACCACAACTAGAATGCAGTGAAAAAAATGCTTTATTTG
TGAAATTTGTGATGCTATTGCTTTATTTGTAACCATTATAAGCTGCAATAAACAAGTTAACAA
CAACAATTGCATTCATTTTATGTTTCAGGTTCAGGGGGAGATGTGGGAGGTTTTTTAAAGCAA
GTAAAACCTCTACAAATGTGGTAAAATCCGATAAGGATCGATCCGGGCTGGCGTAATAGCGAA
GAGGCCCGCACCGATCGCCCTTCCCAACAGTTGCGCAGCCTGAATGGCGAATGGACGCGCCCT
GTAGCGGCGCATTAAGCGCGGCGGGTGTGGTGGTTACGCGCAGCGTGACCGCTACACTTGCCA
GCGCCCTAGCGCCCGCTCCTTTCGCTTTCTTCCCTTCCTTTCTCGCCACGTTCGCCGGCTTTC
CCCGTCAAGCTCTAAATCGGGGGCTCCCTTTAGGGTTCCGATTTAGAGCTTTACGGCACCTCG
ACCGCAAAAAACTTGATTTGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAA
CACTCAACCCTATCTCGGTCTATTCTTTTGATTTATAAGGGATTTTGCCGATTTCGGCCTATT
GGTTAAAAAATGAGCTGATTTAACAAATATTTAACGCGAATTTTAACAAAATATTAACGTTTA
CAATTTCGCCTGATGCGGTATTTTCTCCTTACGCATCTGTGCGGTATTTCACACCGCATACGC
GGATCTGCGCAGCACCATGGCCTGAAATAACCTCTGAAAGAGGAACTTGGTTAGGTACCTTCT
GAGGCGGAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGAAAGTCCC
CAGGCTCCCCAGCAGGCAGAAGTATGCAAAGCATGCATCTCAATTAGTCAGCAACCATAGTCC
CGCCCCTAACTCCGCCCATCCCGCCCCTAACTCCGCCCAGTTCCGCCCATTCTCCGCCCCATG
GCTGACTAATTTTTTTTATTTATGCAGAGGCCGAGGCCGCCTCGGCCTCTGAGCTATTCCAGA
AGTAGTGAGGAGGCTTTTTTGGAGGCCTAGGCTTTTGCAAAAAGCTTGATTCTTCTGACACAA
CAGTCTCGAACTTAAGGCTAGAGCCACCATGATTGAACAAGATGGATTGCACGCAGGTTCTCC
GGCCGCTTGGGTGGAGAGGCTATTCGGCTATGACTGGGCACAACAGACAATCGGCTGCTCTGA
TGCCGCCGTGTTCCGGCTGTCAGCGCAGGGGCGCCCGGTTCTTTTTGTCAAGACCGACCTGTC
CGGTGCCCTGAATGAACTGCAGGACGAGGCAGCGCGGCTATCGTGGCTGGCCACGACGGGCGT
TCCTTGCGCAGCTGTGCTCGACGTTGTCACTGAAGCGGGAAGGGACTGGCTGCTATTGGGCGA
AGTGCCGGGGCAGGATCTCCTGTCATCTCACCTTGCTCCTGCCGAGAAAGTATCCATCATGGC
TGATGCAATGCGGCGGCTGCATACGCTTGATCCGGCTACCTGCCCATTCGACCACCAAGCGAA
ACATCGCATCGAGCGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGGCGCGCATGCCCGA
CGGCGAGGATCTCGTCGTGACCCATGGCGATGCCTGCTTGCCGAATATCATGGTGGAAAATGG
CCGCTTTTCTGGATTCATCGACTGTGGCCGGCTGGGTGTGGCGGACCGCTATCAGGACATAGC
GTTGGCTACCCGTGATATTGCTGAAGAGCTTGGCGGCGAATGGGCTGACCGCTTCCTCGTGCT
TTACGGTATCGCCGCTCCCGATTCGCAGCGCATCGCCTTCTATCGCCTTCTTGACGAGTTCTT
CTGAGCGGGACTCTGGGGTTCGAAATGACCGACCAAGCGACGCCCAACCTGCCATCACGATGG
```

Figure 4D (continued)

```
CCGCAATAAAATATCTTTATTTTCATTACATCTGTGTGTTGGTTTTTTGTGTGAATCGATAGC
GATAAGGATCCGCGTATGGTGCACTCTCAGTACAATCTGCTCTGATGCCGCATAGTTAAGCCA
GCCCCGACACCCGCCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTTCACCGTCATCACC
GAAACGCGCGAGACGAAAGGGCCTCGTGATACGCCTATTTTTATAGGTTAATGTCATGATAAT
AATGGTTTCTTAGACGTCAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCA
ATAATATTGAAAAAGGAAGAGTATGAGTATTCAACATTTCCGTGTCGCCCTATTCCCTTTTT
TGCGGCATTTTGCCTTCCTGTTTTTGCTCACCCAGAAACGCTGGTGAAAGTAAAAGATGCTGA
AGATCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCTCAGAA
TGACTTGGTTGAGTACTCACCAGTCACAGAAAAGCATCTTACGGATGGCATGACAGTAAGAGA
ATTATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCTTGA
TCGTTGGGAACCGGAGCTGAATGAAGCCATACCAAACGACGAGCGTGACACCACGATGCCTGT
AGCAATGGCAACAACGTTGCGCAAACTATTAACTGGCGAACTACTTACTCTAGCTTCCCGGCA
ACAATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATTGC
AGCACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTTAATTTAA
AAGGATCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGCCTTTTGCTCACAT
GGCTCGACAGATCCATTTAAATTTTCACCGTCATCACCGAAACGCGCGAGGCAGCTGTGGAAT
GTGTGTCAGTTAGGGTGTGGAAAGTCCCCAGGCTCCCCAGCAGGCAGAAGTATGCAAAGCATG
CATCTCAATTAGTCAGCAACCAGGTGTGGAAAGTCCCCAGGCTCCCCAGCAGGCAGAAGTATG
CAAAGCATGCATCTCAATTAGTCAGCAACCATAGTCCCGCCCCTAACTCCGCCCATCCCGCCC
CTAACTCCGCCCAGTTCCGCCCATTCTCCGCCCCATGGCTGACTAATTTTTTTTATTTATGCA
GAGGCCGAGGCCGCCTCGGCCTCTGAGCTATTCCAGAAGTAGTGAGGAGGCTTTTTTGGAGGC
CTAGGCTTTTGCAAAAAGCTAATTCGAGCTCGGTACCCCCAAACTTGACGGCAATCCTAGCGT
GAAGGCTGGTAGGATTTTATCCCCGCTGCCATCATGGTTCGACCATTGAACTGCATCGTCGCC
GTGTCCCAAAATATGGGGATTGGCAAGAACGGAGACCGACCCTGGCCTCCGCTCAGGAACGAG
TTCAAGTACTTCCAAAGAATGACCACAACCTCTTCAGTGGAAGGTAAACAGAATCTGGTGATT
ATGGGTAGGAAAACCTGGTTCTCCATTCCTGAGAAGAATCGACCTTTAAAGGACAGAATTAAT
ATAGTTCTCAGTAGAGAACTCAAAGAACCACCACGAGGAGCTCATTTTCTTGCCAAAAGTTTG
GATGATGCCTTAAGACTTATTGAACAACCGGAATTGGCAAGTAAAGTAGACATGGTTTGGATA
GTCGGAGGCAGTTCTGTTTACCAGGAAGCCATGAATCAACCAGGCCACCTCAGACTCTTTGTG
```

Figure 4D (continued)

ACAAGGATCATGCAGGAATTTGAAAGTGACACGTTTTTCCCAGAAATTGATTTGGGGAAATAT
AAACTTCTCCCAGAATACCCAGGCGTCCTCTCTGAGGTCCAGGAGGAAAAAGGCATCAAGTAT
AAGTTTGAAGTCTACGAGAAGAAAGACTAACAGGAAGATGCTTTCAAGTTCTCTGCTCCCCTC
CTAAAGCTATGCATTTTTATAAGACCATGGGGATGCTCGATCCCCTCGCGAGTTGGTTCAGC
TGCTGCCTGAGGCTGGACGACCTCGCGGAGTTCTACCGGCAGTGCAAATCCGTCGGCATCCAG
GAAACCAGCAGCGGCTATCCGCGCATCCATGCCCCGAACTGCAGGAGTGGGGAGGCACGATG
GCCGCTTTGGTCCGAGATCTTTGTGAAGGAACCTTACTTCTGTGGTGTGACATAATTGGACAA
ACTACCTACAGAGATTTAAAGCTCTAAGGTAAATATAAAATTTTTAAGTGTATAATGTGTTAA
ACTACTGATTCTAATTGTTTGTGTATTTTAGATTCCAACCTATGGAACTGATGAATGGGAGCA
GTGGTGGAATGCCTTTAATGAGGAAAACCTGTTTTGCTCAGAAGAAATGCCATCTAGTGATGA
TGAGGCTACTGCTGACTCTCAACATTCTACTCCTCCAAAAAAGAAGAGAAAGGTAGAAGACCC
CAAGGACTTTCCTTCAGAATTGCTAAGTTTTTTGAGTCATGCTGTGTTAGTAATAGAACTCT
TGCTTGCTTTGCTATTTACACCACAAAGGAAAAAGCTGCACTGCTATACAAGAAAATTATGGA
AAAATATTCTGTAACCTTTATAAGTAGGCATAACAGTTATAATCATAACATACTGTTTTTTCT
TACTCCACACAGGCATAGAGTGTCTGCTATTAATAACTATGCTCAAAAATTGTGTACCTTTAG
CTTTTTAATTTGTAAAGGGGTTAATAAGGAATATTTGATGTATAGTGCCTTGACTAGAGATCA
TAATCAGCCATACCACATTTGTAGAGGTTTTACTTGCTTTAAAAAACCTCCCACACCTCCCCC
TGAACCTGAAACATAAAATGAATGCAATTGTTGTTGTTAACTTGTTTATTGCAGCTTATAATG
GTTACAAATAAAGCAATAGCATCACAAATTTCACAAATAAAGCATTTTTTCACTGCATTCTAG
TTGTGGTTTGAATTCGGATCT

MULTI-COPY GENE PROTEIN EXPRESSION SYSTEM

This application is a Section 371 national phase entry of PCT application PCT/EP2018/072687, filed Aug. 22, 2018. This application also claims the benefit of the earlier filing date of European patent application 17187552.9, filed Aug. 23, 2017.

This application contains a Sequence Listing which has been submitted electronically in ASCII format and is herein incorporated by reference. The ASCII file, created on Nov. 17, 2020, is named 75162us-topto-20201130-CorrectedSequenceListing.txt, and is 88,940 bytes in size.

The present invention belongs to the field of biotechnology, specifically to the field of recombinant protein expression. The present invention focuses on two problems commonly encountered during recombinant protein expression, low quantity of protein expression and genetic instability of cell lines used for recombinant protein expression. The basic principle of the present invention is to introduce several expression cassettes into a cell which expression cassettes all code for the same mature recombinant protein of interest, but which expression cassettes have different nucleotide sequences. Expression cassette means a polynucleotide sequence which comprises at least a promoter sequence, a start codon, a polynucleotide sequence coding for a protein which is intended to be recombinant expressed (POI), a stop codon and a terminator.

FIELD OF THE INVENTION

The present invention belongs to the field of biotechnology, specifically to the field of recombinant protein expression. Furthermore the invention relates to cells modified to express higher yields of recombinant protein (protein of interest, POI) and to modified cells which are less prone to genetic instability due to re-arrangement of the genetic material introduced into said modified cells. In another aspect the invention relates to vectors, expression cassettes used to generate said modified cells, as well as methods how to generate said modified cells and methods how to manufacture recombinant proteins using said modified cells, said vectors and said expression cassettes.

DESCRIPTION OF THE BACKGROUND ART

Recombinant protein expression in general has two main objectives: Firstly obtaining a recombinant protein of high quality, meaning e.g. pure, low content of degradation products, homogeneous regarding amino acid sequence and posttranslational modifications, soluble, correct three-dimensional folding and having the same biological activity as compared to the native, wild-type protein. Secondly the aim is to obtain a recombinant protein in high quantity in short time, e.g. in order to save costs, time and resources during the production process.

The present invention focuses on two problems commonly encountered during recombinant protein expression, low quantity of protein expression and genetic instability of cell lines used for recombinant protein expression.

In order to obtain high quantities of recombinant protein it is commonly tried to introduce not only one copy of a so called expression cassette into the cell chosen for recombinant protein production, but to try to introduce several copies of the expression cassette into a cell and subsequently select those modified host cells which have the optimal high number of expression cassettes in order to express the maximal amount of the protein of interest (POI). This strategy has at least two drawbacks:

First, the more copies of the expression cassette are introduced into the cell the more likely it is that over time the sequences of these expression cassettes recombine with each other due to the similarity of their sequences, which promotes recombination. As a consequence rearrangements of nucleotide sequences within the modified host cell result in an instable genome of the modified host cell used for protein expression. This results in a lower recombinant protein expression of the modified cell over time. In the worst case these unwanted recombination processes result in altered sequences of the POI, thereby not only decreasing the recombinant protein expression rate, but also decreasing the quality, because the recombinant protein gets a mixture of different variants of the POI, for example truncated or mutated versions of the POI, or POI with duplicated domains and region, etc.

Second, it is commonly recognized that a high copy number of an expression cassette is no guarantee for a high expression rate of the POI. Likely, a too high number of the expression cassette results in some kind of overburden or overstrain of the molecular machinery needed for protein expression of the modified host cell and thereby the expression rate of the POI goes down once the copy number of the expression cassette within the modified host cell exceeds a certain threshold.

SUMMARY OF THE INVENTION

The basic principle of the present invention is to introduce several expression cassettes into a cell which expression cassettes all code for the same mature recombinant protein of interest, but which expression cassettes have different nucleotide sequences. One of the main advantages of the present invention is its universal applicability, which is not limited to a certain type of cells, but can be used for prokaryotic as well as eukaryotic cells.

For example the expression cassettes may have different promoters, different terminators, different signal sequences, etc. and the coding sequence of the POI may be the same in the expression cassettes, or may be different in the different expression cassettes, however the amino acid sequence of the POI is always the same. The expression cassettes may have different nucleotide sequences coding for the same POI with the same amino acid sequence by utilizing the degenerated genetic code. The same amino acid may be coded for by up to 6 different codons, and thereby it is possible to have the same amino acid sequence coded by quite different nucleotide sequences. Furthermore, if the same vector element such as an expression cassette, a selection marker, an origin of replication, etc. is used twice within a vector or is used in more than one vector, said vector element might be used in different orientation within the vector sequences. This further increases the differences of the vector sequences and thereby lowers the likely hood of recombination of said vector elements within a transfected host cell comprising these two or more identical vector elements. This further increases genetic stability of said host cell.

This strategy has at least two main advantages. At the one side the expression cassettes now have quite different nucleotide sequences and therefore they are less likely to recombine with each other. This can result in a more stable genome of the modified cell which in turn allows to have higher copy numbers of the expression cassettes within the modified cell. On the other side the protein synthesis machinery of a modified cell is less likely to be overburden or overstrain due to high expression rates of the POI, because the modified cell in parallel uses:

Different promoters, which in turn use different sets of transcription factors, which can avoid potential bottlenecks due to the lack of sufficient amounts of certain transcription factors Different signal sequences, resulting in the in parallel use of different POI-secretion mechanisms, which can avoid potential bottlenecks in secretion pathways Different coding sequence of the POI, which in turn use different ratios of tRNAs for POI-synthesis, which can avoid potential bottlenecks in the supply of certain tRNAs Different terminator sequences, resulting in the in parallel use of different termination mechanisms/termination factors, which can avoiding potential bottlenecks in termination pathways Besides these two aspects the present invention furthermore has a third advantage. The skilled person is not required to find out in a series of experiments, which combination of promoter and POI works best in a certain host cell to be modified, because always a set of different types of promoters is used in parallel and even if an individual promoter in a certain POI/host cell combination does not perform well, this does not necessarily have a big effect on the overall expression rate of the POI, as other, different promoters are used at the same time that can compensate for the non-optimal promoter. This can result in e.g. faster development times for modified host cells suitable for cost-effective, efficient recombinant expression of a POI.

The concept of several in parallel used vectors, each vector comprising a single, different expression cassette for the same POI, has the additional advantage, that it is more flexible as compared to the also possible concept of using vectors comprising several different expression cassettes within the same vector. With a set of different single expression cassette vectors, the skilled person can easy and quickly test various combinations of different expression cassettes, and even can easily vary the relative abundance of the individual expression cassettes, simply be simultaneously transfecting the different vectors in different quantities (amount of transfected DNA of each single expression cassette vector) into one host cell. This allows to adjust the copy-number of the individual expression cassettes in order to get an optimal result regarding genetic stability of the host cell, and/or regarding POI expression rate.

Similar advantages can be obtained if the expression cassettes have the same promoter sequences. For instance, the expression cassettes have the same promoter sequences, different nucleotide sequences coding to the identical mature amino acid sequence of the POI, and optionally different terminator sequences and/or different signal sequences, if present.

Also the different mRNAs as a result of different coding sequences of the POI have different nucleotide sequences and therefore can have different stabilities, half-lives and different secondary structures which may or may not interfere with efficient translation of the mRNA into a POI. This mechanism avoids that the overall expression rate will be low just because by chance one certain version of mRNA is instable or has an unfavourable three-dimensional structure, because other, better suited versions of mRNAs are present at the same time and compensate for that.

In general, the more copies of a nucleic acid coding for a POI are transfected into a host cell, the higher is the expression rate. However, it is known to a skilled person in the field of recombinant protein expression that there is a certain threshold to that, meaning that a certain copy number the expression rate is no longer increasing, but instead may indeed decrease. The optimal copy number usually is determined empirically for each cell or POI. The same effect is also likely observed using the protein expression strategy of the invention disclosed herein. It is expected that increasing the copy number of individual expression cassettes of the invention at a certain threshold copy-number no longer increases the protein expression rate. It is furthermore expected that increasing the number of different expression cassettes coding for the same POI amino acid sequence also has a certain threshold-number, and furthermore increasing the number of said different expression cassettes does not further increase the quantity of expressed POI. The skilled person in the field of recombinant protein expression knows how to empirically determine the optimal number of an expression cassette for a certain POI in a certain type of host cell, for example simply by measuring the quantity of expressed POI and comparing it with the copy number of expression cassettes detected in the same host cell.

One of the main advantages of the present invention is its universal applicability, independent of the type of cells used. The invention is useable for all types of cells, eukaryotic as well as prokaryotic cells. It can be used for example with mammalian cells, yeast cells, fungal cells, bacteria, etc.

In the prior art this concept is unknown. The only protein expression strategy which remotely goes into the direction of the invention described herein is the concept to express several different POI at the same time in the same host cell, for example the alpha- and the beta-chain of a T-cell receptor (WO 2016/073794), the light and the heavy chain of an antibody (WO 03/018771), L- and H-ferritin (J. Microbiol. Biotechnol, 2008, 18: 926-932), etc. However these concepts in the prior art are clearly different to the present invention in several aspects:

The main intension is not to obtain host cells which are genetically more stable with less unwanted recombination and the concept is also not to get higher expression rates by introducing more copies of nucleic acids into the host cells, coding for the same POI The only reason for expression of two or more different POI simultaneously in one host cell, as described in the prior art, is to get protein complexes built from different POI, which in an ideal case are even assembled by the host cell to the final protein complex, such as a T-cell receptor or an antibody.

The main intention in the prior art is not to get maximal POI expression, but to express the different POI in correct stoichiometric quantitative proportion in order to promote the correct assembly of the protein complex. For this reason, in the prior art a vector is used, which contains two expression cassettes within the same vector, wherein each expression cassette results in expression of one of the two polypeptide chains of the multimeric protein complex, very often an antibody-fragment composed of two polypeptide chains. By combining both expression cassettes into the same vector the problem to express both polypeptide chains in equimolar quantity is much easier to accomplish.

WO 2016/005931 describes a method to increase the protein expression in *E. coli* using a dual, independent cistron expression system wherein both cistrons are located within one vector. The main object of this application is to increase the expression of proteins, especially antibody fragments such as Fab fragments consisting of two polypeptide sequences. The use of the dual cistron expression system for expression of only one protein of interest is also disclosed. However also this concept is different from the present invention in several aspects:

- The use of more than two cistrons is not disclosed and only the use of one vector containing these two cistrons is disclosed. Neither the use of more than two cistrons nor the alternative use of several vectors in parallel, each vector containing one cistron, is disclosed.
- The reason for using two cistrons is to simultaneously express two separate polypeptide chains needed for one protein complex such as an antibody and to increase the quantity of recombinant protein.
- Only protein expression as inclusion bodies in bacterial cells is disclosed.

Items of the Invention

The present invention provides the following aspects, subject-matters and preferred embodiments, which respectively taken alone or in combination, contribute to solving the object of the present invention:

Item (1): Host cell comprising three or more different types of expression cassettes, each expression cassette coding for the same Protein Of Interest (POI) with identical mature amino acid sequence, and each type of expression cassette at least is comprising a promoter sequence, a polynucleotide sequence of the coding sequence of the POI, and a terminator sequence, wherein said expression cassettes differ in, that they comprise (a) different promoter sequences,
and optionally
(b) different nucleotide sequences coding for the identical mature amino acid sequence of the POI due to the use of degenerated genetic code, and/or
(c) different terminator sequences, and/or
(d) different signal sequences, if present,
preferably
a host cell comprising three or more different types of expression cassettes, each expression cassette coding for the same Protein Of Interest (POI) with identical mature amino acid sequence, and each type of expression cassette at least is comprising a promoter sequence, a polynucleotide sequence of the coding sequence of the POI, and a terminator sequence, wherein said expression cassettes differ in that they comprise
(A)
(Aa) different promoter sequences,
(Ab) different nucleotide sequences coding for the identical mature amino acid sequence of the POI due to the use of degenerated genetic code,
and optionally
(Ac) different terminator sequences, and/or
(Ad) different signal sequences, if present,
or wherein said expression cassettes differ in that they comprise
(B)
(Ba) the same promoter sequences,
(Bb) different nucleotide sequences coding for the identical mature amino acid sequence of the POI due to the use of degenerated genetic code,
and optionally
(Bc) different terminator sequences, and/or
(Bd) different signal sequences, if present.

Item (2): Host cell according to item (1), wherein said host cell expresses higher quantities of said POI as compared to a host cell comprising the same number of expression cassettes with identical promoter sequences, wherein said higher quantities of said POI are determined for example by measurement of said POI using ELISA measurements, densitometrically measured western blots, densitometrically measured coomassie blue or silver stained SDS-PAGE gels, quantitative mass spectrometry, or quantification of the area below the peak of said POI after chromatographic separation of said POI from a sample. The quantity of said POI is at least 5%, 10%, 20%, 30%, 40%, 50%, 60%, 70%, 80%, 90%, 100%, 150%, 200%, 300%, 400% or at least 500% increased as compared to a host cell comprising the same number of expression cassettes but with identical promoter sequences. The quantity of said POI is increased by at least 50%, preferably by at least 30%, more preferably by at least 20%, most preferably by at least 10%. Methods suitable to determine the quantity of POI expression are described elsewhere herein.

Item (3): Host cell according to item (1) or (2), wherein the genome of said host cell is more stable as compared to a host cell comprising the same number of expression cassettes but with identical promoter sequences wherein the genetic stability is determined for example by determining the copy number of the GOP within the host cells after at least 100 host cell generations, for example by quantitative PCR, or by determining the correct length of PCR-products obtained by use of GOP-specific PCR-primers, or by sequencing of the genome of the host cell. Methods suitable for determining the stability of the genome of the host cells are described elsewhere herein.

Item (4): Host cell according to any of items (1) to (3), wherein genetic stability is measured by determining how much genetic variation regarding said expression cassettes is present in said host cells after at least 20, 30, 40, 50, 60, 70, 80, 90, 100, 150, 200, 300, 400, or at least 500 cell generations of prokaryotic cells or after at least 20, 30, 40, 50, 60, 70, 80, 90, 100, 150, 200, 300, 400, or at least 500 cell generations of eukaryotic cells. Genetic variation of prokaryotic cells, especially of *Escherichia coli* cells, is measured after at least 200 cell generations, preferably after at least 150 cell generations, more preferably after at least 100 cell generations, most preferably after at least 50 cell generations. Genetic variation of yeast cells, preferably of *Saccharomyces cerevisiae* or *Pichia pastoris* cells, more preferably of *Pichia pastoris* cells, is measured after at least 160 cell generations, preferably after at least 120 cell generations, more preferably after at least 80 cell generations, most preferably after at least 40 cell generations. Genetic variation of mammalian cells such as CHO cells is measured after at least 150 cell generations, preferably after at least 120 cell generations, more preferably after at least 90 cell generations, most preferably after at least 60 cell generations.

Item (5): Host cell according to any of items (1) to (4), wherein said genetic stability is indicated by a change of the host cell genome which effects a nucleotide sequence of at least 5 to 20, preferably at least 5 to 100, more preferably at least 5 to 500, most preferably at least 5 to 1500 nucleotide length.

Item (6): Host cell according to any of items (1) to (5), wherein said promoter is selected from the list comprising unidirectional promoter, bidirectional promoter, and/or a promoter which controls the expression of two or more POI, for example by use of IRES sequences.

Item (7): Host cell according to any of items (1) to (6), wherein said promoter sequence has a length of at least 10, 15, 20, 30, 40, 50, 100, 150, 200, 250, 300, 400, 500, 600, 700, 800, 900, 1000, 1200, 1400, 1600, 1800, 2000, 2500 or at least 3000 nucleotides. Said promoter sequence has a length of at least 50, preferably at least 20, more preferably at least 15, most preferably at least 10 nucleotides for prokaryotic cells. Said promoter sequence in the case of yeast cells, preferably in the case of *Pichia pastoris* or *Saccharomyces cerevisiae*, more preferably in the case of *Pichia pastoris*, has a length of at least 500, preferably at least 300, more preferably at least 200, most preferably at least 100 nucleotides. Said promoter sequence for mammalian cells such as CHO has a length of at least 500, preferably at least 300, more preferably at least 200, most preferably at least 100 nucleotides for mammalian cells such as CHO cells.

Item (8): Host cell according to any of items (1) to (7), wherein said promoter is a constitutive active promoter, or wherein said promoter is an inducible promoter.

Item (9): Host cell according to any of items (1) to (7), wherein at least one expression cassettes comprises an inducible promoter and at least one expression cassette comprises a constitutively active promoter.

Item (10): Host cell according to any of items (1) to (9), wherein said terminator sequence is present in at least three, preferably at least two, more preferably at least one copy, and wherein said terminator sequences are the same or different terminator sequences, if more than one terminator sequence is present.

Item (11): Host cell according to any of items (1) to (10), wherein said signal sequence comprises a secretion signal sequence and/or intracellular targeting sequence, targeting the POI to a certain desired compartment, organelle or location of the cell, for example in the case of bacterial cells into the periplasm.

Item (12): Host cell according to any of items (1) to (11), wherein said signal sequence is either is a different signal sequence with regard to its amino acid sequence, and/or wherein said signal sequence has the same amino acid sequence but is coded by a different nucleotide sequence.

Item (13): Host cell according to any of items (1) to (12), comprising at least 3, 4, 5, 6, 7, 8, 9, 10, 11, 12, 13, 14, or 15 expression cassettes.

Item (14): Host cell according to any of items (1) to (13), wherein at least one expression cassette codes for two or more POI with identical mature amino acid sequence, wherein between the coding sequences of said two or more POI an IRES sequence is located, or a sequence functioning like an IRES sequence. Alternatives for IRES sequences functioning like an IRES sequences are for example the 2A, P2A, T2A and the F2A sequences (S. C. L. Ho et al, PLOS, 2013, Vol. 8, Issue 5, e63247).

Item (15): Host cell according to any of items (1) to (14), wherein point (b) of item (1) applies and said different nucleotide sequences of the coding sequence of the POI are coded by a degenerated genetic code, which degenerated genetic code results in at least 50% of the maximum theoretical nucleotide sequence difference possible for that particular POI coding nucleotide sequence in order to get an identical mature amino acid sequence of said particular POI.

Item (16): Host cell according to any of items (1) to (14), wherein point (b) of Item (1) applies and said different nucleotide sequences of the coding sequence of the POI are coded by a degenerated genetic code, which degenerated genetic code results in at least 5%, 10%, 20%, 30%, 40%, 50%, 60%, 70%, 80%, at least 90% or in 100% of the maximum theoretical nucleotide sequence difference possible for that particular POI coding nucleotide sequence in order to get an identical mature amino acid sequence of said particular POI.

Item (17): Host cell according to any of items (1) to (16), wherein said promoter, said terminator, and/or said signal sequences, if present, differ by at least 20%, preferably at least 30%, more preferably at least 40%, most preferably at least 50% regarding their nucleotide sequence.

Item (18): Host cell according to any one of Items (1) to (17), wherein said promoter sequences differ by at least 5, 10, 15, 20, 25, 30, 35, 40, 45, 50, 55, 60, 65, 70, 75, at least 80% regarding their nucleotide sequence, and/or wherein said terminator sequences differ by at least 5, 10, 15, 20, 25, 30, 35, 40, 45, 50, 55, 60, 65, 70, 75, at least 80% regarding their nucleotide sequence, and/or wherein said signal sequence, if present, differ by at least at least 5, 10, 15, 20, 25, 30, 35, 40, 45, 50, 55, 60, 65, 70, 75, at least 80% regarding their nucleotide sequence.

Item (19): Host cell according to any of items (1) to (18), wherein said POI is heterologous to said host cell.

Item (20): Host cell according to any of item (1) to (19), wherein point (b) of item (1) applies and said different nucleotide sequences of the coding sequences of the POI at least have a length of 30, preferably at least 60, more preferably at least 90 nucleotides.

Item (21): Host cell according to any of item (1) to (19), wherein point (b) of item (1) applies and said different nucleotide sequences of the coding sequence of the POI at least have a length of 30, 40, 50, 60, 70, 80, 90, 100, 110, 120, 130, 140, 150, 160, 170, 180, 190, 200, 250, 300, 350, 400, 450, 500, 750, 1000, 1500, at least of 2000 nucleotides. The nucleotide sequences preferably have a sequence length of at least 180, preferably of at least 120, more preferably of at least 60, most preferably of at least 30 nucleotides.

Item (22): Host cell according to any of items (1) to (21), wherein said host cell is
  (i) an eukaryotic cell, preferably selected from
    (a) filamentous fungal cells, preferably *Aspergillus, Trichoderma* or *Penicillium,*
    (b) yeast cells, preferably *Pichia pastoris, Saccharomyces cerevisiae,* or *Y. lipolytica*, more preferably *Pichia pastoris,*
    (c) mammalian cells, preferably CHO (Chinese Hamster Ovary) cells;
    (d) human cells, preferably HEK293 cells (HEK=Human Embryonic Kidney),
    (e) insect cells, preferably sf5, sf21 or high five cells (sf=spondoptera *frugiperda*), or
  (ii) a prokaryotic cell, preferably a bacterial cell, more preferably *Escherichia coli.*

Item (23): Host cell according to item (22), wherein said host cell is a CHO cell, *Pichia pastoris* or *Escherichia coli*, preferably said host cell is a CHO cell or *Pichia pastoris*.

Item (24): Host cell according to item (22) or (23), wherein said host cell is a CHO cell.

Item (25): Host cell according to item (22) or (23), wherein said host cell is a *Pichia pastoris* cell.

Item (26): Host cell according to item (22) to (23), wherein said host cell is an *Escherichia coli* cell.

Item (27): Method of generating a host cell as defined in any one of items (1) to (26), comprising the step of transfecting said host cell with at least three different nucleic acid sequences, wherein each nucleic acid sequence comprises at least one different expression cassette coding for the same mature amino acid sequence of said POI.

Item (28): Method according to item (27), wherein transfection of said host cell is done with at least 2, 3, 4, 5, 6, 7, 8, 9, or at least 10 different nucleic acid sequences, for example different vectors. Said transfection is done with at least 6, preferably with at least 4, more preferably with at least 3, most preferably with at least 2 different nucleic acids.

Item (29): Method of generating a host cell as defined in any of items (1) to (26), comprising a step of transfecting said host cell with at least one nucleic acid sequence, wherein said nucleic acid sequence comprises at least three different expression cassettes, and each of said expression cassettes is coding for the same mature amino acid sequence of said POI.

Item (30): Method according to item (29), wherein transfecting said host cell is done with a nucleic acid sequence which nucleic acid sequence comprises at least 2, 3, 4, 5, 6, 7, 8, 9, or at least 10 different expression cassettes. Said nucleic acids comprise at least 6, preferably at least 5, more preferably at least 4, most preferably at least 3 expression cassettes.

Item (31): Nucleic acid comprising at least three expression cassettes as defined in any of items (1) to (21).

Item (32): Nucleic acid comprising at least 2, 3, 4, 5, 6, 7, 8, 9, or at least 10 expression cassettes as defined in any of items (1) to (21). Said nucleic acids comprise at least 6, preferably at least 5, more preferably at least 4, most preferably at least 3 expression cassettes.

Item (33): Vector comprising at least three expression cassettes as defined in any of items (1) to (21).

Item (34): Vector according to item (33), further comprising an antibiotic selection marker or a metabolic or an auxotrophic selection marker.

Item (35): Vector according to item (34), wherein said antibiotic selection marker in the case of bacterial cells preferably is a resistance to Ampicillin, Kanamycin, Zeocin, Geneticin (G418), Neomycin, Glyphosate, Puromycin, Hygromycin B, Phleomycin, Blasticidin, Mycophenolic Acid, etc.

Item (36): Vector according to item (34), wherein said metabolic selection marker in the case of CHO cells preferably is dihydrofolate reductase (DHFR), glutamine synthetase (GS), folic acid receptor (folR), etc.

Item (37): Vector according to item (34), wherein said metabolic selection marker in the case of yeast cells preferably is LEU2, HIS3, URA3, ADE, 5-FOA (5-Fluoroorotic Acid), etc. (Brachmann et. al., 1998, Yeast, 14:115-132), and/or preferably said antibiotic selection marker is Zeocin, G418 (Geneticin), Phleomycin, Hygromycin B, Puromycin, Blasticidin, Mycophenolic Acid, etc.

Item (38): Vector comprising at least 3, 4, 5, 6, 7, 8, 9, or at least 10 expression cassettes with different promoters, wherein said expression cassettes lack a gene of interest and optionally at the position of the lacking gene of interest there is inserted a cloning site or a multiple cloning site. Said vector comprises at least 6, preferably at least 5, more preferably at least 4, most preferably at least 3 expression cassettes.

Item (39): Kit comprising at least three nucleic acids, wherein said nucleic acids preferably are vectors, and wherein each nucleic acid comprises at least one expression cassette as defined in any of items (27) to (32).

Item (40): Kit according to item (39), wherein said kit comprises at least 3, 4, 5, 6, 7, 8, 9, or at least 10 nucleic acids.

Item (41): Kit according to item (39) or (40), wherein said nucleic acids are vectors.

Item (42): Kit comprising a nucleic acid as defined in item (31) or (32), or a vector as defined in any of items (33) to (38).

Item (43): Kit according to item (42), wherein said nucleic acid comprises at least 3, 4, 5, 6, 7, 8, 9, or at least 10 expression cassettes.

Item (44): Kit according to item (41) or (42), wherein said nucleic acid is a vector.

Item (45): Kit according to any of items (39) to (44), wherein said vector or said vectors are vectors according to any of items (33) to (38).

Item (46): Kit according to any of items (39) to (45), further comprising instructions in the form of a paper leaflet, an electronic manual or in other form, which instructions explain how to use said kit.

Item (47): Process for the manufacture of a POI by use of a host cell as defined in any of items (1) to (26), a nucleic acid as defined in item (31) or (32), a vector as defined in any of items (33) to (38), or a kit as defined in any of items (39) to (46).

Item (48): Process according to item (47), wherein said POI is a single chain protein, or originates from a precursor of a single chain polypeptide, such as for example insulin.

Item (49): Process according to item (48), wherein said single chain protein is a protein which is
  a) present in nature as a single chain protein;
  b) present in nature as a protein comprising at least two polypeptide chains, but which protein in nature originates from a single chain precursor protein, e.g. insulin (precursor of insulin is a single chain, finally processed insulin comprises two chains connected by disulphide bridges);
  c) a fusion protein which is made of different proteins;
  d) a fusion protein which is made of parts of the same protein;
  e) a fusion protein which is made of parts of different proteins; or
  f) present in nature as a protein comprising at least two polypeptide chains but was manufactured by use of molecular biologic techniques in a way resulting in a single chain protein, such as for example a single chain antibody.

Definitions and Terms within the Meaning of the Present Invention

The titles given in front of paragraphs of this application are meant to guide through the text of the application, but are not meant and should not be understood to limit the scope of the invention in any way.

The term "and/or" wherever used herein includes the meaning of "and", "or" and "all or any other combination of the elements connected by said term". For example, A, B and/or C means A, B, C, A+B, A+C, B+C and A+B+C.

"Host cell" means the cell, which is used for expression of a recombinant protein. The host cell can be any type of cells such as bacterial cells, yeast cells, fungal cells, mammalian cells, human cells, cell lines such as cancer cells or cells which have been experimentally modified resulting in immortalized cells (=cells which divide an unlimited number of times, the same as cancer cells), etc.

"Expression cassette" means a polynucleotide sequence which comprises at least a promoter sequence, a start codon, a polynucleotide sequence coding for a protein which is intended to be recombinant expressed (POI), a stop codon and a terminator. An expression cassette may comprise additional regulatory and other sequences such as enhancers, signal sequences, enhancers, introns, IRES-sequences, etc. A host cell comprising three or more different expression cassettes may be a host cell which was transfected with three or more vectors, each vector comprising a different expression cassette. The resulting host cell might comprise said vectors present as plasmids within its cytosol, or might have integrated said expression cassettes and optionally further parts of said vectors into its genome. It might also be that some of the transfected vectors are integrated (partially or complete) into the genome of said host cells, whereas other of said transfected vectors are present as plasmids within the cytosol of said host cell. Said host alternatively also might have been transfected with at least one vector comprising at least three different expression cassettes within said one vector, or with mixtures of vectors comprising individual expression cassettes and at the same time transfected with vectors comprising two or more different expression cassettes.

"Transfection" of a GOI (meaning an expression cassette of a GOI) or of a vector (meaning a vector comprising at least one expression cassette of a GOI) might result in transfected host cells (or transformed host cells, which is the same), wherein said host cells have integrated said GOI or said vector into their chromosome (if said cell has only one chromosome), or said host cells have integrated said GOI or said vector into several or all of their chromosomes (if said host cell has more than one chromosome). Said GOI or vector might be integrated once or several times into said chromosome, preferably it is integrated several times into a chromosome. Preferably it is integrated in more than one chromosome of the same host cell. If a vector is integrated into a chromosome the complete sequence or only part of the sequence of said vector might get integrated into said chromosome, but at least the expression cassette of said GOI present in said vector is integrated into said chromosome. Alternatively said vector might not get integrated into a chromosome of said host cell, but might exist outside of a chromosome within the cytosol of said host cell, for example in the form of a circular, double-stranded desoxy-polynucleic acid. If said host cell is a eukaryote, more preferably if said host cell is a mammalian or a yeast or a fungal cell, most preferably is said host cell is a CHO cell or a *Pichia pastoris* cell, preferably said GOI or said vector is integrated into a chromosome of said host cell. If said host cell is a prokaryote, preferably a bacterial cell, more preferably an *E. coli* cell, said vector preferably is not integrated into the chromosome of said host cell but is located in the cytosol of said host cell.

If an expression cassette comprises two or more polynucleotide sequences coding for the protein which is intended to be recombinant expressed (POI) and said two or more polynucleotide sequences are expressed due to the function of a single promoter polynucleotide within said expression cassette, said expression cassette is still regarded as one expression cassette. Such an expression cassette for example could for example arise from the use of IRES sequences, or from the use of a bi-directional promoter. A bi-directional promoter is a promoter which results in expression of two coding sequences, one of which is located 5' to the promoter and one is located 3' to the promoter.

Further parts of a vector used according to the invention, which parts are not directly needed for the expression of the POI, such as for example the origin of replication (ori), antibiotic resistance gene, or metabolic selection marker, etc. are not regarded as part of the expression cassette. However also some or all of these parts of the vector might be different in different vectors. For example if several individual vectors are used according to the invention, each of these vectors might contain a different antibiotic resistance gene or a different metabolic selection marker or a different origin of replication (ori), etc. Alternatively the antibiotic resistance gene and/or the metabolic selection marker, etc. might be the same protein, but the nucleic acid sequence within the vector coding for said protein might be different due to the degenerated genetic code, but still code for the identical antibiotic resistance protein or metabolic selection marker protein.

"Coding": A polynucleotide or sequence "codes" if it results in, if combined with appropriate regulatory sequences such as a promoter, a start codon, a stop codon and a terminator, etc., in the expression of a protein or polypeptide or peptide comprising at least 10, at least 20, at least 30, at least 50 or at least 100 amino acids connected via peptide bonds.

"Coding sequence" or "coding region" means those parts of a polynucleotide, which code for the amino acid sequence of the mature amino acid sequence. "Mature amino acid sequence" is explained a few paragraphs below.

"Open reading frame" means those parts of a polynucleotide, which code for amino acid sequences, regardless if these amino acid sequences are present in the final mature amino acid sequence or if these amino acid sequences are removed during the processing of the POI, for example amino acid sequences of a signal peptide, which are removed from the POI in order to obtain the "mature amino acid sequence".

"Protein Of Interest", also abbreviated POI, is a protein, polypeptide, or peptide comprising at least 10, at least 20, at least 30, at least 50, at least 100, at least 150, at least 200, at least 250 amino acids connected via peptide bonds, which POI is intended to be recombinantly expressed by use of a host cell. The POI is coded by a "Gene Of Interest" (GOI). The amino acid sequence of the POI is regarded as the "mature amino acid sequence".

The POI can be a protein, polypeptide or peptide, which is present in nature, or a protein, polypeptide, or peptide, which is not present in nature, for example a fusion protein of two peptides, polypeptides, proteins, protein-domains, etc. present in nature, which fusion protein is not present in nature. For example the POI might be a protein present in nature fused to a His-tag, or fused to other peptides which are intended to label, or to purify the fusion protein, or fusion proteins comprising domains of two or more proteins present in nature, which domains normally are not present in nature within one protein, polypeptide or peptide, or a non-human sequence which has been "humanized" like for example humanized antibodies, etc. Humanized antibodies are for example murine antibodies, whose constant amino acid sequence part has been replaced by the corresponding amino acid sequence part of a human antibody. Therefore mature amino acid sequence in general means the final amino acid sequence intended to be manufactured by the person, who designed or performed the experiment to obtain the POI.

Consequently the mature amino acid sequence of a POI can be:
  The sequence of a protein, as it is present in nature;
  A fragment or a domain of the sequence of a protein, which fragment or domain is not found in nature;
  A mutant of a sequence of a protein, which mutant is not found in nature;
  A fusion protein, for example obtained by addition of peptides used for detection or purification of the fusion protein;
  A fusion protein, for example build from protein domains of two or more different protein;
  A fusion protein, for example build by protein domains, which have been rearranged, as compared to their natural arrangement;

A protein which was designed completely from scratch by man;

etc.

"Mature amino acid sequence" means for example the amino acid sequence of a protein after it has undergone the complete processing steps of the corresponding non-recombinant protein, polypeptide or peptide regarding its amino acid sequence. For example secretion signal sequences have been removed, the pre- or the pre-pro-form of for example a protein have been converted to the final protein, polypeptide or peptide sequence, or internal sequences within the amino acid sequence have been removed during processing. For example in the case of insulin this means: pre-pro-insulin: removal of signal sequence=pro-insulin; pro-insulin: removal of the internal C-peptide=insulin=the mature amino acid sequence in this case.

"Mature recombinant protein" means a recombinant protein comprising a mature amino acid sequence, as defined above. Introns in general do not code for a part of the mature protein, polypeptide, or peptide.

"Processing sequences" means amino acid sequences, which are removed from the protein, polypeptide or peptide in order to obtain a mature amino acid sequence, such as secretion signal sequences, signal sequences for intracellular protein targeting, pre-pro-sequences, pro-sequences, etc.

The sequence of the POI might comprise or might partially or completely lacking processing sequences. Said processing sequences are often present in proteins present in nature (native proteins, natural proteins) and are often needed for correct processing of the native protein, or for the correct physically location of the native protein in the correct location inside or outside the cell, or for the transport of the native protein, etc. A transmembrane sequence usually is not removed during processing of a protein, polypeptide or peptide and therefore is normally not regarded as processing sequence. A transmembrane sequence is only then regarded as processing sequence, if the POI is only transiently localized to the cell membrane by use of said transmembrane sequence and said transmembrane sequence is removed from the rest of the POI during the processing of the POI in order to obtain the POI.

Promoter or promoter sequences means a region of a polynucleotide, which initiates transcription of a gene or in the case of the current invention initiates the transcription of a nucleotide sequence coding for a POI. The promoter can be an "inducible promoter" or "constitutive promoter." IRES sequences and sequences function like IRES sequences are not regarded as a promoter or a promoter sequence. "inducible promoter" refers to a promoter which can be induced by the presence or absence of certain induction factors, and "constitutive promoter" refers to an unregulated promoter which is active at all times, independent of the presence of certain induction factors, that allow for continuous transcription of its associated gene or genes. Optionally, a promoter my initiate the transcription of two or more genes if for example these two or more genes are separated by an IRES sequence. Optionally, a promoter my initiate the transcription of two genes, if said promoter for example is a bi-directional promoter.

"Degenerated genetic code" means that for a certain amino acid there are more than one nucleotide codons. For example the amino acid Cysteine can be coded for by the following two different codons: TGC or TGT, the amino acid Arginine can be coded for by the following 6 codons: CGG, CGA, CGC, CGT, AGG, AGA, etc. As a consequence the same amino acid sequence can be coded for by different nucleotide sequences. If only the individual codons are exchanged but not the amino acid for which these codons code. The degenerated genetic code is the same for almost all organisms with a few exceptions. For example human mitochondria have a different genetic code. Within this patent application "degenerated genetic code" is always meant regarding the genetic code of the specific cell or the specific organelle (such as a mitochondrion), which is intended to be use to express the POI.

"Terminator" means the same as "transcription terminator". According to the invention a terminator is a section of nucleic acid sequence that marks the end of the nucleic acid sequence needed to code for a POI. Usually said terminator is localized shortly downstream of the stop-codon of the GOI. In prokaryotes termination includes Rho-independent as well as Rho-dependant transcription termination. Prokaryotic termination sequences used according to the invention preferably are Rho-independent termination sequences such as the T7 and the rrnB termination sequences. Rho-independent termination is also known as intrinsic terminations. Preferably in one expression cassette one or two termination sequences are used. Two combined termination sequences increase the termination efficiency. If IRES sequences are used preferably more than one termination sequence are placed between two coding sequences of the POI. Mammalian termination sequences are for example SB40-, hGH-, BGH- or rbGlob-termination sequences.

"signal sequence" means an amino acid sequence which usually is needed to direct a protein, polypeptide or peptide to be secreted into the extracellular region and which signal sequence usually is removed from the mature amino acid sequence by proteolysis. There are also signal sequences, which direct the protein, polypeptide or peptide to certain organelles of the cell. Bacterial cells also use signal sequences, for example signal sequences, which direct a POI into the periplasm. Signal sequences usually are located at the N-terminal end of an amino acid sequence, but can also be present at the C-terminal end or can be present internally, within the polypeptide sequence.

"IRES" sequences, also named "internal ribosome entry site" sequences are nucleotide sequences within the mRNA, which allow for the translation initiation within the mRNA sequence and do not depend on the 5'-end of the mRNA for initiation of the translation. So IRES sequences allow to express two or more POI from one mRNA. Alternatives for IRES sequences with the same principal function as IRES sequences are for example the 2A, P2A, T2A and the F2A sequences.

"Heterologous" protein, polypeptide, peptide sequence means that the amino acid sequence coded by a nucleotide sequence is not naturally present in the host cell. If an amino acid sequence, which is naturally present in the host cell is mutated (e.g. point mutations, insertions, deletions, fusions, etc.) the resulting mutated sequence is also regarded as heterologous sequence.

"Heterologous" polynucleotide or nucleotide sequence means that the polynucleotide or nucleotide sequence is not naturally present in the host cell. If a naturally in the host cell present polynucleotide or nucleotide sequence is modified by exchanging individual nucleotides in a way that said polynucleotide or nucleotide sequence still codes for the same amino acid sequence, such a modified polynucleotide or nucleotide sequence is regarded as heterologous.

The terms "sequence difference", and terms like "differ", "different", "differing", etc. if mentioned in connection with amino acid sequences or nucleic acid sequences are meant to be determined for example as follows:

In the present invention, reference is made e.g. to "different promoter sequences" or different nucleotide sequences coding for the (identical) mature amino acid sequence of the POI. Thus, in order to determine whether said sequences are "different", the respective corresponding sequences (amino acid sequences or nucleotide sequences) are compared regarding their sequence identity. For instance, the promoter sequences are compared or the nucleotide sequences coding for the mature amino acid sequence of the POI.

If two or more sequences are compared regarding their sequence identity the comparison only considers a nucleotide or amino acid to be identical if exactly the same nucleotide or amino acid is present at a certain position. Especially for amino acid sequence comparisons it has to be clearly distinguished between sequence identity and sequence homology. In the present patent application in the context of sequence comparisons always sequence identity is meant, not sequence homology, except if the contrary is expressly mentioned. Homology means for example that the amino acid at a certain position within a sequence is not identical but is only similar regarding its chemical and/or biological and/or physical characteristics. Examples for such amino acids, which commonly are regarded as homologue are:

positively charged amino acids: Arginine, Histidine, Lysine, or negatively charged amino acids: Aspartic Acid, Glutamic Acid, or polar, uncharged amino acids: Serine, Threonine, Asparagine, Glutamine, or Aromatic amino acids: Phenylalanine, Tyrosine, Tryptophan, or aliphatic amino acids: Glycine, Alanine, Valine, Leucine, Isoleucine, or sulfur-containing amino acids: Cysteine, Methionine, or heterocyclic secondary alpha-amino acid: Proline Sequence alignments or sequence differences for example can be determined with various methods, software and algorithms. Such determinations can be done for example using the web-services of the National Institute of Health (NIH), or using the web-services of the European Bioinformatics Institute (EMBL-EBI). "Sequence identity" or "% identity" refers to the percentage of residue matches between two protein, polypeptide, peptide, amino acid, or nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Because of the different algorithms and software settings it is possible that an alignment or sequence comparison of the same two sequences using different software/ algorithms does not give exactly the same result. Therefore, the software and the software settings have to be given, in order to clearly define how results were obtained.

For purposes of the present invention, the sequence identity between two sequences is determined using the NCBI BLAST program version 2.6.0 (Jan. 10, 2017), BLAST=Basic Local Alignment Search Tool, (Altschul et al., Nucleic Acids Res. (1997) 25:3389-3402). As reference sequence is always used the shorter one of the two to be compared promoter sequences. For example if a certain promoter $X_{short}$ of a sequence length of 100 nucleotides is aligned/compared to the same promoter $X_{long}$, which is the same promoter but a longer version of said promoter of 200 nucleotides, a comparison of the two sequences $X_{short}$ and $X_{long}$ gives the following result: If the shorter sequence $X_{short}$ is the reference sequence, which is compared to the longer version of the sequence namely $X_{long}$, then $X_{short}$ is 100% identical to $X_{long}$. If however the longer sequence $X_{long}$ is the reference and compared to $X_{short}$, then $X_{long}$ is only 50% identical to $X_{short}$. Consequently in the present patent application a comparison of sequence $X_{short}$ and sequence $X_{long}$ would always be regarded as 100% identical not 50% identical, because as a reference sequence within this applications is always used the shorter one of the to be compared promoter sequences.

Sequence identity of two amino acid sequences for example can be determined with blastp, set at the following default algorithm parameters: "Max target sequences"=100, "Short queries"="Automatically adjust to parameters for short input sequences", "Expect threshold"=10, "Word size"=6, "Max matches in a query range"=0, "Matrix"=BLOSUM62, "Gap Costs"="Existence: 11 Extension: 1", "Compositional adjustments"="Conditional compositional score matrix adjustment", Filters and Masking: "Low complexity regions", "Mask for lookup table only", "Mask lower case letters", all three filters deactivated.

Sequence identity of two nucleotide acid sequences for example can be determined with blastn, set at the following default algorithm parameters: "Max target sequences"=100, "Short queries"="Automatically adjust to parameters for short input sequences", "Expect threshold"=10, "Word size"=28, "Max matches in a query range"=0, "Match/ Mismatch Scores"=1,−2, "Gap Costs"="Linear", Filters and Masking: "Low complexity regions", "Mask for lookup table only", both filters activated.

If nucleotides of nucleotide sequences are mentioned the abbreviations A, T, G, C, and U represent the different nucleotides. Whenever T or U as a nucleotide is mentioned T and U can be exchanged for each other, unless this does not make sense from an experimental or scientific point of view. If the terms nucleotide sequence, polynucleotide etc. are used within the application always DNA and/or RNA, or deoxynucleic acids and/or deoxyribonucleic acids are meant to the extent this makes sense from an experimental or scientific point of view.

The use of the degenerated genetic code allows to have several different nucleotide sequences, all of which code for an identical amino acid sequence. The amount of differences between two nucleotide sequences coding for the same mature protein depends on the amino acid sequence of said mature protein. Very simplified, all amino acids are coded by three nucleotides, and the last nucleotide of the codon of most amino acids can vary between Guanine (G), Cytosine (C), Alanine (A), and Thymidine (T). So most Amino acids have four different codons, each of which codes for the same amino acid. As a consequence a mature polypeptide of for example 100 amino acids length is coded by 300 nucleotides, and every third nucleotide can be mutated without changing the amino acid sequence. So in this simplified model 100 nucleotides of the total 300 nucleotides can be exchanged due to the degenerated code without changing the corresponding amino acid sequence. This simplified model results in a maximal theoretical nucleotide sequence difference of 33.3%. If it is desired that 50% of the maximal theoretical nucleotide sequence difference is desired, 50% of these 100 nucleotides, namely 50 nucleotides can be exchanged for other nucleotides, resulting in a nucleotide sequence difference of 16.65%.

In reality this calculation is a little bit more difficult. For example the maximal nucleotide sequence of the following peptide sequence can be calculated as follows:

TABLE 1

| Pep1 (SEQ-ID NO.: 9) | Arg | Ser | Leu | Leu | Ser | Leu | Arg | Ser | Ser | Leu | Ratio |
|---|---|---|---|---|---|---|---|---|---|---|---|
| | xTx | xxx | xTx | xTx | xxx | xTx | xTx | xxx | xxx | xTx | 24/30 |
| Pep2 (SEQ-ID NO.: 10) | Met | His | Val | Ala | Trp | Asn | Asp | Met | Cys | Pro | Ratio |
| | AUG | CAx | GTx | GCx | TGG | AAx | GAx | AUG | TGx | CCx | 7/30 |

Serine (Ser) is coded by TCT, TCA, TCC, TCG, AGT, AGC
So the codon of Ser can vary in position 1, 2 and 3 = xxx
Leucine (Leu) is coded by CTT, CTA, CTC, CTG, TTA, TTG
So the codon of Leu can vary in position 1 and 3 = xTx
Arginin (Arg) is coded by CGT, CGA, CGC, CGG, AGA, AGG
So the codon of Arg can vary in position 1 and 3 = xTx As a result the nucleotide sequence of the sample peptide Pep1 has 24 out of 30 nucleotide positions, which can be exchanged by at least one different nucleotide without changing the amino acid sequence. The maximal different nucleotide sequence is 24/30=0.8, meaning 80% maximal nucleotide sequence difference.

If one calculates the same for Peptide Pep2 the result is as follows: Methionine and Tryptophan each have only one codon, meaning that no nucleotide can be exchange without changing the amino acid coded. All other amino acids have two, three or four different codons, but all codons have the first and second nucleotide fixed whereas only the third nucleotide can vary.

As a result the nucleotide sequence of Pep2 has only 7 out of 30 nucleotides, which can be exchanged without changing the amino acid sequence coded. The maximal different nucleotide sequence is therefore 7/30=0.23, meaning 23% maximal nucleotide sequence difference.

So the maximal variation of the nucleotide sequence without changing the amino acid sequence highly depends on the amino acid sequence of the POI. If for example it is intended, that the nucleotide difference should be 50% of the maximum nucleotide sequence difference possible in order to still get an identical mature amino acid sequence this 50%-value for Pep 1 would be 50% of 80%=40%, whereas the 50%-value for Pep2 would be 50% of 23%=11.5%.

Using this strategy a skilled person can easily calculate for any POI the % of variation from the mature nucleotide sequence, which is possible, if for example 50% of the maximum nucleotide sequence difference possible, in order to get an identical mature amino acid sequence of the POI is intended.

"Genetic stability" or alternatively also termed "genomic stability" according to the invention means that the nucleic acid sequence belonging to the genome of a host cell does not "significantly change" over time, e.g. over a certain number of cell generations or cell divisions of said host cell. Such changes can for example result from homologous recombination events of very similar or identical nucleotide sequences. If for example several identical copies of an expression cassette have been integrated into the genome of a host cell, the likelihood that later on these identical nucleotide sequences recombine with each can increase. Such recombination events for example can result in partial or complete deletion, duplication or multiplication of said expression cassettes. Also re-arrangement of said expression cassettes changes of their location within a chromosome or changes regarding their orientation within a chromosome can occur.

"Significantly change" regarding genetic stability means larger rearrangements of the genome of a host cell, such as deletion, duplication, multiplication, re-arrangement, re-location, partial deletion, partial duplication, partial-multiplication, partial re-arrangement, partial re-location, etc. of nucleotide sequences within the genome of the host cell. Such genetic instabilities can preferably effect nucleotide sequences of expression cassettes introduced into the host cell genome in order to express a POI by said host cell. A significant change of the host cell genome can effect a nucleotide sequence of at least 5 to 20, preferably at least 5 to 100, more preferably at least 5 to 500, most preferably at least 5 to 1500 nucleotide length.

Limited numbers of point mutations of for example expression cassettes, are only regarded as minor changes of the genome of the host cell. Such limited numbers of point mutations are common in nature, and normally can occur in any cell over time especially during cell division and cell ageing. Such limited numbers of point mutations are not regarded as impaired genetic stability and are not regarded as significantly change nucleic acid sequences.

The genome of the host cell according to the invention is regarded as the chromosomes, the chromosomes of mitochondria, and extra-chromosomal plasmids present in the host cell prior to introduction of expression cassettes coding for a POI. According to the invention nucleic acids such as mRNA, tRNA, rRNA, etc. are not regarded as belonging to the genome of said host cell.

Not all types of such nucleic acids belonging to the genome are present in all types of host cells. For example bacterial host cells usually do not contain mitochondrial chromosomes.

"Cell generations" according to the inventions means that one cell generation is the doubling of the number of a certain host cell. Depending on the type of host cell one cell generation may take only a few minutes, for example in the case of a bacterial host cells, or may take several hours or even several days, for example in the case of mammalian cells.

"Single chain protein" according to the invention includes proteins which comprise only one single amino acid chain. Proteins which are modified during posttranslational processing from a single chain precursor but which consist of several amino acid chains, eventually connected via disulphide bridges, such as for example human insulin, are still regarded as single chain proteins according to this invention. Such single chain proteins, which after posttranslational processing comprise two or more amino acid chains, can be easily identified by analysing the coding nucleotide sequence of said single chain protein for its open reading frame. An open reading frame is a continuous stretch of codons that do not contain a stop codon (usually a TAA, TAG or TGA in the case of deoxyribonucleic acids, or UAA, UAG or UGA in the case of ribonucleic acids) within a nucleotide sequence. The open reading frame may code for a single polypeptide chain which later on during processing of said polypeptide chain may be processed into a protein comprising two or more polypeptide chains. Such a protein, according to this invention, is still regarded as single chain protein.

"Vector" according to the invention preferably is a circular, double-stranded deoxy-poly-nucleotide, which may be linearized, for example by digestion with a restriction endonuclease which recognizes only on site within the nucleotide sequence of said vector. A vector may be manufactured by molecular biologic techniques, or may be chemically or enzymatically synthesized, using techniques known in the art.

"Resistance gene" or "resistance marker" according to the invention means a gene coding for a protein rendering a host cell resistant to the activity of toxic substance, preferably an antibiotic.

"Metabolic marker" according to the invention usually means a gene coding for a protein providing the host cell with the ability to synthesize a certain metabolite such as for example a certain amino acid, which metabolite is needed for growth or survival of the host cell.

"Selectable marker" according to the invention usually is a resistance gene, a metabolic marker, or an auxotrophic marker, but can also be for example a gene, which allows to recognize a host cell harbouring said gene, for example a gene coding for a coloured protein, or coding for an enzyme which generates or metabolizes a coloured substance, or an enzyme such as luciferase which emits light when metabolizing a substrate, etc.

A kit according to the invention is a set of materials suitable to for example to express a recombinant protein or a POI. A kit typically might contain materials such as host cells, protein expression vectors, PCR-primers suitable to detect parts of said protein expression vectors, culture media suitable to grow said host cells, chemicals and buffers suitable to transfect vectors into host cells, enzymes to perform PCR-reactions, enzymes to cut circular vectors into linear vectors, instruction manuals which explain how to use said kit or which explain for what purposes said kit is suitable, etc.

"Derivatives of cells" or derivatives of cell lines, or "derivatives of host cells" or "derivatives of host cell lines" are cells which originated from cells or host cells, wherein said cells or host cells have been manipulated in a way to, for example, contain or lack certain resistance genes, to contain or lack certain metabolic genes, to contain or lack certain genes which allow to distinguish said cells or host cells from their corresponding non-modified cells or host cells. Usually derivative of cells or host cells are genetically almost identically to the corresponding cell or host cell from which they originated (their mother cells), but are only different regarding one or very few genes, such as the types of genes mentioned above.

DETAILED DESCRIPTION OF THE INVENTION

The host cells according to the invention in principal can be any type of cells, such as cell lines or primary cells or even mixtures of different types of cells or tissue samples, organs or whole multicellular organisms. Preferably the cells are prokaryotic or eukaryotic cell lines.

If prokaryotic cells are used according to the invention, the cells are preferably bacteria such as *Escherichia coli*, such as BL21, BL21(DE3), W3110, MG1655, RB791, RV308, or *Bacillus megaterium*, such as QM B1551, PV361, DSM319, or *Pseudomonas*, such as *P. aeruginosa, P. putida, P. fluorescens, P. alcaligenes, P. aeruginosa* PAO1-LAC, *P. putida* KT2440, or *Streptomyces*, such as *S. coelicolor* A3, *S. avermitilis, S. griseus, S. scabies, S. lividans* TK24, *S. lividans* 1326. Examples of *E. coli* include those derived from *Escherichia coli* K12 strain, specifically, HMS 174, HMS174 (DE3), NM533, XL1-Blue, C600, DH1, HB101, JM109, as well as those derived from B-strains, specifically BL-21, BL21 (DE3) and the like. In general also derivatives such as modified prokaryotic cells such as bacteria, are suitable for use in the invention. Such modification for example might be the deletion or inactivation of proteases, or deletion or inactivation of other genes.

If eukaryotic cells are use according to the invention, the cells are preferably yeast cells, filamentous fungal cells, insect cells, mammal cells or human cells.

Yeast cells preferably are methylotrophic yeasts (=yeast cells that can utilize methanol as a carbon and energy source) such as *Komagataella pastoris=Pichia pastoris, P. methanolica, H. polymorpha, O. minuta, C. biodinii* or non-methylotrophic yeasts such as *Saccharomyces cerevisiae, Kluyveromyces lactis, P. Stipitis, Yarrowia lipolytica, Z. rouxii, Z. bailii, A. adeninivorans, Kluyveromyces marxianus, Schizosaccharomyces pombe* and *Arxula adeninivorans*. Examples for *Pichia pastoris* strains useful in the present invention are X33 and its subtypes GS115, KM71, KM71H; CBS7435 (mut+) and its subtypes CBS7435 muts, CBS7435 mut$^s$deltaArg, CBS7435 mut$^s$deltaHis, CBS7435 mut$^s$deltaArg, deltaHis, CBS7435 mut$^s$ PDI+, CBS 704 (=NRRL Y-1603=DSMZ 70382), CBS 2612 (=NRRL Y-7556), CBS 9173-9189 and DSMZ 70877, PPS-9010 (available from ATUM, formerly DNA2.0, Newark, CA, USA) and PPS-9016 (available from ATUM, formerly DNA2.0, Newark, CA, USA) as well as mutants thereof. In general also derivatives of such yeast cells, such as for example modified yeast cells, are suitable for use in the invention. Such modification for example might be the deletion or inactivation of yeast proteases, or the deletion or inactivation of other genes such as for example the ssn6-like gene (for details see WO2016139279A1) or the deletion of the so called killer plasmids from the yeast genome, especially from the *P. pastoris* or the *S. cerevisiae* genome (Sturmberger et al., J Biotechnol., 2016, 235:121-131).

Filamentous fungal cells are preferably *Aspergillus* such as, *A. niger, A. oryzae, A. terreus, A. awamori, A. nidulans*, or *Trichoderma* such as, *T. reesei, T. reesei* QM9414, *T. reesei* RUT-C30, *T. reesei* QM6a, T. atroviride, *T. harzianum, T. virens, T. asperellum, T. longibrachiatum*, or *Penicillium* such as *P. purpurogenum, P. funiculosum, Penicillium* (*Talaromyces*) *emersonii, P. camemberti* and *P. roqueforti* and their derivatives Insect cells are preferably Sf9 or Sf21 cells (both from Spondoptera *frugiperda*), High-Five-cells (same as Hi5, same as High-Five BTI-TN-5B1-4) or Tn-368 cells (both from *Trichoplusia ni*), or Se301 cells (from Spondoptera exigua) and their derivatives.

Mammalian cells are preferably CHO (Chinese Hamster Ovary=CHO) cells, such as CHO-K1, CHO-DXB11, CHO-S, CHO-DG44 and their derivatives.

Human cells are preferably HEK293 (Human Embryonic Kidney=HEK) cells, such as HT-1080, PER.C6, HKB-11, CAP and HuH-7 and their derivatives.

Cells and cell lines can be obtained from various sources such as tissue culture collections such as the American Type Culture Collection (ATCC), 10801 University Boulevard, Manassas, VA 20110, USA, Deutsche Sammlung von Mikroorganismen and Zellkulturen GmbH (DSMZ), Inhoffenstraße 7B, 38124 Braunschweig, Germany, Centraalbureau voor Schimmelcultures (CBS), Uppsalalaan 8, 3584 CT Utrecht (Utrecht), Nederland, The Coli Genetic Stock Center (CGSC), 730 Kline Biology Tower, Dept. of Molecular, Cellular, and Developmental Biology, 266 Whitney Ave., PO box 208103, Yale University, New Haven, CT 06520-8103, USA or from commercial vendors such as Merck KGaA, Frankfurter Straße 250, 64293 Darmstadt, Germany, GE Healthcare, Chalfont St Giles, Buckinghamshire, Great Britain, Thermo Fischer Scientific, 168 Third Avenue, Waltham, MA USA 02451, etc.

TABLE 2

Host cells and promoters suitable for use in said cells

| Host cell | Promoter abbreviation | Promoter name | Source of promoter | Constitutive/inducible |
|---|---|---|---|---|
| *Escherichia coli* * BL21 BL21(DE3) W3110 RB791 MG1655 | $p_L$ | Repressor: cI857 | lambda phage | Inducible (T = 42° C.) |
| | lac | Lactose-operon promoter Repressor: lacI$^Q$ | *E. coli* | Inducible (lactose or IPTG) |
| | trp | Tryptophan-operon promoter Repressor: Trp | *E. coli* | Inducible (Tryptophan strvation or IAA) |
| | tac | Hybrid of lac and trp-promoter Repressor: lacI$^Q$ | Artificial promoter | Inducible (lactose or IPTG) |
| | T7* | T7-promoter Repressor: lacI$^Q$ | Bacteriophage T7 | (lactose or IPTG) |
| | T5 | T5-promoter Repressor: lacI$^Q$ | Bacteriophage T5 | (lactose or IPTG) |
| | rhaBAD | Rhamnose-inducible promoter | *E. coli* | Inducible (Rhamnose) |
| *Saccharomyces cerevisiae* | GAP | Glyceraldehyde-3-phosphate dehydrogenase | *S. cerevisiae* | Constitutive |
| | PGK | Phosphoglycerate kinase | *S. cerevisiae* | Constitutive |
| | TPI | Triose phosate isomerase | *S. cerevisiae* | Constitutive |
| | ENO | enolase | *S. cerevisiae* | Constitutive |
| | a-MP | Alpha-mating factor | *S. cerevisiae* | Constitutive |
| | TEF | Translation elongation factor-1a | *S. cerevisiae* | Constitutive |
| | GAL1 to GAL-10 | Upstream Activating Sequence of GAL1 to GAL-10 promoter | *S. cerevisiae* | Induceable (galactose) |
| | ADH2 | Alcohol dehydrogenase 2 | *S. cerevisiae* | Induceable (ethanol) |
| | PHO5 | Acid phosphatase | *S. cerevisiae* | Induceable (phosphate) |
| | CUP1 | Copper-binding metallothionein | *S. cerevisiae* | Induceable (copper) |
| *Pichia pastoris*** | GAP | Glyceraldehyde-3-phosphate dehydrogenase | *P. pastoris* | Constitutive |
| | TEF | Translation elongation factor-1a | *P. pastoris* | Constitutive |
| | PGK | Phosphoglycerate kinase | *P. pastoris* | Constitutive |
| | AOX1 | Alcohlol oxidase | *P. pastoris* | Induceable (methanol) |
| | FLD1 | Formaldehyde dehydrogenase 1 | *P. pastoris* | Induceable (methanol) |
| | LLP** | Lektin-like protein | *P. pastoris* | Constitutive |
| Insect cells: Sf9 Sf21 Tn-368 Hi5 Se301 | polh | polyhedrin gene promoter | AcMNPV | virus induced |
| | p10 | | AcMNPV | virus induced |
| | 39K | p39 capsid protein promoter (= vp39 or 39K promoter) | AcMNPV | virus induced |
| | pB2 | hexamerin-derived promoter pB2 | Trichoplusiani | virus induced |
| | orf46 | polyhedron envelope protein | SeMNPV | virus induced |
| | p6.9 | basic protein promoter (=p6.9 promoter) | AcMNPV | virus induced |

TABLE 2-continued

Host cells and promoters suitable for use in said cells

| Host cell | Promoter abbreviation | Promoter name | Source of promoter | Constitutive/ inducible |
|---|---|---|---|---|
| | gp64 | glycoprotein p64 promoter (=GP64/67) | AcMNPV | virus induced |
| | ie-1 | immediate-early promoter-1 | AcMNPV | Constitutive |
| Chinese Hamster Ovary cells (CHO) | CMV | CMV-promoter | human cytomegalo virus | Constitutive |
| | EF1a (=EF1α) | Human elongation factor-1 alpha | Homo sapiens | Constitutive |
| | SV40 | SV40 promoter | Simian virus 40 | |
| | CVM + enhancer + RK Intron | CMV-promoter and its RK intron | human cytomegalo virus | Constitutive |
| | SV40 + enhancer | SV40 promoter and its enhancer | Simian virus 40 | |
| | EF1a + EF1a first intron | Human elongation factor-1 alpha and its first intron | Homo sapiens | Constitutive |
| | PGK | Phosphoglycerate kinase | *P. pastoris* | Constitutive |
| | BG | Beta-globulin | *Oryctolagus cuniculus* | |
| | RSV | Rous Sarcoma Virus LTR Promoter | Rous Sarcoma Virus | Constitutive |
| Human Embryonic Kidney cells 239 (HEK293)[9] | CMV | Major immediate early promoter | *Cytomegalo virus* | Constitutive |
| | EF1a | Human elongation factor-1 alpha | Homo sapiens | Constitutive |
| Yarrowia lipolytica | TEF | Translation elongation factor-1a | *Y. lipolytica* | Constitutive |
| | RPS7 | Ribosomal protein S7 | *Y. lipolytica* | Constitutive |
| | XPR2 | Alkaline extracellular protease | *Y. lipolytica* | Constitutive |
| | hp4d | Derivative of XPR2 | *Y. lipolytica* | Constitutive |
| | POX2 | acyl-CoA oxidase 2 | *Y. lipolytica* | Induceable (fatty acids, alkanes) |
| | POT1 | 3-oxo-acyl-CoA thiolase | *Y. lipolytica* | Induceable (fatty acids, alkanes) |
| | ICL1 | Isocitrate lyase 1 | *Y. lipolytica* | Induceable (fatty acids, alkanes) |
| Aspergillus | glaA | Glucoamylose | *A. niger* | Induceable (maltose, starch) |
| | alcA | Alcohol dehydrogenase | *A. nidulans* | Induceable (ethanol) |
| | alC | Alcohol dehydrogenase | *A. nidulans* | Induceable (ethanol) |
| | exIA | Endoxylanase | *A. awamori* | Induceable (xylose) |
| | thiA | Involved in thiamine biosynthesis | *A. oryzae* | Induceable (thiamine-dependant) |
| | aphA | Acid phosphatase | *A. nidulans* | Induceable (phosphate) |
| | sodM | Superoxide dismutase | *A. oryzae* | Induceable (H2O2) |
| | gpdA | Glyceraldehyde-3-phosphate | *A. nidulans* | Constitutive |
| | adhA | Alcohol dehydrogenase | *A. nidulans* | Constitutive |
| | tpiA | Trioephosphate isomerase | *A. nidulans* | Constitutive |
| | pkiA | Protein kinase A | *A. oryzae* | Constitutive |
| | gdhA | Glutamate dehydrogenase | Awarmori, *A. niger* | Constitutive |
| | oliC | ATP synthase | *A. nidulans* | Constitutive |
| | tef1 | Translation elogation factor | *A. oryzae* | Constitutive |
| | oliC/acuD | Hybrid promoter | Hybrid promoter | Induceable (acetate) |

TABLE 2-continued

Host cells and promoters suitable for use in said cells

| Host cell | Promoter abbreviation | Promoter name | Source of promoter | Constitutive/inducible |
|---|---|---|---|---|
| Trichoderma | cbh1 | Cellobiohydrolase 1 | Trichoderma reesei (=T. reesei) | Induceable (cellulose, sephorose, lactose) |
| | cbh2 | Cellobiohydrolase 2 | T. reesei | Induceable (cellulose, sephorose, lactose) |
| | xyn2 | Cylanase | T. reesei | Induceable (cellulose, sephorose, lactose) |
| | egl2 | Glycosyl hydrolase | T. reesei | Data not available |
| | rp2 | Ribosomal protein | T. reesei | Constitutive |
| | pgk1 | Pyruvate kinase | T. reesei | Constitutive |
| | pkiA | Protein kinase A | T. reesei | Constitutive |
| | pdC | Pyruvate decarboxylase | T. reesei | Constitutive |
| | tef1 | Translation elongation factor | T. reesei | Constitutive |
| | eno | Enolase | T. reesei | Constitutive |
| Bacillus megaterium | xylA | Xylose-induceable promoter | Bacillus megaterium (= B. megaterium) | Induceable (sucrose) |
| | K1E | K1E-RNA-polymerase dependent promoter | E. coli phage K1E | Induceable (xylose) |
| | T7 | T7 RNA polymerase promoter | bacteriophage T7 | Induceable (IPTG) |
| | SP6 | SP6 RNA polymerase promoter | Salmonella typhimurium phage SP6 | Induceable (xylose) |
| | PamyL | starch-inducible promoter PamyL | Bacillus amyloliquefaciens | Induceable (starch) |
| | sacB | sucrose-inducible promoter | B. megaterium | Induceable (succrose) |
| | cbi | promoter of cbi operon | B. megaterium | Constitutive |

\* depending on the promoter used, certain cell types need specific proteins or factors to be present in said cell, in order to enable said promoter to work, for example in the case of the T7 promoter the T7-RNA-polymerase, which is not present in all types of cells but which can be transfected into said cells if needed.
\*\* in order for the LLP-promoter to work, the ssn6-gene needs to be inactivated or deleted (for details see WO2016139279A1)

TABLE 3

Host cells and signal sequences suitable for use in said cells

| Host Cell | Signal Peptide | Source of Signal Peptide | Organism of Signal Peptide |
|---|---|---|---|
| E. coli | OmpA | outer membrane protein A | E. coli |
| | MalE | maltose-binding periplasmic protein | E. coli |
| | LamB | maltose outer membrane porin (maltoporin) | E. coli |
| | PhoE | outer membrane pore protein E | E. coli |
| | PhoA | alkaline phosphatase | E. coli |
| | STII | heat-stable enterotoxin II | E. coli |
| | MBP | maltose-binding protein | E. coli |
| | native signal peptide of POI* | native signal peptide of POI | organism of the POI |
| Insect sells | pg64/67 | glycoprotein p64/67 (=GP64/67) | AcMNPV |
| | melittin | melittin signal sequence | honeybee |
| | native signal peptide of POI | native signal peptide of POI | organism of the POI |

TABLE 3-continued

Host cells and signal sequences suitable for use in said cells

| Host Cell | Signal Peptide | Source of Signal Peptide | Organism of Signal Peptide |
|---|---|---|---|
| S. cerevisiae | MF-α1 | Mating Factor alpha 1 | Saccharomyces cerevisiae |
|  | tPA | Tissue plasminogen activator | Homo sapiens |
|  | Levanase signal | levanase | B. subtilis |
|  | Killer toxin signal | killer toxin | K. lactis |
|  | SUC2 | invertase | Saccharomyces cerevisiae |
|  | native signal peptide of POI | native signal peptide of POI | organism of the POI |
| P. pastoris | LLP | lectin-like protein | Pichia Pastoris |
|  | HSA | serum albumin | Homo sapiens |
|  | MF-α1 | Mating Factor alpha 1 | Saccharomyces cerevisiae |
|  | MF-α2 | Mating Factor alpha 2 | Saccharomyces cerevisiae |
|  | PHO | acid phosphatase | Pichia Pastoris |
|  | SUC2 | invertase | Saccharomyces cerevisiae |
|  | native signal peptide of POI | native signal peptide of POI | organism of the POI |
| CHO | synthetic (var1) | synthetic signal peptide, variation 1 | artificial |
|  | synthetic (var2) | synthetic signal peptide, variation 2 | artificial |
|  | synthetic (var2) | synthetic signal peptide, variation 3 | artificial |
|  | native signal peptide of POI | native signal peptide of POI | organism of the POI |
| HEK293 | native signal peptide of POI | native signal peptide of POI | organism of the POI |
|  | synthetic (var1) | synthetic signal peptide, variation 1 | artificial |
|  | synthetic (var2) | synthetic signal peptide, variation 2 | artificial |
|  | synthetic (var2) | synthetic signal peptide, variation 3 | artificial |
| Bacillus megaterium | $SP_{lipA}$ | lipase A |  |
|  | $SP_{sacB}$ | levansucrase |  |
|  | $SP_{native}$ | dextransuccrase | Leuconostoc mesenteroides |
|  | $SP_{native}$ | endoglucanase | Bacillus amyloliquefaciens |
|  | $SP_{native}$ | keratinase | Bacillus licheniformis |
|  | native signal peptide of POI | native signal peptide of POI | organism of the POI |

* not in all cases the original signal peptide of the POI will work in a certain type of cells, however if the cells are similar enough, often the native signal sequence will work.

TABLE 4

Host cells and termination sequences suitable for use in said cells

| Host Cell | Termination Sequence | Source of Termination sequence | Organism of Termination Sequence |
|---|---|---|---|
| E. coli | stop codon | UAA-stop codon | E. coli |
|  | prolonged stop codon | UAAU-stop codon | E. coli |
|  | consecutive stop codons | UAAUAA stop codon | E. coli |
| S. cerevisiae | ADH | Alcohol dehydrogenase terminator | S. cerevisiae |
|  | AOD | alcohol oxidase terminator | S. cerevisiae |
|  | cyc1 | cytochrome c1 terminator | S. cerevisiae |

TABLE 4-continued

Host cells and termination sequences suitable for use in said cells

| Host Cell | Termination Sequence | Source of Termination sequence | Organism of Termination Sequence |
|---|---|---|---|
| P. Pastoris | LLP | Lectin-like protein terminator | Pichia Pastoris |
| | ADH | Alcohol dehydrogenase terminator | S. cerevisiae |
| | AOD | alcohol oxidase terminator | S. cerevisiae |
| | cyc1 | cytochrome c1 terminator | S. cerevisiae |
| Insect cells | SV40 | SV40 poly-adenylation signal | Simian virus 40 |
| | ie-1 | immediate-early 1 terminator | AcMNPV |
| | bGH | bovine Growth Hormone poly-adenylation signal | Bos taurus |
| CHO | bGH | bovine Growth Hormone poly-adenylation signal | Bos taurus |
| | BG (=rabbit BG) | Beta globulin poly-adenylation signal | Oryctolagus cuniculus |
| | synthetic | synthetic poly-adenylation signal | artificial |
| | SV40 | SV40 poly-adenylation signal | Simian virus 40 |
| | SV40early | Early SV40 poly-adenylation signal | Simian virus 40 |

Molecular biologic techniques, such as cloning, transfection, determination of copy numbers of the transfected expression cassettes, design and chemical synthesis of vectors, use and choice of vector elements such as origins of replications, antibiotic resistances, selection markers, promoters, signal sequences, terminators, etc., cell culture techniques, protein expression techniques including viral techniques for example used for the Bacculovirus system, etc., quantitative and semi-quantitative determination of protein expression, etc. are all standard laboratory methods and are known to the skilled person. Protocols can be obtained from standard text books and laboratory manuals, for example from M. R. Green, J. Sambrook, 2013, Molecular cloning: a laboratory manual, Cold Spring Harbor, N.Y.; Current Protocols in Protein Science, John Wiley & Sons Inc. ISSN 1934-3655; Current Protocols in Molecular Biology, John Wiley & Sons Inc. ISSN 1934-3639; Advanced Technologies for Protein Complex Production and Characterization, Editor M. Cristina Vega, Springer, 2016, ISSN 0065-2598; Bacculovirus and Insect Cell Expression protocols, Third Edition, Editor David W. Murhammer, Humana Press, 2016, ISSN 1064-3745; Recombinant Gene Expression, Reviews and Protocol, Third Edition, Editor A. Lorence, Humana Press, ISSN 1064-3745, etc.

Measuring of Host Cell Expression of POI

In order to determine whether a host cell transfected with different expression cassettes according to the invention expresses higher quantities of said POI as compared to a host cell comprising the same number of expression cassettes with identical expression cassette sequences, there are known a number a standard testing systems, such as ELISA (enzyme-linked immunosorbent assay), ELIspot assays (Enzyme Linked Immuno Spot Assay), surface plasmon resonance assays (Biacore Life Science, now GE Healthcare), protein chip assays, quantitative reverse-transkriptase PCR (qRT-PCR), desitometric measurement of western-blots, coomassie blue or silver-stained SDS-PAGE gels, quantitative mass spectrometry, calculation of the peak-area under the corresponding POI-peak of a chromatogram of a POI sample, etc.). Suitable protocols for carrying out said methods are known to the skilled person and can be for instance found in M. R. Green, J. Sambrook, 2013, Molecular cloning: a laboratory manual, Cold Spring Harbor, N.Y., or in Current Protocols in Protein Science, John Wiley & Sons Inc. ISSN 1934-3655.

Measuring of Genetic Stability

Genetic stability for example can be measured by determining the copy number of different expression cassettes according to the invention in the host cells of the invention as compared to the copy number of identical expression known in the art in cassettes in host cells. Copy numbers of expression cassettes for example can be determined by quantitative PCR (qPCR). Primers for qPCR can be designed in a way that they amplify the complete or a part of the expression cassettes. If the copy number of the expression cassettes alters after a number of cell generations, this proofs genomic instability. Furthermore the sequence length of the qPCR products can be determined by for example agarose gel electrophoresis. If deletions or duplications of parts of the expression products occurred the sequence length of the qPCR products is altered accordingly, which also indicates genomic instability. Other methods to determine copy numbers of expression cassettes are for example are Southern blots or Fluorescence In Situ Hybridization (FISH). Suitable protocols for carrying out said method are known to the skilled person and can be for instance found in M. R. Green, J. Sambrook, 2013, Molecular cloning: a laboratory manual, Cold Spring Harbor, N.Y., or in Current Protocols in Molecular Biology, John Wiley & Sons Inc. ISSN 1934-3639.

BRIEF DESCRIPTION OF THE FIGURES

FIG. 1: Vector maps of the vectors used for transfection of yeast cells (*Pichia Pastoris*), wherein the vector comprise 1, 2, 3 or 4 expression cassettes for the POI and wherein within one vector for each POI expression cassette there are always used different sequences for the promoter sequence, the signal sequence, the GOI sequence (different coding sequences but which result, due to the degenerated genetic code, always in the same amino acid sequence of the POI; GOI termed variant 1 to variant 4, which are abbreviated var1 to var4), and the terminator sequence. Every yeast vector comprises as the vector back-bone a Zeocin antibiotic resistance expression cassette comprising the hybrid-promoter working in yeast as well as in *E. coli* (pILV5 combined with pEM72), followed by the coding sequence of the antibiotic resistance of Zeocin (ZeoR), followed by the Alkohol Oxidase terminator (AODTT), followed by the origin of replication of pUC (pUC ori). Only in the case of Y392_1 xGOI the pUC ori is followed by the lectin-like protein terminator sequence (LLPTT).

FIG. 1 A:

Yeast vector Y391_1 xGOI in addition to vector back bone contains the following expression cassette for a GOI, which in this case is a single-chain antibody (scFV):

Lectin-like protein promoter (pLLP), as a gene of interest (GOI) a single-chain antibody (scFv_var4), alcohol dehydrogenase terminator sequence (ADHTT)

FIG. 1B:

Yeast vector Y393_2 xGOI in addition to vector back bone contains the following expression cassette for a GOI, which in both cases codes for the same amino acid sequence of a single-chain antibody (scFV):

Glyceraldehyde-3-phosphate dehydrogenase promoter (pGAP), Mating factor alpha 2-signal sequence (MFa2SS), as a gene of interest variation 1 of the same single-chain antibody (scFv_var 1), lectin-like protein terminator sequence (LLPTT)

Lectin-line protein promoter (pLLP), as a gene of interest variation 2 of the same single-chain antibody (scFv_var 4), alcohol dehydrogenase terminator sequence (ADHTT)

FIG. 1C:

Yeast vector Y394_3 xGOI in addition to vector back bone contains the following expression cassette for a GOI, which in in all three case codes for the same amino acid sequence of a single-chain antibody (scFV):

Alcohol dehydrogenase promoter (pADH), human serum albumin signal sequence (HSASS), single-chain antibody, variant 2 (scFv_var2), cytochrome c1 terminator sequence (cyc1TT)

Glyceraldehyde-3-phosphate dehydrogenase promoter (pGAP), mating factor alpha 2-signal sequence (MFa2SS), single-chain antibody, variant 1 (scFv_var1), lectin-like protein terminator sequence (LLPTT)

Lectin-like protein promoter (pLLP), lectin-like protein signal sequence (LLPSS), single-chain antibody, variant 4 (scFv_var4), alcohol dehydrogenase terminator sequence (ADHTT)

FIG. 1D:

Yeast vector Y395_4 xGOI in addition to vector back bone contains the following expression cassette for a GOI, which in in all four case codes for the same amino acid sequence of a single-chain antibody (scFV):

Alcohol dehydrogenase promoter (pADH), human serum albumin signal sequence (HSASS), single-chain antibody, variant 2 (scFv_var2), cytochrome c1 terminator sequence (cyc1TT)

Glyceraldehyde-3-phosphate dehydrogenase promoter (pGAP), mating factor alpha 2-signal sequence (MFa2SS), single-chain antibody, variant 1 (scFv_var1), lectin-like protein terminator sequence (LLPTT)

Lectin-like protein promoter (pLLP), lectin-like protein signal sequence (LLPSS) single-chain antibody, variant 4 (scFv_var4), alcohol dehydrogenase terminator sequence (ADHTT)

Transelongationfactor-promoter (pTEF), mating factor alpha 4-signal sequence (MFa4SS), single-chain antibody, variant 3 (scFv_var3), alcohol oxidase terminator sequence (AOXTT)

FIG. 2:

Sequences of the expression vectors from FIG. 1.
A) Yeast vector Y391_1 xGOI (SEQ-ID NO.: 1)
B) Yeast vector Y393_2 xGOI (SEQ-ID NO.: 2)
C) Yeast vector Y394_3 xGOI (SEQ-ID NO.: 3)
D) Yeast vector Y395_4 xGOI (SEQ-ID NO.: 4)

FIG. 3:

Vector maps of the vectors used for transfection of mammalian cells (CHO cells), each vector comprising a single expression cassette, wherein the expression cassettes comprise as a GOI the sequence of a fusion protein consisting of a constant region of an antibody fused to the ligand-binding domain of a TNF-receptor 2. Each vector furthermore comprises the metabolic selection marker dihydrofolate reductase (DHFR), an enzyme which for example allows CHO (chinese hamster ovary) cells to grow in cell culture medium lacking thymidine, thereby allowing to select CHO (or other cells) transfected with DHFR-comprising vectors from non-transfected cells. Furthermore each vector comprises the sequence of the neomycin resistance gene (NeoR), which allows to select transformed cells by using the antibiotic neomycin. Furthermore each vector comprises another antibiotic resistance gene selected from Ampicillin Resistance (AmpR), Spectromycin Resistance (SpectR) and Chloramphenicol Resistance (CmR). Each vector comprises a different promoter, a different signal sequence and a different terminator sequence within the expression cassette for the GOI.

FIG. 3 A depicts the vector pNT-MG001. Details of the vector elements are shown in Table 7.

FIG. 3 B depicts the vector pNT-MG002. Details of the vector elements are shown in Table 7.

FIG. 3 C depicts the vector pNT-MG003. Details of the vector elements are shown in Table 7.

FIG. 3 D depicts the vector pNT-MG004. Details of the vector elements are shown in Table 7.

FIG. 4:

Sequences of the expression vectors from FIG. 3.
A) Mammalian vector pNT-MG001 (SEQ-ID NO.: 5)
B) Mammalian vector pNT-MG002 (SEQ-ID NO.: 6)
C) Mammalian vector pNT-MG003 (SEQ-ID NO.: 7)
D) Mammalian vector pNT-MG004 (SEQ-ID NO.: 8)

EXAMPLES AND METHODS

Methods for *Pichia Pastoris* Cells

Generation of yeast vectors: The set of vectors contains one vector with one expression cassette, one vector with two different expression cassettes, one vector with three different expression cassettes and one vector with four different expressions cassettes. In the vector set each of the four different expression cassettes has a different nucleotide sequence of the GOI but the resulting POI has an identical mature amino acid sequence, and each of the four different expression cassettes comprises a different promoter nucleotide sequence, a different signal sequence, and a different terminator nucleotide sequence. FIG. 1A to 1D show the vector maps for these vectors, whereas FIG. 2A to 2D and SEQ-ID-NO. 1, 2, 3, and 4 show the complete nucleotide sequences of these vectors.

The four different nucleotide sequence of the POI are designed by use of the degenerated genetic code. The POI is a single chain antibody (scFV, ESBA1845=scFv=single chain variable fragment=artificial antibody fragment comprising a single polypeptide chain including its antigen binding domain). There are used 4 different variants of said scFv termed scFv_var1, scFv_var2, scFv_var3, and scFv_var4, which all code for an identical amino acid sequence but have different nucleotide sequences due to the use of the degenerated genetic code. The promoter sequences used are lectin-like protein promoter from Pichia Pastoris (pLLP), the GAP-promoter (pGAP), the ADH-promoter (pADH), and the TEF-promoter (pTEF). The secretion signal sequences used for the POI are the signal sequence of lectin-like protein from P. pastoris (LLPSS), the signal sequence of mating factor alpha-4 from S. cerevisiae (MFa4SS), the signal sequence of human serum albumin ((HSASS), and the signal sequence of mating factor alpha-2 of S. cerevisiae (MFa2SS). The termination sequences are the Alcohol dehydrogenase (ADHTT), the termination sequence of the lectin-like protein from Pichia Pastoris (LLPTT), the termination sequence of cytochrome c1 terminator (cyc1TT), and the termination sequence of Alcohol oxidase (AOXTT). The yeast cell selection marker used in all vectors is Zeocin-r, expressed by use of the ILV5-promoter, the EM72-signal sequence and the AOD terminator. The pUC ori is used in all yeast expression vectors.

Generation of Vectors

The four different expression vectors are designed as depicted in the vector maps of FIG. 1A to 1D, having the vector sequences as depicted in FIG. 2A to 2D and SEQ ID NOs: 1, 2, 3, and 4. All vectors are chemically synthesized using the DNA2.0 (now ATUM) synthesis service from (ATUM, Newark, CA, USA).

Transfection of P. pastoris

The four different vectors are transfected individually into Pichia pastoris yeast cell SSS1. This yeast cells is described in patent application WO2016139279A1 and is genetically identical to Pichia pastoris CBS 7435 and identical to NRRL Y-11430, except that the ssn6-like gene is disrupted at position 807,480 of chromosome 1 of the P. pastoris CBS 7435 genome by insertion of the expression cassette as described in WO 2016/139270 A1. The complete sequence of CBS 7435 is disclosed in Journal of Biotechnology, published in 2011, Vol. 154, page 312-320 year 2011. The nucleotide sequences are published in GenBank under the following Accession Numbers: Chromosome 1: FR839628.1; Chromosome 2: FR839629.1; Chromosome 3: FR839630.1; Chromosome 4: FR839631.1; Mitochondrion: FR839632.1

Expression of POI in 48-Deep Well Plates, Semi Quantitative Measurement of POI

The transfections are streaked out and individual transformed clones are cultured in synthetic medium. After 70 hours cell culture supernatant is removed from the culture, yeast cells and cell debris is removed from the supernatant by centrifugation and 10 µl of supernatant is loaded and electrophoretically separated on SDS-PAGE (Novex NuPage 4-12%, Invitrogen) gels. After staining with coomassie blue or after silver staining of the SDS-PAGE gels the protein band of the scFv (ESBA1845), having a molecular weight of about 26 kDa is semi-quantitatively determined by scanning and densitometric measurement of the protein band in the gels. The signal intensity gives an estimate of the expression rate of the scFv protein.

Concentration of POI in the supernatant was determined by applying automated capillary electrophoreses (LabChip GXII-Touch, Perkin Elmer, Waltham, MA, USA) according to manufacturer's recommendations.

TABLE 5

Expression of POI, measured by Lab-on-a-chip, Perkin Elmer

| Transfected plasmid | Titer at harvest after 120 h [g/L]] | Fold increase relative to cells transfected with Y391_1xGOI |
|---|---|---|
| Y391_1xGOI (SEQ ID NO: 1) | 1.2 | 1 |
| Y393_2xGOI (SEQ ID NO: 2) | 1.6 | 1.3 |
| Y394_3xGOI (SEQ ID NO: 3) | 1.7 | 1.4 |
| Y395_4xGOI (SEQ ID NO: 4) | 1.7 | 1.4 |

Expression of POI in P. pastoris in Shaker Flasks, Determination of Genetic Stability The individual P. pastoris clones of are either cultured in shaker flasks for 4 weeks. The cell culture is diluted with medium when needed in order to ensure growth of the cells. Before and after this 4 week-culture the copy number of the expression cassettes is determined by for example quantitative PCR (qPCR). Optionally or in addition the sequence of the expression cassettes is determined by sequencing and the correct size of the PCR-amplified nucleic acids is determined by agarose gel electrophoresis, according to methods known in the art. These experiments are performed in order to determine genetic stability of the clones.

Methods for CHO Cells

Generation of Vectors

Four different CHO expression vectors are designed, each coding for the same POI. Two different nucleotide sequences coding for the same amino acid sequence of the POI were used (Etanercept var1 and Etanercept var2). The four different vectors each contain only one expression cassette coding for the same POI, one expression cassette for neomycin (antibiotic selection marker), an expression cassette for another antibiotic resistance, and one expression cassette for DHFR (metabolic selection marker needed for growth of the CHO cell line). Within each of the four different vectors different promoters and terminators are used for the GOI, the neomycin selection marker, and the DHFR, meaning that within a vector different promoters and terminators are used. The nucleotide sequence of the neomycin selection marker and the DHFR is identical in all four vectors. All vectors are chemically synthesized using the GeneArt synthesis service from (Geneart AG, Regensburg, Germany, now belonging to Life Technologies). Details on the vector elements of the different vectors can be found in Table 6, vector maps are depicted in FIGS. 3A to 3D, and the sequences are depicted in FIGS. 4A to 4D and in SEQ ID NOs: 5, 6, 7, and 8.

The CHO-vectors each time comprise only one expression cassette, which expression cassette is different in each of the four vectors. In detail each expression cassette uses a different promoter, a different signal sequence and a different terminator. The POI is always the same. Furthermore each vector comprises an expression cassettes for the metabolic selection marker DHFR (each time coded by the same nucleotide sequence), an expression cassette for the antibiotic selection marker Neomycin R (NeoR) (each time coded by the same nucleotide sequence), and expression cassette coding for another antibiotic selection maker which is either a different selection marker, namely Ampicillin Resistance (AmpR), Spectromycin Resistance (SpectR) or Chloramphenicol Resistance (CmR), or which selection marker is the same selection marker but inserted into the vector in different orientation, e.g. in this case the Ampicillin Resistance marker in two different orientation within vector pNT-MG001 and pNT-MG004. Furthermore all 4 vectors contain as a vector backbone a phage f1 sequence an origin of replication, either pBR322 or p16A, wherein also pBR322 is used in two different orientations within the vectors. An overview of the different vector elements of the mammalian vectors is given in Table 6 below.

TABLE 6

Vector elements of pNT-MB001 to pNT-MB004

| Vector | POI | | | | DHFR | | NeoR | | | | phage |
|---|---|---|---|---|---|---|---|---|---|---|---|
| | p | SS | POI | TT | p | TT | p | TT | Antibiotic | ori | f1 |
| pNT-MG001 (SEQ ID NO: 5) | CMV + enh. + RK intron | var1 | var2 | bGH | SV40 | synthetic | PGK | BG | AmpR** | pBR322* | yes |
| pNT-MG002 (SEQ ID NO: 6) | SV40 + enh. + Hbb intron II | var2 | var2 | SV40 | EF1a | BG | BG | bGH | SpectR | p16A | yes |
| pNT-MG003 (SEQ ID NO: 7) | EF1a + EF1a first intron | var3 | var2 | BG | CMV | bGH | SV40 | SV40early | CmR | pBR322 | yes |
| pNT-MG004 (SEQ ID NO: 8) | CMV + enh. + RK intron | var1 | var1 | SV40 | SV40 | SV40 | SV40 + enh. | synthetic | AmpR | pBR322 | yes | p = promoter, SS = signal sequence, TT = terminator, DHFR = dihydrofolate reductase, NeoR = Neomycin R resistance, ori = origin of replication, var1 = variation 1 of sequence, var2 = variation 2 of sequence, var3 = variation 3 of sequence, AmpR = Ampicillin Resistance, SpectR = Spectromycin Resistance, CmR = Chloramphenicol Resistance
*ori pBR322 has different orientation within vector in pNT-MB001, as compared to pNT-MB003 and pNT-MB004
**the antibiotic resistance AmpR has different orientation within vector in pNT-MB001, as compared to pNT-MB The nucleotide sequences of the vectors pNT-MG001 to pNT-MG004 are given in FIG. 4 A to D and in the sequence protocol, SEQ-ID NO. 5, 6, 7, and 8. As can be seen from Table 6 and from FIG. 3 A to D, pNT-MG001 to pNT-MG003 all contain as a POI the sequence of Etanercept, var2 (=version 2), whereas pNT-MG004 contains Etanercept, var1 (=version 1). var1 and var2 both represent a codon optimized nucleotide sequence, both coding for the same amino acid sequence, however with slightly different codon-usage. The nucleotide sequence of var1 and var2 are more than 90% identical (determined by methods as described elsewhere herein) and the difference is only caused by the use of two different codon-optimizing algorithms for var1 and var2. Only the nucleotide sequence of var2 (used in vectors pNT-MG001 to pNT-MG003) is given in FIG. 4 and in the sequence protocol. For the principle of the invention and for carrying out the described experiments it is not needed to know the var1 nucleotide sequence, as long as it is clear that both, var1 and var2 code for exactly the same amino acid sequence.

Table 7 shows all features of the used expression vectors Y391_1 xGOI, Y393_2 xGOI, Y394_3 xGOI, Y394_4 xGOI, pNT-MG001, pNT-MG002, pNT-MG003, and pNT-MG004.

TABLE 7

Features of the used expression vectors

| Vector name | Seq.-ID NO. | Feature | Position within sequence |
|---|---|---|---|
| Y391_1xGOI | 1 | pUC ori | 1-673 |
| | | LLPPT | 674-1084 |
| | | pLLP | 1091-1701 |
| | | LLPSS | 1709-1783 |
| | | scFv_var4 | 1784-2545 |
| | | ADHTT | 2558-2857 |
| | | pILV5 | 2863-3416 |
| | | pEM72 | 3417-3481 |
| | | ZeoR | 3482-3856 |
| | | AODTT | 3865-4335 |
| Y393_2xGOI | 2 | pUC ori | 1-674 |
| | | pGAP | 698-1183 |
| | | MFa2SS | 1197-1451 |
| | | scFv_var1 | 1452-2216 |
| | | LLPTT | 2223-2633 |

TABLE 7-continued

Features of the used expression vectors

| Vector name | Seq.-ID NO. | Feature | Position within sequence |
|---|---|---|---|
| | | pLLP | 2640-3244 |
| | | LLPSS | 3258-3332 |
| | | scFv_var4 | 3333-4097 |
| | | ADHTT | 4107-4406 |
| | | pILV5 | 4412-4965 |
| | | pEM72 | 4966-5030 |
| | | ZeoR | 5031-5405 |
| | | AODTT | 5414-5884 |
| Y394_3xGOI | 3 | pADH | 4-863 |
| | | HSASS | 877-930 |
| | | scFv_var2 | 931-1695 |
| | | cyc1TT | 1702-1972 |
| | | pGAP | 1984-2469 |
| | | MFa2SS | 2483-2737 |
| | | scFv_var1 | 2738-3502 |
| | | LLPTT | 3509-3919 |
| | | pLLP | 3926-4530 |
| | | LLPSS | 4544-4618 |
| | | scFv_var4 | 4619-5383 |
| | | ADHTT | 5393-5692 |
| | | pILV5 | 5698-6251 |

TABLE 7-continued

Features of the used expression vectors

| Vector name | Seq.-ID NO. | Feature | Position within sequence |
|---|---|---|---|
| | | pEM72 | 6252-6316 |
| | | ZeoR | 6317-6691 |
| | | AODTT | 6700-7170 |
| | | pUC ori | 7191-7864 |
| Y394_4xGOI | 4 | pADH | 4-863 |
| | | HSASS | 877-930 |
| | | scFv_var2 | 931-1695 |
| | | cyc1TT | 1702-1972 |
| | | pGAP | 1984-2469 |
| | | MFa2SS | 2483-2737 |
| | | scFv_var1 | 2738-3502 |
| | | LLPTT | 3509-3919 |
| | | pLLP | 3926-4530 |
| | | LLPSS | 4544-4618 |
| | | scFv_var4 | 4619-5383 |
| | | ADHTT | 5393-5692 |
| | | pTEF | 5698-6397 |
| | | MFa4SS | 6411-6467 |
| | | scFv_var3 | 6468-7232 |
| | | AOX1TT | 7239-7498 |
| | | pILV5 | 7499-8052 |
| | | pEM72 | 8053-8117 |
| | | ZeoR | 8118-8492 |
| | | AODTT | 8501-8971 |
| | | pUC ori | 8992-9665 |
| pNT-MG001 | 5 | syntheticTT | 12-60 |
| | | pCMV + enh + RK intron | 66-1065 |
| | | SS var1 | 1134-1199 |
| | | Etanercept var2 | 1200-2606 |
| | | bGHTT | 2668-2895 |
| | | phage f1 | 2990-3445 |
| | | pPGK | 3509-4063 |
| | | NeoR | 4086-4880 |
| | | BGTT | 4944-5526 |
| | | AmpR | 5884-6744 |
| | | pBR322 ori | 6745-7555 |
| | | pSV40 | 7615-7954 |
| | | DHFR | 8031-8594 |
| pNT-MG002 | 6 | pSV40 + enh + Hbb intron II | 12-1296 |
| | | SS var2 | 1360-1413 |
| | | Etanercept var2 | 1414-2820 |
| | | SV40TT | 2882-3103 |
| | | phage f1 | 3199-3654 |
| | | pBG | 3718-4105 |
| | | NeoR | 4106-4900 |
| | | bGHTT | 4901-5128 |
| | | p16A ori | 5320-6266 |
| | | SpectR | 6267-7277 |
| | | pEF1a | 7582-8765 |
| | | DHFR | 8842-9405 |
| | | BGTT | 10252-10783 |
| pNT-MG003 | 7 | pEF1a + EF1a first intron | 12-1253 |
| | | SS var2 | 1254-1310 |
| | | Etanercept var2 | 1311-2717 |
| | | BGTT | 2765-3347 |
| | | phage f1 | 3442-3897 |
| | | pSV40 | 3961-4311 |
| | | NeoR | 4334-5128 |
| | | SV40earlyTT | 5129-5434 |
| | | pBR322 ori | 5653-6463 |
| | | CmR | 6492-7151 |
| | | pCMV | 7406-7994 |
| | | DHFR | 8071-8634 |
| | | pGHTT | 9480-9707 |
| pNT-MG004 | 8 | pCMV + enh + RK intron | 1-1000 |
| | | SS var1 | 1054-1119 |
| | | Etanercept var1 | 1120-2526 |
| | | SV40TT | 2574-2795 |
| | | phage f1 | 2890-3345 |
| | | pSV40 + enh | 3409-3827 |
| | | NeoR | 3872-4666 |
| | | syntheticTT | 4730-4778 |
| | | AmpR | 5189-6049 |
| | | pBR322 ori | 6050-6860 |
| | | pSV40 | 6927-7265 |
| | | DHFR | 7342-7905 |
| | | SV40TT | 8753-8956 |

SS = signal sequence, TT = terminator, var1 = variant 1, ori = origin of replication, enh = enhancer Obtaining Stable Cell Lines CHO (DHFR) cells are transfected with either an individual vector of the four vectors or with a mix of all four vectors. Stable transfections are performed using Amaxa Nucleofection kit (Lonza AG, Switzerland) following manufacturer's instructions. Briefly, $5 \times 10^6$ CHO cells are transfected with 3 µg of linearized vector DNA per transfection. All vectors are either transfected individually, or as a mix of all four vectors combined. After transfection, growth medium is added and cells are grown in a 10% $CO_2$ atmosphere for 24-48 h at 37° C. with shaking at 110 rpm. Following the recovery of the cells, two selection rounds are performed. Firstly, cells are selected using medium containing G418, followed by selection using methotrexate (MTX) after 90% cell viability is reached. Cells are maintained under MTX selection until cell viability reaches more than 90% (usually 3-4 weeks post-transfection). Throughout the selection period, cells are cultured using fresh medium twice per week. Single cell cloning is performed a using standard limiting dilution cloning approach. Individual clones were selected based on vector copy number (i.e. at least two copies per clone).

From each transfection individual clones are selected and tested for expression rate (titer) of the POI, titer stability of the clone over time, leader peptide cleavage per clone, and genetic stability of the clone over time. With titer is meant concentration (mg/L) of recombinant POI, in this case Etanercept, in tissue culture medium.

Analysis of Vector Copy Numbers in Cell Lines

Integrated vector copy number are assessed using quantitative PCR (qPCR). Relative quantification is used to estimate the number of integrated expression constructs per clone. Repeating the copy number assessment after 3 months is also used to determine, whether copy number of the POI within the individual cell lines is stable over time. Separation of the PCR-products by agarose gel electrophoresis further allows to determine if the size of the PCR-amplified polynucleotide is stable over time, which is another indicator of genetic stability of the individual clones of the cell lines. High resolution melting analysis of PCR-products can be used to confirm the identity of the PCR products.

Analysis of Production of POI by Cell Lines

A 14-day generic fed-batch process is applied for productivity assessment. All fed-batch processes are performed in 100 mL serum-free medium. The medium is inoculated with $4 \times 10^5$ of viable cells/mL and cell culture is incubated in 10% $CO_2$ atmosphere at 37° C. with shaking at 110 rpm (50 mm shaking diameter) and with temperature shift to 33° C. on day 7. Cell concentration and viability are measured using a Vi-Cell XR analyzer. Titers are measured on cultivation days 7, 10 and 14 using Cedex system (Roche Diagnostics Deutschland GmbH, Mannheim, Germany). The measurement is based on a turbidimetric method using antibodies directed against the human Fc region. Harvests are collected at the end of the fed-batch processes and purified using Protein A chromatography.

Analysis of Genetic Stability of the Cell Lines

Individual cell clones are seeded at the density of $3\times10^5$ cell/ml in 75 cm³ flasks in suspension culture in the absence of selective pressure. Productivity testing is done every 6 weeks over a period of 3 months. Expression of POI is measured using standard methods know the skilled person such as ELISA assays, ELISPOT, quantitative western blotting, quantitative mass spectrometry, surface plasmon resonance (e.g. Biacore, Sweden), etc.

Analysis of Signal Peptide Cleavage, by the Cell Lines

Analysis of the correct leader peptide cleavage is done by peptide sequencing using mass spectrometry or Edman degradation. Signal peptide miscleavage can be assessed using intact mass measurement. Protein is first de-glycosylated with N-glycosidase (PNGase) F and subsequently intact mass of the protein is analyzed using LC-MS on a high-resolution mass spectrometer. Masses are identified according to calculated theoretical masses of the protein and signal peptide adducts and proportion of miscleaved signal peptide is calculated from peak intensities.

All methods described or mentioned herein for *Pichia pastoris* yeast cells, CHO mammalian cells, as well as for other types of cells according to the invention, are standard methods know to the skilled person. Such methods are for example described in standard laboratory method manuals such as for instance in M. R. Green, J. Sambrook, 2013, "Molecular cloning: a laboratory manual", Cold Spring Harbor, N.Y., or in "Current Protocols in Molecular Biology", John Wiley & Sons Inc. ISSN 1934-3639 and "Current protocols in Protein Science", John Wiley & Sons Inc. ISSN 1934-3655, or in other titles of the "Current Protocols" series of John Wiley & Sons Inc.

The invention does not include the by chance possible presence of two or more expression cassettes within an individual cell of a cell library, which expression cassettes comprise the same GOI but with a different coding sequence for that same expression cassette, wherein said cell library is intended to screen for an GOI coding sequence with a maximal expression rate in the cell line used for construction of the cell library.

The invention claimed is:

1. A host cell comprising three or more different types of expression cassettes, each expression cassette coding for the same Protein Of Interest (POI) with identical mature amino acid sequence, and each type of expression cassette at least is comprising a promoter sequence, a polynucleotide sequence of the coding sequence of the POI, a terminator sequence, and optionally a signal sequence, wherein said expression cassettes differ in that they comprise
(A)
 (Aa) different promoter sequences,
 (Ab) different polynucleotide sequences coding for the identical mature amino acid sequence of the POI due to the use of degenerated genetic code,
and optionally
 (Ac) different terminator sequences, and/or
 (Ad) different signal sequences, if present,
or wherein said expression cassettes differ in that they comprise
(B)
 (Ba) the same promoter sequences,
 (Bb) different polynucleotide sequences coding for the identical mature amino acid sequence of the POI due to the use of degenerated genetic code,
and optionally
 (Bc) different terminator sequences, and/or
 (Bd) different signal sequences, if present,
 wherein at least one expression cassette codes for two or more POI with identical mature amino acid sequence, wherein between the coding sequences of said two or more POI is respectively located an internal ribosomal entry site (IRES) sequence.

2. The host cell according to claim 1, wherein in point (Ab) of alternative (A) of claim 1 said different polynucleotide sequences of the coding sequence of the POI are coded by a degenerated genetic code, which degenerated genetic code results in at least 50% of the maximum theoretical polynucleotide sequence difference possible for that particular POI coding polynucleotide sequence, in order to get an identical mature amino acid sequence of said particular POI,
or wherein in point (Bb) of alternative (B) said different polynucleotide sequences of the coding sequence of the POI are coded by a degenerated genetic code, which degenerated genetic code results in at least 50% of the maximum theoretical polynucleotide sequence difference possible for that particular POI coding polynucleotide sequence, in order to get an identical mature amino acid sequence of said particular POI.

3. The host cell according to claim 1, wherein in alternative (A) said promoter, said terminator and/or said signal sequences, if present, and in alternative (B) said terminator and/or said signal sequence, if present, respectively differ between the used different expression cassettes by at least 20%, regarding their nucleotide sequence.

4. The host cell according to claim 1, wherein said POI is heterologous to said host cell.

5. The host cell according to claim 1, wherein said different polynucleotide sequences of the coding sequences of the POI at least have a length of 30 nucleotides.

6. The host cell according to claim 1, wherein said host cell is
 (i) an eukaryotic cell, selected from
  (a) filamentous fungal cells;
  (b) yeast cells;
  (c) mammalian cells;
  (d) human cells;
  (e) insect cells;
  or
 (ii) a prokaryotic cell.

7. A method of generating a host cell as defined in claim 1, comprising the step of transfecting said host cell with at least three different nucleic acid sequences, wherein each nucleic acid sequence comprises at least one different expression cassette coding for the same mature amino acid sequence of said POI.

8. A method of generating a host cell as defined in claim 1, comprising the step of transfecting said host cell with at least one nucleic acid sequence, wherein said nucleic acid sequence comprises at least three different types of expression cassettes, and each of said expression cassettes is coding for the same mature amino acid sequence of said POI.

9. A nucleic acid comprising at least three different types of expression cassettes, each expression cassette coding for the same Protein Of Interest (POI) with identical mature amino acid sequence, and each type of expression cassette at least is comprising a promoter sequence, a polynucleotide sequence of the coding sequence of the POI, a terminator sequence, and optionally a signal sequence, wherein said expression cassettes differ in that they comprise
(A)
 (Aa) different promoter sequences,
 (Ab) different polynucleotide sequences coding for the identical mature amino acid sequence of the POI due to the use of degenerated genetic code,
and optionally
 (Ac) different terminator sequences, and/or
 (Ad) different signal sequences, if present,
or wherein said expression cassettes differ in that they comprise
(B)
 (Ba) the same promoter sequences,
 (Bb) different polynucleotide sequences coding for the identical mature amino acid sequence of the POI due to the use of degenerated genetic code,
and optionally
 (Bc) different terminator sequences, and/or
 (Bd) different signal sequences, if present,
 wherein at least one expression cassette codes for two or more POI with identical mature amino acid sequence, wherein between the coding sequences of said two or more POI is respectively located an internal ribosomal entry site (IBES) sequence.

10. A vector comprising at least three different types of expression cassettes, each expression cassette coding for the same Protein Of Interest (POI) with identical mature amino acid sequence, and each type of expression cassette at least is comprising a promoter sequence, a polynucleotide sequence of the coding sequence of the POI, a terminator sequence, and optionally a signal sequence, wherein said expression cassettes differ in that they comprise (A)
- (Aa) different promoter sequences,
- (Ab) different polynucleotide sequences coding for the identical mature amino acid sequence of the POI due to the use of degenerated genetic code, and optionally
- (Ac) different terminator sequences, and/or
- (Ad) different signal sequences, if present, or wherein said expression cassettes differ in that they comprise (B)
- (Ba) the same promoter sequences,
- (Bb) different polynucleotide sequences coding for the identical mature amino acid sequence of the POI due to the use of degenerated genetic code, and optionally
- (Bc) different terminator sequences, and/or
- (Bd) different signal sequences, if present, wherein at least one expression cassette codes for two or more POI with identical mature amino acid sequence, wherein between the coding sequences of said two or more POI is respectively located an internal ribosomal entry site (IBES) sequence.

11. A kit comprising the nucleic acid as defined in claim 9 and an instruction manual.

12. A process for the manufacture of a POI, comprising
(i) a step of generating a host cell as defined in claim 1, comprising the step of transfecting said host cell
- (A) with at least three different nucleic acid sequences, wherein each nucleic acid sequence comprises at least one different expression cassette coding for the same mature amino acid sequence of said POI, or
- (B) with at least one nucleic acid sequence, wherein said nucleic acid sequence comprises at least three different types of expression cassettes, and each of said expression cassettes is coding for of the same mature amino acid sequence of said POI, and
(ii) a step of obtaining the POI.

13. The process according to claim 12, wherein said POI is a single chain protein or originates from a precursor of a single chain polypeptide.

\* \* \* \* \*

SEQUENCE LISTING

```
<160> NUMBER OF SEQ ID NOS: 10

<210> SEQ ID NO 1
<211> LENGTH: 4355
<212> TYPE: DNA
<213> ORGANISM: Artificial Sequence
<220> FEATURE:
<223> OTHER INFORMATION: synthetic vector sequence

<400> SEQUENCE: 1
cccgtagaaa agatcaaagg atcttcttga gatccttttt ttctgcgcgt aatctgctgc      60
ttgcaaacaa aaaaaccacc gctaccagcg gtggtttgtt tgccggatca agagctacca    120 actcttttc cgaaggtaac tggcttcagc agagcgcaga taccaaatac tgttcttcta    180
gtgtagccgt agttaggcca ccacttcaag aactctgtag caccgcctac atacctcgct    240
ctgctaatcc tgttaccagt ggctgctgcc agtggcgata agtcgtgtct taccgggttg    300
gactcaagac gatagttacc ggataaggcg cagcggtcgg gctgaacggg gggttcgtgc    360
acacagccca gcttggagcg aacgacctac accgaactga gatacctaca gcgtgagcta    420
tgagaaagcg ccacgcttcc cgaagggaga aaggcggaca ggtatccggt aagcggcagg    480
gtcggaacag gagagcgcac gagggagctt ccaggggggaa acgcctggta tctttatagt    540
cctgtcgggt ttcgccacct ctgacttgag cgtcgatttt tgtgatgctc gtcagggggg    600
cggagcctat ggaaaaacgc cagcaacgcg gcctttttac ggttcctggc cttttgctgg    660
ccttttgctc acatgttctt tcctgcggta cccagatcca attcccgctt tgactgcctg    720
aaatctccat cgcctacaat gatgacattt ggatttggtt gactcatgtt ggtattgtga    780
aatagacgca gatcgggaac actgaaaaat acacagttat tattcattta aatcacggtc    840
ttggagtcat caggctctga ctgggcagct gctgcaactg gaacttccca agcctcccac    900
caaacagcag gtgtagccga aagtattcac gtgtcccaga atgaggccca cagtacatct    960
gtcaccgttt ctcaacccccc ttcaacggtt tctttgcaaa ttggagaagc aaatacctg   1020 aaatggtcag ctttctttgg agtagtagtt ccgctgctca acgtactctt cgtttaaaag   1080
ccctcctagg acaaaatggc caagctggga aacgggattt ggtggaactt tattattctt   1140
tctacgatcc aagcattatg ttgtggaaca aagcgaatac tcttattagc tggtaattga   1200
```

```
gcgagttgaa aaaatcaagt ctattggagg gtatggtcag agtactgata gagatccctg    1260
ttaagataat cgatcttttt caaatatcca atttcattcc atcttgccat cgggtcttgg    1320
cttcttacat caataattaa aactacttac tctattagtg ccaaaaatgg taaaccgtat    1380
tcaaattgct gcaagcatat gcttaaaagg atcgcgttgc gagcttcttt tgagattcgc    1440
aagcttgatt ttatgctctt gtgggaagaa aagcaaccca ctgaattcca gatttgttgt    1500
gttttcatgc atggacgaca tactttgagt aataccgtta ctgagatttt accgaattcg    1560
cattgcgttg aggcgtgaag tttcttaatg ctgtgccata tggttaagtt gcgtttcaag    1620
atggtccaca agtattttg tatttaagca gtgtcaattc aagcctaact gctcataaaa    1680
actacacggt ttgctgatat caaaaacgat gtttgagaag agtaaatttg tggtttcgtt    1740
tctgctttta ctccagctat tttgtgtcct tggtgtacat ggagaaattg tcatgaccca    1800
aagtccatca actctttctg cctcagttgg tgatagagtt atcattactt gtcagagttc    1860
tcaatctgtg ttcaacaatt acttgagctg gtaccaacaa aaacctggta gagcccccaa    1920
actgttaatc tacgatgcat ccaaactggc tagcggagta ccttctaggt ttagcggttc    1980
cggatcaggt gcagaattta cactgacaat atcctctttg caaccagacg actttgccac    2040
atactattgc caaggttcgg attatagcgg tggttgggac tccgcgtttg gtcaaggtac    2100
caagttgact gttctcggtg gaggtggagg ttctggtggt ggaggatcag gtggtggcgg    2160
atctggcggt ggagggtccg aggtgcagtt ggtagagtcg ggcggtggat cagtccagcc    2220
tggtggatcc ttgagacttt cctgtaccgc ttctggtatc gacttatcca gttatcccat    2280
gtcgtgggtt agacaagctc cgggaaaggg tttggaatgg gttggtatca tcagcactag    2340
aggaaatact tactacgcta cttgggctaa gggacgtttt acaattagta gagatacgtc    2400
taaaaacact gtgtatttgc agatgaattc actaagagcc gaggacactg caacttacta    2460
ctgtgcacgt ggtctttacg gtaataacta ttatggagct ttcaatttgt ggggacaagg    2520
cacaactgta acggtgtcct cataataagc ggccgcagcg aatttcttat gatttatgat    2580
ttttattatt aaataagtta taaaaaaaat aagtgtatac aaattttaaa gtgactctta    2640
ggttttaaaa cgaaaattct tattcttgag taactctttc ctgtaggtca ggttgctttc    2700
tcaggtatag catgaggtcg ctcttattga ccacacctct accggcatgc cgagcaaatg    2760
cctgcaaatc gctccccatt tcacccaatt gtagatatgc taactccagc aatgagttga    2820
tgaatctcgg tgtgtatttt atgtcctcag aggacaagga tccttcagta atgtcttgtt    2880
tcttttgttg cagtggtgag ccattttgac ttcgtgaaag tttctttaga atagttgttt    2940
ccagaggcca acattccac ccgtagtaaa gtgcaagcgt aggaagacca agactggcat    3000
aaatcaggta taagtgtcga gcactggcag gtgatcttct gaaagtttct actagcagat    3060
aagatccagt agtcatgcat atggcaacaa tgtaccgtgt ggatctaaga acgcgtccta    3120
ctaaccttcg cattcgttgg tccagttttgt tgttatcgat caacgtgaca aggttgtcga    3180
ttccgcgtaa gcatgcatac ccaaggacgc ctgttgcaat tccaagtgag ccagttccaa    3240
caatctttgt aatattagag cacttcattg tgttgcgctt gaaagtaaaa tgcgaacaaa    3300
ttaagagata atctcgaaac cgcgacttca aacgccaata tgatgtgcgg cacacaataa    3360
gcgttcatat ccgctgggtg actttctcgc tttaaaaaat tatccgaaaa aattttctag    3420
agtgttgaca ctttatactt ccggctcgta taatacgaca aggtgtaagg aggactaaac    3480
catggctaaa ctcacctctg ctgttccagt cctgactgct cgtgatgttg ctggtgctgt    3540
```

```
tgagttctgg actgatagac tcggtttctc ccgtgacttc gtagaggacg actttgccgg    3600
tgttgtacgt gacgacgtta ccctgttcat ctccgcagtt caggaccagg ttgtgccaga    3660
caacactctg gcatgggtat gggttcgtgg tctggacgaa ctgtacgctg agtggtctga    3720
ggtcgtgtct accaacttcc gtgatgcatc tggtccagct atgaccgaga tcggtgaaca    3780 gccctgggt cgtgagtttg cactgcgtga tccagctggt aactgcgtgc atttcgtcgc     3840
agaagagcag gactaacctc taggacacct tacgattatt tagagagtat ttattagttt    3900
tattgtatgt atacggatgt tttattatct atttatgccc ttatattctg taactatcca    3960
aaagtcctat cttatcaagc cagcaatcta tgtccgcgaa cgtcaactaa aaataagctt    4020
tttatgctct tctctctttt tttcccttcg gtataattat accttgcatc cacagattct    4080
cctgccaaat tttgcataat cctttacaac atggctatat gggagcactt agcgccctcc    4140
aaaacccata ttgcctacgc atgtataggt gttttttcca caatatttc tctgtgctct     4200 ctttttatta aagagaagct ctatatcgga gaagcttctg tggccgttat attcggcctt    4260
atcgtgggac cacattgcct gaattggttt gccccggaag attggggaaa cttggatctg    4320
attaccttag ctgcaggtac cactgagcgt cagac                               4355

<210> SEQ ID NO 2
<211> LENGTH: 5904
<212> TYPE: DNA
<213> ORGANISM: Artificial Sequence
<220> FEATURE:
<223> OTHER INFORMATION: synthetic vector sequence

<400> SEQUENCE: 2
cccgtagaaa agatcaaagg atcttcttga gatccttttt ttctgcgcgt aatctgctgc      60
ttgcaaacaa aaaaccaccg ctaccagcg gtggtttgtt tgccggatca agagctacca     120 actcttttc cgaaggtaac tggcttcagc agagcgcaga taccaaatac tgttcttcta     180
gtgtagccgt agttaggcca ccacttcaag aactctgtag caccgcctac atacctcgct    240
ctgctaatcc tgttaccagt ggctgctgcc agtggcgata gtcgtgtct taccgggttg     300 gactcaagac gatagttacc ggataaggcg cagcggtcgg gctgaacggg gggttcgtgc    360
acacagccca gcttggagcg aacgacctac accgaactga gatacctaca gcgtgagcta    420
tgagaaagcg ccacgcttcc cgaagggaga aaggcggaca ggtatccggt aagcggcagg    480
gtcggaacag gagagcgcac gagggagctt ccaggggaa acgcctggta tctttatagt     540
cctgtcgggt ttcgccacct ctgacttgag cgtcgatttt tgtgatgctc gtcaggggg    600 cggagcctat ggaaaaacgc cagcaacgcg gccttttac ggttcctggc cttttgctgg    660
ccttttgctc acatgcgat agaatagccg tatgggcttt ttgtagaaat gtcttggtgt    720
cctcgtccaa tcaggtagcc atctctgaaa tatctggctc cgttgcaact ccgaacgacc    780
tgctggcaac gtaaaattct ccggggtaaa acttaaatgt ggagtaatgg aaccagaaac    840
gtctcttccc ttctctctcc ttccaccgcc cgttaccgtc actaggaaat tttactctgc    900
tggagagctt cttctacggc cccttgcag caatgctctt cccagcatta cgttgcgggt     960 aaaacgagg tcgtgtaccc gacctagcag cccaggatg aaaagtccc ggccgtcgct      1020 ggcaataata gcgggcggac gcatgtcatg agattattgg aaaccaccag aatcgaatat    1080
aaaaggcgaa caccttcccc aattttggtt tctcctgacc caaagacttt aaatttaatt    1140
tatttgtccc tatttcaatc aattgaacaa ctatcaaaac acactcgagc aaaacgatgc    1200
gtttcccatc gatttcaca gctgttctgt ttgcagcttc atctgcttta gctgcacctg    1260
```

```
ttaacacaac tacagaggac gaaacggccc agatcccagc tgaggcagtc attggttatt    1320
ccgatttgga aggtgatttc gatgtcgctg tgttaccatt cagtaattcc acaaataacg    1380
gtttgctgtt cattaacacc actatagcaa gcatcgctgc aaaagaggaa ggtgtttccc    1440
tagaaaagag ggagattgtt atgacgcagt cccccagtac tttgtctgct ccgttggag    1500 atagagtaat cataacttgt caatcctctc aatctgtctt taacaattac ctttcttggt    1560
accaacagaa accaggcagg gctccaaagt tgctaatcta tgatgcatct aaactggcct    1620
ccggtgttcc atcacgtttt tcaggttcag gatccggtgc tgagttcact ttaacgattt    1680
cctcgttgca accggatgac tttgccacat attactgtca aggttctgac tactcaggtg    1740
gttgggactc tgctttcggt caaggtacca aactgactgt attgggagga ggtggaggta    1800
gcggcggtgg aggttcagga ggtggtggat ccggaggggg tggaagtgaa gttcaattgg    1860
tggaaagcgg tggtggttcc gttcagcctg gaggtagctt gcgtctgtcg tgcactgcaa    1920
gtggtattga cttaagctca tatcctatgt cttgggtcag acaagcacct ggtaagggtt    1980
tggagtgggt cggcatcatt agcactagag gtaacacata ctatgctaca tgggcaaagg    2040
gaagattcac aatctcacgt gatacatcta aaaatacagt ttatcttcag atgaatagtc    2100
tcagagctga agatacagct acctactact gtgccagagg attatacggt aataactatt    2160
atggtgcatt caatctatgg ggccaaggta ctactgtgac cgtgtcctcg taatagaggc    2220
cttgttcttt cctgcggtac ccagatccaa ttcccgcttt gactgcctga aatctccatc    2280
gcctacaatg atgacatttg gatttggttg actcatgttg gtattgtgaa atagacgcag    2340
atcgggaaca ctgaaaaata cacagttatt attcatttaa atcacggtct ggagtcatc    2400 aggctctgac tggcagctg ctgcaactgg aacttcccaa gcctcccacc aaacagcagg    2460
tgtagccgaa agtattcacg tgtcccagaa tgaggcccac agtacatctg tcaccgtttc    2520
tcaaccccct tcaacggttt ctttgcaaat tggagaagca aatacccctga aatggtcagc    2580 tttctttgga gtagtagttc cgctgctcaa cgtactcttc gtttaaaagc cctcctagga    2640
caaaatggcc aagctgggaa acgggatttg gtggaacttt attattcttt ctacgatcca    2700
agcattatgt tgtggaacaa agcgaatact cttattagct ggtaattgag cgagttgaaa    2760
aaatcaagtc tattggaggg tatggtcaga gtactgatag agatcccctgt taagataatc    2820 gatctttttc aaatatccaa tttcattcca tcttgccatc gggtcttggc ttcttacatc    2880
aataattaaa actacttact ctattagtgc caaaaatggt aaaccgtatt caaattgctg    2940
caagcatatg cttaaaagga tcgcgttgcg agcttctttt gagattcgca agcttgattt    3000
tatgctcttg tgggaagaaa agcaacccac tgaattccag atttgttgtg ttttcatgca    3060
tggacgacat actttgagta ataccgttac tgagatttta ccgaattcgc attgcgttga    3120
ggcgtgaagt ttcttaatgc tgtgccatat ggttaagttg cgtttcaaga tggtccacaa    3180 gtattttgt atttaagcag tgtcaattca agcctaactg ctcataaaaa ctacacggtt    3240
tgctgatatc aaaaacgatg tttgagaaga gtaaatttgt ggtttcgttt ctgcttttac    3300
tccagctatt ttgtgtccctt ggtgtacatg gagaaattgt catgacccaa agtccatcaa    3360
ctctttctgc ctcagttggt gatagagtta tcattacttg tcagagttct caatctgtgt    3420
tcaacaatta cttgagctgg taccaacaaa aacctggtag agcccccaaa ctgttaatct    3480
acgatgcatc caaactggct agcggagtac cttctaggtt tagcggttcc ggatcaggtg    3540
cagaatttac actgacaata tcctctttgc aaccagacga ctttgccaca tactattgcc    3600
```

```
aaggttcgga ttatagcggt ggttgggact ccgcgtttgg tcaaggtacc aagttgactg    3660
ttctcggtgg aggtggaggt tctggtggtg gaggatcagg tggtggcgga tctggcggtg    3720
gagggtccga ggtgcagttg gtagagtcgg gcggtggatc agtccagcct ggtggatcct    3780
tgagactttc ctgtaccgct tctgtatcg acttatccag ttatcccatg tcgtgggtta    3840
gacaagctcc gggaaagggt ttggaatggg ttggtatcat cagcactaga ggaaatactt    3900
actacgctac ttgggctaag ggacgtttta caattagtag agatacgtct aaaaacactg    3960
tgtatttgca gatgaattca ctaagagccg aggacactgc aacttactac tgtgcacgtg    4020
gtctttacgg taataactat tatggagctt tcaatttgtg gggacaaggc acaactgtaa    4080
cggtgtcctc ataataagcg gccgcagcga atttcttatg atttatgatt tttattatta    4140
aataagttat aaaaaaaata agtgtataca aattttaaag tgactcttag gttttaaaac    4200
gaaaattctt attcttgagt aactctttcc tgtaggtcag gttgctttct caggtatagc    4260
atgaggtcgc tcttattgac cacacctcta ccggcatgcc gagcaaatgc ctgcaaatcg    4320
ctccccattt cacccaattg tagatatgct aactccagca atgagttgat gaatctcggt    4380
gtgtatttta tgtcctcaga ggacaaggat ccttcagtaa tgtcttgttt cttttgttgc    4440
agtggtgagc cattttgact tcgtgaaagt ttctttagaa tagttgtttc cagaggccaa    4500
acattccacc cgtagtaaag tgcaagcgta ggaagaccaa gactggcata aatcaggtat    4560
aagtgtcgag cactggcagg tgatcttctg aaagtttcta ctagcagata agatccagta    4620
gtcatgcata tggcaacaat gtaccgtgtg gatctaagaa cgcgtcctac taaccttcgc    4680
attcgttggt ccagtttgtt gttatcgatc aacgtgacaa ggttgtcgat ccgcgtaag    4740
catgcatacc caaggacgcc tgttgcaatt ccaagtgagc cagttccaac aatctttgta    4800
atattagagc acttcattgt gttgcgcttg aaagtaaaat gcgaacaaat taagagataa    4860
tctcgaaacc gcgacttcaa acgccaatat gatgtgcggc acacaataag cgttcatatc    4920
cgctgggtga ctttctcgct ttaaaaaatt atccgaaaaa attttctaga gtgttgacac    4980
tttatacttc cggctcgtat aatacgacaa ggtgtaagga ggactaaacc atggctaaac    5040
tcacctctgc tgttccagtc ctgactgctc gtgatgttgc tggtgctgtt gagttctgga    5100
ctgatagact cggtttctcc cgtgacttcg tagaggacga ctttgccggt gttgtacgtg    5160
acgacgttac cctgttcatc tccgcagttc aggaccaggt tgtgccagac aacactctgg    5220
catgggtatg ggttcgtggt ctggacgaac tgtacgctga gtggtctgag gtcgtgtcta    5280
ccaacttccg tgatgcatct ggtccagcta tgaccgagat cggtgaacag ccctggggtc    5340
gtgagtttgc actgcgtgat ccagctggta actgcgtgca tttcgtcgca gaagagcagg    5400
actaacctct aggacacctt acgattattt agagagtatt tattagtttt attgtatgta    5460
tacggatgtt ttattatcta tttatgccct tatattctgt aactatccaa aagtcctatc    5520
ttatcaagcc agcaatctat gtccgcgaac gtcaactaaa aataagcttt ttatgctctt    5580
ctctcttttt ttcccttcgg tataattata ccttgcatcc acagattctc ctgccaaatt    5640
ttgcataatc ctttacaaca tggctatatg ggagcactta gcgccctcca aaacccatat    5700
tgcctacgca tgtataggtg ttttttccac aatatttct ctgtgctctc tttttattaa    5760
agagaagctc tatatcggag aagcttctgt ggccgttata ttcggcctta tcgtgggacc    5820
acattgcctg aattggtttg ccccggaaga ttggggaaac ttggatctga ttaccttagc    5880
tgcaggtacc actgagcgtc agac                                            5904
```

```
<210> SEQ ID NO 3
<211> LENGTH: 7866
<212> TYPE: DNA
<213> ORGANISM: Artificial Sequence
<220> FEATURE:
<223> OTHER INFORMATION: synthetic vector sequence

<400> SEQUENCE: 3
```

| | | | | | |
|---|---|---|---|---|---|
| cgatttatta | tgttacaata | tggaagggaa | ctttacactt | ctcctatgca | catatattaa | 60 |
| ttaaagtcca | atgctagtag | agaagggggg | taacacccct | ccgcgctctt | ttccgatttt | 120 |
| tttctaaacc | gtggaatatt | tcgcatatcc | ttttgttgtt | tccgggtgta | caatatggac | 180 |
| ttcctctttt | ctggcaacca | aacccataca | tcgggattcc | tataataccct | tcgttggtct | 240 |
| ccctaacatg | taggtggcgg | aggggagata | tacaatagaa | cagataccag | acaagacata | 300 |
| atgggctaaa | caagactaca | ccaattacac | tgcctcattg | atggtggtac | ataacgaact | 360 |
| aatactgtag | ccctagactt | gatagccatc | atcatatcga | agtttcacta | cccttttttcc | 420 |
| atttgccatc | tattgaagta | ataataggcg | catgcaactt | cttttctttt | tttttctttt | 480 |
| ctctctcccc | cgttgttgtc | tcaccatatc | cgcaatgaca | aaaaaatgat | ggaagacact | 540 |
| aaaggaaaaa | attaacgaca | aagacagcac | caacagatgt | cgttgttcca | gagctgatga | 600 |
| ggggtatctc | gaagcacacg | aaactttttc | cttccttcat | tcacgcacac | tactctctaa | 660 |
| tgagcaacgg | tataccggcct | tccttccagt | tacttgaatt | tgaaataaaa | aaagtttgc | 720 |
| tgtcttgcta | tcaagtataa | atagacctgc | aattattaat | cttttgtttc | ctcgtcattg | 780 |
| ttctcgttcc | ctttcttcct | tgtttctttt | tctgcacaat | atttcaagct | ataccaagca | 840 |
| tacaatcaac | tatctcatat | acagtcgacc | aaaacgatga | agtgggtcac | tttcatctcg | 900 |
| ctgctatttt | tgttctccag | cgcctatagc | gagattgtga | tgactcaatc | cccttccact | 960 |
| ctaagcgctt | ctgtcggtga | ccgtgttatc | attacctgtc | aatcctctca | atcggttttc | 1020 |
| aacaattact | tatcctggta | tcaacagaag | ccaggtcgtg | cacctaaact | tctgatttac | 1080 |
| gatgcttcaa | aattggctag | tggtgtccca | agcagatttt | cgggatctgg | ttccggtgcc | 1140 |
| gagtttacac | tcacgatctc | ctcacttcaa | cccgatgatt | tcgcaacata | ctattgtcaa | 1200 |
| ggtagcgact | atagtggagg | ttgggactct | gcctttggac | aagtactaa | gctaacagtt | 1260 |
| ttgggtggag | gcggaggttc | gggtggtggt | ggatcaggag | gaggtggtag | tggcggagga | 1320 |
| ggctcagaag | tgcaactggt | tgaaagtggt | ggaggttccg | ttcagccagg | gggttccttg | 1380 |
| agattgtctt | gcactgcttc | tggtatcgac | ctgtcatcat | acccaatgag | ctgggtaaga | 1440 |
| caggctcctg | gtaaaggttt | ggaatgggtt | ggaattatct | ctactcgtgg | taatacatat | 1500 |
| tacgcaacat | gggctaaggg | tagattcaca | atatccaggg | atacttccaa | aaacacagta | 1560 |
| tacttacaaa | tgaattcttt | gagagccgag | gataccgcta | cctattactg | tgcaaggggt | 1620 |
| ctgtatggta | acaattacta | tggagcattc | aatttgtggg | gtcagggcac | gactgtgact | 1680 |
| gtcagctcat | aatagagatc | tccttttcct | ttgtccatat | catgtaatta | gttatgtcac | 1740 |
| gcttacattc | acgccctccc | cccacatccg | ctctaaccga | aaaggaagga | gttagacaac | 1800 |
| ctgaagtcta | ggtccctatt | tatttttttta | tagttatgtt | agtattaaga | acgttattta | 1860 |
| tatttcaaat | ttttctttttt | tttctgtaca | dacgcgtgta | cgcatgtaac | attatactga | 1920 |
| aaaccttgct | tgagaaggtt | ttgggacgct | cgaaggcttt | aatttgcaag | ctgccgtatg | 1980 |
| ggcttttttgt | agaaatgtct | tggtgtcctc | gtccaatcag | gtagccatct | ctgaaatatc | 2040 |
| tggctccgtt | gcaactccga | acgacctgct | ggcaacgtaa | aattctccgg | ggtaaaactt | 2100 |

```
aaatgtggag taatggaacc agaaacgtct cttcccttct ctctccttcc accgccgtt     2160
accgtcacta ggaaatttta ctctgctgga gagcttcttc tacggccccc ttgcagcaat    2220
gctcttccca gcattacgtt gcgggtaaaa cggaggtcgt gtacccgacc tagcagccca    2280
gggatggaaa agtcccggcc gtcgctggca ataatagcgg gcggacgcat gtcatgagat    2340
tattggaaac caccagaatc gaatataaaa ggcgaacacc tttcccaatt ttggtttctc    2400
ctgacccaaa gactttaaat ttaatttatt tgtccctatt tcaatcaatt gaacaactat    2460
caaaacacac tcgagcaaaa cgatgcgttt cccatcgatt ttcacagctg ttctgtttgc    2520
agcttcatct gctttagctg cacctgttaa cacaactaca gaggacgaaa cggcccagat    2580
cccagctgag gcagtcattg gttattccga tttggaaggt gatttcgatg tcgctgtgtt    2640
accattcagt aattccacaa ataacggttt gctgttcatt aacaccacta tagcaagcat    2700
cgctgcaaaa gaggaaggtg tttccctaga aaagagggag attgttatga cgcagtcccc    2760
cagtactttg tctgcttccg ttggagatag agtaatcata acttgtcaat cctctcaatc    2820
tgtctttaac aattaccttt cttggtacca acagaaacca ggcagggctc caaagttgct    2880
aatctatgat gcatctaaac tggcctccgg tgttccatca cgttttttcag gttcaggatc    2940
cggtgctgag ttcactttaa cgatttcctc gttgcaaccg gatgactttg ccacatatta    3000
ctgtcaaggt tctgactact caggtggttg ggactctgct ttcggtcaag gtaccaaact    3060
gactgtattg ggaggaggtg gaggtagcgg cggtggaggt tcaggaggtg gtggatccgg    3120
aggggggtgga agtgaagttc aattggtgga aagcggtggt ggttccgttc agcctggagg    3180
tagcttgcgt ctgtcgtgca ctgcaagtgg tattgactta agctcatatc ctatgtcttg    3240
ggtcagacaa gcacctggta agggtttgga gtgggtcggc atcattagca ctagaggtaa    3300
cacatactat gctacatggg caaagggaag attcacaatc tcacgtgata catctaaaaa    3360
tacagtttat cttcagatga atagtctcag agctgaagat acagctacct actactgtgc    3420
cagaggatta tacggtaata actattatgg tgcattcaat ctatgggggcc aaggtactac    3480
tgtgaccgtg tcctcgtaat agaggccttg ttctttcctg cggtacccag atccaattcc    3540
cgctttgact gcctgaaatc tccatcgcct acaatgatga catttggatt tggttgactc    3600
atgttggtat tgtgaaatag acgcagatcg ggaacactga aaaatacaca gttattattc    3660
atttaaatca cggtcttgga gtcatcaggc tctgactggg cagctgctgc aactggaact    3720
tcccaagcct cccaccaaac agcaggtgta gccgaaagta ttcacgtgtc ccagaatgag    3780
gcccacagta catctgtcac cgtttctcaa ccccccttcaa cggtttcttt gcaaattgga    3840
gaagcaaata ccctgaaatg gtcagctttc tttggagtag tagttccgct gctcaacgta    3900
ctcttcgttt aaaagccctc ctaggacaaa atggccaagc tgggaaacgg gatttggtgg    3960
aactttatta ttcttctac gatccaagca ttatgttgtg gaacaaagcg aatactctta    4020
ttagctggta attgagcgag ttgaaaaaat caagtctatt ggagggtatg gtcagagtac    4080
tgatagagat ccctgttaag ataatcgatc ttttcaaat atccaatttc attccatctt    4140
gccatcgggt cttggcttct tacatcaata attaaaacta cttactctat tagtgccaaa    4200
aatggtaaac cgtattcaaa ttgctgcaag catatgctta aaaggatcgc gttgcgagct    4260
tcttttgaga ttcgcaagct tgattttatg ctcttgtggg aagaaaagca acccactgaa    4320
ttccagattt gttgtgtttt catgcatgga cgacatactt tgagtaatac cgttactgag    4380
atttttaccga attcgcattg cgttgaggcg tgaagtttct taatgctgtg ccatatggtt    4440
aagttgcgtt tcaagatggt ccacaagtat ttttgtattt aagcagtgtc aattcaagcc    4500
```

```
taactgctca taaaaactac acggtttgct gatatcaaaa acgatgtttg agaagagtaa    4560
atttgtggtt tcgtttctgc ttttactcca gctattttgt gtccttggtg tacatggaga    4620
aattgtcatg acccaaagtc catcaactct ttctgcctca gttggtgata gagttatcat    4680
tacttgtcag agttctcaat ctgtgttcaa caattacttg agctggtacc aacaaaaacc    4740
tggtagagcc cccaaactgt taatctacga tgcatccaaa ctggctagcg agtaccttc     4800 taggtttagc ggttccggat caggtgcaga atttacactg acaatatcct ctttgcaacc    4860
agacgacttt gccacatact attgccaagg ttcggattat agcggtggtt gggactccgc    4920
gtttggtcaa ggtaccaagt tgactgttct cggtggaggt ggaggttctg gtggtggagg    4980
atcaggtggt ggcggatctg cggtggagg tccgaggtg cagttggtag agtcgggcgg     5040
tggatcagtc cagcctggtg gatccttgag actttcctgt accgcttctg gtatcgactt    5100
atccagttat cccatgtcgt gggttagaca agctccggga aagggtttgg aatgggttgg    5160
tatcatcagc actagaggaa atacttacta cgctacttgg gctaagggac gttttacaat    5220
tagtagagat acgtctaaaa acactgtgta tttgcagatg aattcactaa gagccgagga    5280
cactgcaact tactactgtg cacgtggtct ttacggtaat aactattatg gagctttcaa    5340
tttgtgggga caaggcacaa ctgtaacggt gtcctcataa taagcggccg cagcgaattt    5400
cttatgattt atgattttta ttattaaata agttataaaa aaaataagtg tatacaaatt    5460
ttaaagtgac tcttaggttt taaaacgaaa attcttattc ttgagtaact ctttcctgta    5520
ggtcaggttg ctttctcagg tatagcatga ggtcgctctt attgaccaca cctctaccgg    5580
catgccgagc aaatgcctgc aaatcgctcc ccatttcacc caattgtaga tatgctaact    5640
ccagcaatga gttgatgaat ctcggtgtgt attttatgtc ctcagaggac aaggatcctt    5700
cagtaatgtc ttgtttcttt tgttgcagtg gtgagccatt ttgacttcgt gaaagtttct    5760
ttagaatagt tgtttccaga ggccaaacat tccacccgta gtaaagtgca agcgtaggaa    5820
gaccaagact ggcataaatc aggtataagt gtcgagcact ggcaggtgat cttctgaaag    5880
tttctactag cagataagat ccagtagtca tgcatatggc aacaatgtac cgtgtggatc    5940
taagaacgcg tcctactaac cttcgcattc gttggtccag tttgttgtta tcgatcaacg    6000
tgacaaggtt gtcgattccg cgtaagcatg catacccaag gacgcctgtt gcaattccaa    6060
gtgagccagt tccaacaatc tttgtaatat tagagcactt cattgtgttg cgcttgaaag    6120
taaaatgcga acaaattaag agataatctc gaaaccgcga cttcaaacgc caatatgatg    6180
tgcggcacac aataagcgtt catatccgct gggtgacttt ctcgctttaa aaaattatcc    6240
gaaaaatttt tctagagtgt tgacacttta tacttccggc tcgtataata cgacaaggtg    6300
taaggaggac taaaccatgg ctaaactcac ctctgctgtt ccagtcctga ctgctcgtga    6360
tgttgctggt gctgttgagt tctggactga tagactcggt ttctcccgtg acttcgtaga    6420
ggacgacttt gccggtgttg tacgtgacga cgttacccctg ttcatctccg cagttcagga    6480
ccaggttgtg ccagacaaca ctctggcatg ggtatgggtt cgtggtctgg acgaactgta    6540
cgctgagtgg tctgaggtcg tgtctaccaa cttccgtgat gcatctggtc cagctatgac    6600
cgagatcggt gaacagccct ggggtcgtga gtttgcactg cgtgatccag ctggtaactg    6660
cgtgcatttc gtcgcagaag agcaggacta acctctagga caccttacga ttatttagag    6720
agtatttatt agttttattg tatgtatacg gatgttttat tatctatttat tgcccttata    6780 ttctgtaact atccaaaagt cctatcttat caagccagca atctatgtcc gcgaacgtca    6840
```

```
actaaaaata agcttttat gctcttctct cttttttcc cttcggtata attatacctt    6900
gcatccacag attctcctgc caaattttgc ataatccttt acaacatggc tatatgggag    6960
cacttagcgc cctccaaaac ccatattgcc tacgcatgta taggtgtttt ttccacaata    7020
ttttctctgt gctctctttt tattaaagag aagctctata tcggagaagc ttctgtggcc    7080
gttatattcg gccttatcgt gggaccacat tgcctgaatt ggtttgcccc ggaagattgg    7140
ggaaacttgg atctgattac cttagctgca ggtaccactg agcgtcagac cccgtagaaa    7200
agatcaaagg atcttcttga tccttttttt ttctgcgcgt aatctgctgc ttgcaaacaa    7260
aaaaaccacc gctaccagcg gtggtttgtt tgccggatca agagctacca actctttttc    7320
cgaaggtaac tggcttcagc agagcgcaga taccaaatac tgttcttcta gtgtagccgt    7380
agttaggcca ccacttcaag aactctgtag caccgcctac atacctcgct ctgctaatcc    7440
tgttaccagt ggctgctgcc agtggcgata agtcgtgtct taccgggttg gactcaagac    7500
gatagttacc ggataaggcg cagcggtcgg gctgaacggg gggttcgtgc acacagccca    7560
gcttggagcg aacgacctac accgaactga gatacctaca gcgtgagcta tgagaaagcg    7620
ccacgcttcc cgaagggaga aaggcggaca ggtatccggt aagcggcagg gtcggaacag    7680
gagagcgcac gagggagctt ccagggggaa acgcctggta tctttatagt cctgtcgggt    7740
ttcgccacct ctgacttgag cgtcgatttt tgtgatgctc gtcaggggg cggagcctat    7800
ggaaaaacgc cagcaacgcg gccttttac ggttcctggc cttttgctgg ccttttgctc    7860
acatcg                                                              7866
```

<210> SEQ ID NO 4
<211> LENGTH: 9667
<212> TYPE: DNA
<213> ORGANISM: Artificial Sequence
<220> FEATURE:
<223> OTHER INFORMATION: synthetic vector sequence

<400> SEQUENCE: 4

```
cgatttatta tgttacaata tggaagggaa ctttacactt ctcctatgca catatattaa      60
ttaaagtcca atgctagtag agaaggggg taacacccct ccgcgctctt ttccgatttt     120
tttctaaacc gtggaatatt tcgcatatcc ttttgttgtt tccgggtgta caatatggac     180
ttcctctttt ctggcaacca aacccataca tcgggattcc tataataccct tcgttggtct    240
ccctaacatg taggtggcgg aggggagata tacaatagaa cagataccag acaagacata     300
atgggctaaa caagactaca ccaattacac tgcctcattg atggtggtac ataacgaact     360
aatactgtag ccctagactt gatagccatc atcatatcga agtttcacta ccctttttcc     420
atttgccatc tattgaagta ataataggcg catgcaactt ctttctttt ttttctttt       480
ctctctcccc cgttgttgtc tcaccatatc cgcaatgaca aaaaaatgat ggaagacact     540
aaaggaaaaa attaacgaca aagacagcac caacagatgt cgttgttcca gagctgatga     600
ggggtatctc gaagcacacg aaacttttc cttccttcat tcacgcacac tactctctaa      660
tgagcaacgg tatacggcct tccttccagt tacttgaatt tgaaataaaa aaagtttgc      720
tgtcttgcta tcaagtataa atagaccctgc aattattaat cttttgtttc ctcgtcattg    780
ttctcgttcc ctttcttcct tgtttctttt tctgcacaat atttcaagct ataccaagca    840
tacaatcaac tatctcatat acagtcgacc aaaacgatga agtgggtcac tttcatctcg    900
ctgctatttt tgttctccag cgcctatagc gagattgtga tgactcaatc cccttccact    960
ctaagcgctt ctgtcggtga ccgtgttatc attacctgtc aatcctctca atcggttttc   1020
```

```
aacaattact tatcctggta tcaacagaag ccaggtcgtg cacctaaact tctgatttac    1080
gatgcttcaa aattggctag tggtgtccca agcagatttt cgggatctgg ttccggtgcc    1140
gagtttacac tcacgatctc ctcacttcaa cccgatgatt tcgcaacata ctattgtcaa    1200
ggtagcgact atagtggagg ttgggactct gcctttggac aaggtactaa gctaacagtt    1260
ttgggtggag gcggaggttc gggtggtggt ggatcaggag gaggtggtag tggcggagga    1320
ggctcagaag tgcaactggt tgaaagtggt ggaggttccg ttcagccagg gggttccttg    1380
agattgtctt gcactgcttc tggtatcgac ctgtcatcat acccaatgag ctgggtaaga    1440
caggctcctg gtaaaggttt ggaatggggtt ggaattatct ctactcgtgg taatacatat    1500
tacgcaacat gggctaaggg tagattcaca atatccaggg atacttccaa aaacacagta    1560
tacttacaaa tgaattcttt gagagccgag ataccgcta cctattactg tgcaaggggt    1620
ctgtatggta acaattacta tggagcattc aatttgtggg gtcagggcac gactgtgact    1680
gtcagctcat aatagagatc tccttttcct ttgtccatat catgtaatta gttatgtcac    1740
gcttacattc acgccctccc cccacatccg ctctaaccga aaaggaagga gttagacaac    1800
ctgaagtcta ggtccctatt tatttttta tagttatgtt agtattaaga acgttattta    1860
tatttcaaat ttttcttttt tttctgtaca gacgcgtgta cgcatgtaac attatactga    1920
aaaccttgct tgagaaggtt ttgggacgct cgaaggcttt aatttgcaag ctgccgtatg    1980 ggcttttgt agaaatgtct tggtgtcctc gtccaatcag gtagccatct ctgaaatatc    2040
tggctccgtt gcaactccga acgacctgct ggcaacgtaa aattctccgg ggtaaaactt    2100
aaatgtggag taatggaacc agaaacgtct cttcccttct ctctccttcc accgccgtt    2160 accgtcacta ggaaattta ctctgctgga gagcttcttc tacggcccc ttgcagcaat    2220 gctcttccca gcattacgtt gcgggtaaaa cggaggtcgt gtacccgacc tagcagccca    2280
gggatggaaa agtcccggcc gtcgctggca ataatagcgg gcggacgcat gtcatgagat    2340
tattggaaac caccagaatc gaatataaaa ggcgaacacc tttcccaatt ttggtttctc    2400
ctgacccaaa gactttaaat ttaatttatt tgtccctatt tcaatcaatt gaacaactat    2460
caaaacacac tcgagcaaaa cgatgcgttt cccatcgatt ttcacagctg ttctgtttgc    2520
agcttcatct gctttagctg cacctgttaa cacaactaca gaggacgaaa cggcccagat    2580
cccagctgag gcagtcattg gttattccga tttggaaggt gatttcgatg tcgctgtgtt    2640
accattcagt aattccacaa ataacggttt gctgttcatt aacaccacta tagcaagcat    2700
cgctgcaaaa gaggaaggtg tttccctaga aaagagggag attgttatga cgcagtcccc    2760
cagtactttg tctgcttccg ttggagatag agtaatcata acttgtcaat cctctcaatc    2820
tgtctttaac aattaccttt cttggtacca acagaaacca ggcagggctc caaagttgct    2880
aatctatgat gcatctaaac tggcctccgg tgttccatca cgttttcag gttcaggatc    2940 cggtgctgag ttcactttaa cgatttcctc gttgcaaccg gatgactttg ccacatatta    3000
ctgtcaaggt tctgactact caggtggttg ggactctgct ttcggtcaag gtaccaaact    3060
gactgtattg ggaggaggtg gaggtagcgg cggtggaggt tcaggaggtg gtggatccgg    3120
agggggtgga agtgaagttc aattggtgga aagcggtggg ggttccgttc agcctggagg    3180
tagcttgcgt ctgtcgtgca ctgcaagtgg tattgactta agctcatatc ctatgtcttg    3240
ggtcagacaa gcacctggta agggttttgga gtgggtcggc atcattagca ctagaggtaa    3300
cacatactat gctacatggg caaagggaag attcacaatc tcacgtgata catctaaaaa    3360
```

```
tacagtttat cttcagatga atagtctcag agctgaagat acagctacct actactgtgc    3420
cagaggatta tacggtaata actattatgg tgcattcaat ctatggggcc aaggtactac    3480
tgtgaccgtg tcctcgtaat agaggccttg ttctttcctg cggtacccag atccaattcc    3540
cgctttgact gcctgaaatc tccatcgcct acaatgatga catttggatt tggttgactc    3600
atgttggtat tgtgaaatag acgcagatcg ggaacactga aaaatacaca gttattattc    3660
atttaaatca cggtcttgga gtcatcaggc tctgactggg cagctgctgc aactggaact    3720
tcccaagcct cccaccaaac agcaggtgta gccgaaagta ttcacgtgtc ccagaatgag    3780
gcccacagta catctgtcac cgtttctcaa ccccccttcaa cggtttcttt gcaaattgga    3840
gaagcaaata ccctgaaatg gtcagctttc tttggagtag tagttccgct gctcaacgta    3900
ctcttcgttt aaaagccctc ctaggacaaa atggccaagc tgggaaacgg gatttggtgg    3960
aactttatta ttctttctac gatccaagca ttatgttgtg aacaaagcg aatactctta    4020
ttagctggta attgagcgag ttgaaaaaat caagtctatt ggagggtatg gtcagagtac    4080
tgatagagat ccctgttaag ataatcgatc ttttttcaaat atccaatttc attccatctt    4140
gccatcgggt cttggcttct tacatcaata attaaaacta cttactctat tagtgccaaa    4200
aatggtaaac cgtattcaaa ttgctgcaag catatgctta aaaggatcgc gttgcgagct    4260
tcttttgaga ttcgcaagct tgattttatg ctcttgtggg aagaaaagca acccactgaa    4320
ttccagattt gttgtgtttt catgcatgga cgacatactt tgagtaatac cgttactgag    4380
attttaccga attcgcattg cgttgaggcg tgaagtttct taatgctgtg ccatatggtt    4440
aagttgcgtt tcaagatggt ccacaagtat ttttgtattt aagcagtgtc aattcaagcc    4500
taactgctca taaaaactac acggtttgct gatatcaaaa acgatgtttg agaagagtaa    4560
atttgtggtt tcgtttctgc ttttactcca gctattttgt gtccttggtg tacatggaga    4620
aattgtcatg acccaaagtc catcaactct ttctgcctca gttggtgata gagttatcat    4680
tacttgtcag agttctcaat ctgtgttcaa caattacttg agctggtacc aacaaaaacc    4740
tggtagagcc cccaaactgt taatctacga tgcatccaaa ctggctagcg gagtaccttc    4800
taggtttagc ggttccggat caggtgcaga atttacactg acaatatcct ctttgcaacc    4860
agacgacttt gccacatact attgccaagg ttcggattat agcggtggtt gggactccgc    4920
gtttggtcaa gtaccaagt tgactgttct cggtggaggt ggaggttctg gtggtggagg    4980
atcaggtggt ggcggatctg gcggtggagg gtccgaggtg cagttggtag agtcgggcgg    5040
tggatcagtc cagcctggtg gatccttgag acttttcctgt accgcttctg gtatcgactt    5100
atccagttat cccatgtcgt gggttagaca agctccggga aagggtttgg aatgggttgg    5160
tatcatcagc actagaggaa atacttacta cgctacttgg gctaagggac gttttacaat    5220
tagtagagat acgtctaaaa acactgtgta tttgcagatg aattcactaa gagccgagga    5280
cactgcaact tactactgtg cacgtggtct ttacggtaat aactattatg gagctttcaa    5340
tttgtgggga caaggcacaa ctgtaacggt gtcctcataa taagcggccg cagcgaattt    5400
cttatgattt atgatttta ttattaaata agttataaaa aaaataagtg tatacaaatt    5460
ttaaagtgac tcttaggttt taaaacgaaa attcttattc ttgagtaact cttttcctgta    5520
ggtcaggttg ctttctcagg tatagcatga ggtcgctctt attgaccaca cctctaccgg    5580
catgccgagc aaatgcctgc aaatcgctcc ccatttcacc caattgtaga tatgctaact    5640
ccagcaatga gttgatgaat ctcggtgtgt attttatgtc ctcagaggac aaggatccct    5700
tgccaacagg gagttcttca gagacatgga ggctcaaaac gaaattattg acagcctaga    5760
```

```
catcaatagt catacaacag aaagcgacca cccaactttg gctgataata gcgtataaac    5820
aatgcatact ttgtacgttc aaaatacaat gcagtagata tatttatgca tattacatat    5880
aatacatatc acataggaag caacaggcgc gttggacttt taattttcga ggaccgcgaa    5940
tccttacatc acacccaatc ccccacaagt gatcccccac acaccatagc ttcaaaatgt    6000
ttctactcct tttttactct tccagatttt ctcggactcc gcgcatcgcc gtaccacttc    6060
aaaacaccca agcacagcat actaaatttc ccctctttct tcctctaggg tgtcgttaat    6120
tacccgtact aaaggtttgg aaaagaaaaa agagaccgcc tcgtttcttt ttcttcgtcg    6180
aaaaaggcaa taaaaatttt tatcacgttt cttttttcttg aaaattttttt tttttgattt   6240 ttttctcttt cgatgacctc ccattgatat ttaagttaat aaacggtctt caatttctca    6300
agtttcagtt tcattttctt tgttctatta caacttttttt tacttcttgc tcattagaaa    6360
gaaagcatag caatctaatc taagttttaa ttacaaaact agtcaaaacg atgagatttc    6420
cttcaatttt tactgctgtt ttattcgcag catcctccgc attagctgaa attgtcatga    6480
cccaaagccc atccactctg tctgcttccg ttggtgaccg tgttatcata acatgtcagt    6540
caagccaatc ggttttcaat aactatctat catggtatca acaaaaacct ggacgtgcac    6600
caaagttact tatctacgat gctagtaaac tggcaagtgg agtaccttcg agattcagcg    6660
gctccggttc tggtgctgaa ttcacattga cgatttccag tctacaacca gatgactttg    6720
ctacttacta ctgccaaggt tcagactatt ccggaggatg ggactccgca tttggtcagg    6780
gaacaaaatt gactgtgtta ggtgggggcg gaggtagcgg tggaggtggt tcggaggtg    6840 gcggttccgg tggtggtggt tccgaagtgc agttggttga gtctggtgga ggttctgtcc    6900
aacccggagg atcccttaga ttgtcatgta cagcctctgg tattgatttg tctagttacc    6960
caatgtcatg ggttaggcag gcccctggta agggactgga gtgggtaggt attatctcaa    7020
ctagaggcaa tacttattac gcaacgtggg caaagggtag atttaccatc tctagggata    7080
cctccaaaaa cacagtctat ctgcaaatga atagcttgag agctgaggat actgctacat    7140
attactgtgc ccgtggattg tatggtaaca attactacgg tgctttcaat ctctggggtc    7200
aaggtacaac tgtgactgtt tcatcttaat aggagctctc aagaggatgt cagaatgcca    7260
tttgcctgag agatgcaggc ttcatttttg atacttttttt atttgtaacc tatatagtat    7320 aggattttttt ttgtcatttt gtttcttctc gtacgagctt gctcctgatc agcctatctc    7380
gcagcagatg aatatcttgt ggtagggggtt tgggaaaatc attcgagttt gatgttttttc   7440 ttggtatttc ccactcctct tcagagtaca gaagattaag tgagaccttc gtttgtgcct    7500
tcagtaatgt cttgtttctt ttgttgcagt ggtgagccat tttgacttcg tgaaagtttc    7560
tttagaatag ttgtttccag aggccaaaca ttccacccgt agtaaagtgc aagcgtagga    7620
agaccaagac tggcataaat caggtataag tgtcgagcac tggcaggtga tcttctgaaa    7680
gtttctacta gcagataaga tccagtagtc atgcatatgg caacaatgta ccgtgtggat    7740
ctaagaacgc gtcctactaa ccttcgcatt cgttggtcca gtttgttgtt atcgatcaac    7800
gtgacaaggt tgtcgattcc gcgtaagcat gcatacccaa ggacgcctgt tgcaattcca    7860
agtgagccag ttccaacaat cttttgtaata ttagagcact tcattgtgtt gcgcttgaaa    7920
gtaaaatgcg aacaaattaa gagataatct cgaaaccgcg acttcaaacg ccaatatgat    7980
gtgcggcaca caataagcgt tcatatccgc tgggtgactt tctcgcttta aaaaattatc    8040
cgaaaaaatt ttctagagtg ttgacacttt atacttccgg ctcgtataat acgacaaggt    8100
```

| | |
|---|---|
| gtaaggagga ctaaaccatg gctaaactca cctctgctgt tccagtcctg actgctcgtg | 8160 |
| atgttgctgg tgctgttgag ttctggactg atagactcgg tttctcccgt gacttcgtag | 8220 |
| aggacgactt tgccggtgtt gtacgtgacg acgttaccct gttcatctcc gcagttcagg | 8280 |
| accaggttgt gccagacaac actctggcat gggtatgggt tcgtggtctg gacgaactgt | 8340 |
| acgctgagtg gtctgaggtc gtgtctacca acttccgtga tgcatctggt ccagctatga | 8400 |
| ccgagatcgg tgaacagccc tggggtcgtg agtttgcact gcgtgatcca gctggtaact | 8460 |
| gcgtgcattt cgtcgcagaa gagcaggact aacctctagg acaccttacg attatttaga | 8520 |
| gagtatttat tagttttatt gtatgtatac ggatgtttta ttatctattt atgcccttat | 8580 |
| attctgtaac tatccaaaag tcctatctta tcaagccagc aatctatgtc cgcgaacgtc | 8640 |
| aactaaaaat aagcttttta tgctcttctc tctttttttc ccttcggtat aattatacct | 8700 |
| tgcatccaca gattctcctg ccaaattttg cataatcctt tacaacatgg ctatatggga | 8760 |
| gcacttagcg ccctccaaaa cccatattgc ctacgcatgt ataggtgttt tttccacaat | 8820 |
| attttctctg tgctctcttt ttattaaaga gaagctctat atcggagaag cttctgtggc | 8880 |
| cgttatattc ggcctatcg tgggaccaca ttgcctgaat tggtttgccc cggaagattg | 8940 |
| gggaaacttg gatctgatta ccttagctgc aggtaccact gagcgtcaga ccccgtagaa | 9000 |
| aagatcaaag gatcttcttg agatcctttt tttctgcgcg taatctgctg cttgcaaaca | 9060 |
| aaaaaaccac cgctaccagc ggtggtttgt ttgccggatc aagagctacc aactcttttt | 9120 |
| ccgaaggtaa ctggcttcag cagagcgcag ataccaaata ctgttcttct agtgtagccg | 9180 |
| tagttaggcc accacttcaa gaactctgta gcaccgccta catacctcgc tctgctaatc | 9240 |
| ctgttaccag tggctgctgc cagtggcgat aagtcgtgtc ttaccgggtt ggactcaaga | 9300 |
| cgatagttac cggataaggc gcagcggtcg ggctgaacgg ggggttcgtg cacacagccc | 9360 |
| agcttggagc gaacgaccta caccgaactg agatacctac agcgtgagct atgagaaagc | 9420 |
| gccacgcttc ccgaagggag aaaggcggac aggtatccgg taagcggcag ggtcggaaca | 9480 |
| ggagagcgca cgagggagct tccaggggga aacgcctggt atctttatag tcctgtcggg | 9540 |
| tttcgccacc tctgacttga gcgtcgattt ttgtgatgct cgtcaggggg cggagccta | 9600 |
| tggaaaaacg ccagcaacgc ggccttttta cggttcctgg ccttttgctg ccttttgct | 9660 |
| cacatcg | 9667 |

<210> SEQ ID NO 5
<211> LENGTH: 9456
<212> TYPE: DNA
<213> ORGANISM: Artificial Sequence
<220> FEATURE:
<223> OTHER INFORMATION: synthetic vector sequence

<400> SEQUENCE: 5

| | |
|---|---|
| aattcggatc taataaaata tctttatttt cattacatct gtgtgttggt tttttgtgtg | 60 |
| gatcttcaat attggccatt agccatatta ttcattggtt atatagcata atcaatatt | 120 |
| ggctattggc cattgcatac gttgtatcta tatcataata tgtacattta tattggctca | 180 |
| tgtccaatat gaccgccatg ttggcattga ttattgacta gttattaata gtaatcaatt | 240 |
| acggggtcat tagttcatag cccatatatg gagttccgcg ttacataact tacggtaaat | 300 |
| ggcccgcctg gctgaccgcc caacgacccc cgcccattga cgtcaataat gacgtatgtt | 360 |
| cccatagtaa cgccaatagg gactttccat tgacgtcaat gggtggagta tttacggtaa | 420 |
| actgcccact tggcagtaca tcaagtgtat catatgccaa gtacgccccc tattgacgtc | 480 |

```
aatgacggta aatggcccgc ctggcattat gcccagtaca tgaccttatg ggactttcct      540
acttggcagt acatctacgt attagtcatc gctattacca tggtgatgcg gttttggcag      600
tacatcaatg ggcgtggata gcggtttgac tcacggggat ttccaagtct ccaccccatt      660
gacgtcaatg ggagtttgtt ttggcaccaa aatcaacggg actttccaaa atgtcgtaac      720
aactccgccc cattgacgca aatgggcggt aggcgtgtac ggtgggaggt ctatataagc      780
agagctcgtt tagtgaaccg tcagatcgcc tggagacgcc atccacgctg ttttgacctc      840
catagaagac accgggaccg atccagcctc cgcggccggg aacggtgcat tggaacgcgg      900
attccccgtg ccaagagtga cgtaagtacc gcctatagag tctataggcc cacccccttg      960
gcttcgttag aacgcggcta caattaatac ataaccttat gtatcataca catacgattt     1020
aggtgacact atagaataac atccactttg cctttctctc cacaggtgtc cactcccagg     1080
tccaactgca cctcggttct atcgaaaacg cgcctctaga cctgcaggcc accatggccc     1140
ccgtggccgt gtgggccgcc ctggccgtgg gctggagct gtgggccgcc gcccacgccc      1200
tgcccgccca ggtggccttc accccctacg ccccccgagcc cggctccacc tgccggctgc     1260
gggagtacta cgaccagacc gcccagatgt gctgctccaa gtgctccccc ggccagcacg     1320
ccaaggtgtt ctgcaccaag acctccgaca ccgtgtgcga ctcctgcgag gactccacct     1380
acacccagct gtggaactgg gtgcccgagt gcctgtcctg cggctcccgg tgctcctccg     1440
accaggtgga gacccaggcc tgcacccggg agcagaaccg gatctgcacc tgccggcccg     1500
gctggtactg cgccctgtcc aagcaggagg gctgccggct gtgcgccccc ctgcggaagt     1560
gccggcccgg cttcggcgtg gcccggcccg gcaccgagac ctccgacgtg gtgtgcaagc     1620
cctgcgcccc cggcaccttc tccaacacca cctcctccac cgacatctgc cggccccacc     1680
agatctgcaa cgtggtggcc atccccggca acgcctccat ggacgccgtg tgcacctcca     1740
cctcccccac ccggtccatg gcccccgcg ccgtgcacct gccccagccc gtgtccaccc      1800
ggtcccagca cacccagccc accccgagc cctccaccgc cccctccacc tccttcctgc      1860
tgcccatggg ccctccccc ccgccgagg ctccaccgg cgacgagccc aagtcctgcg       1920
acaagaccca cacctgcccc ccctgccccg ccccgagct gctgggcggc cctccgtgt       1980 tcctgttccc ccccaagccc aaggacaccc tgatgatctc ccggacccc gaggtgacct      2040 gcgtggtggt ggacgtgtcc cacgaggacc ccgaggtgaa gttcaactgg tacgtggacg     2100
gcgtggaggt gcacaacgcc aagaccaagc ccgggagga gcagtacaac tccacctacc     2160
gggtggtgtc cgtgctgacc gtgctgcacc aggactggct gaacggcaag gagtacaagt     2220
gcaaggtgtc caacaaggcc ctgcccgccc catcgagaa gaccatctcc aaggccaagg     2280
gccagccccg ggagccccag gtgtacaccc tgccccctc ccgggaggag atgaccaaga     2340
accaggtgtc cctgacctgc ctggtgaagg gcttctaccc ctccgacatc gccgtggagt     2400
gggagtccaa cggccagccc gagaacaact acaagaccac ccccccgtg ctggactccg     2460 acggctcctt cttcctgtac tccaagctga ccgtggacaa gtcccggtgg cagcagggca     2520
acgtgttctc ctgctccgtg atgcacgagg ccctgcacaa ccactacacc cagaagtccc     2580
tgtccctgtc ccccggcaag tgatgaggcg cgccctaga gtcgaccgg gcggccgctt      2640 cccttagtg agggttaatg cttcgagcga ctgtgccttc tagttgccag ccatctgttg      2700
tttgcccctc ccccgtgcct tccttgaccc tggaaggtgc cactcccact gtcctttcct     2760
aataaaatga ggaaattgca tcgcattgtc tgagtaggtg tcattctatt ctgggggtg      2820
```

```
gggtggggca ggacagcaag ggggaggatt gggaagacaa tagcaggcat gctggggatg    2880
cggtgggctc tatggaaatc cgataaggat cgatccgggc tggcgtaata gcgaagaggc    2940
ccgcaccgat cgcccttccc aacagttgcg cagcctgaat ggcgaatgga cgcgccctgt    3000
agcggcgcat taagcgcggc gggtgtggtg gttacgcgca gcgtgaccgc tacacttgcc    3060
agcgccctag cgcccgctcc tttcgctttc ttcccttcct ttctcgccac gttcgccggc    3120 tttcccgtc aagctctaaa tcggggctc cctttagggt tccgatttag agctttacgg      3180
cacctcgacc gcaaaaaact tgatttgggt gatggttcac gtagtgggcc atcgccctga    3240
tagacggttt ttcgcccttt gacgttggag tccacgttct ttaatagtgg actcttgttc    3300
caaactggaa caacactcaa ccctatctcg gtctattctt ttgatttata agggattttg    3360
ccgatttcgg cctattggtt aaaaaatgag ctgatttaac aaatatttaa cgcgaatttt    3420
aacaaaatat taacgtttac aatttcgcct gatgcggtat tttctcctta cgcatctgtg    3480
cggtatttca caccgcatac gcggatcttt ggggttgcgc cttttccaag gcagccctgg    3540
gtttgcgcag ggacgcggct gctctgggcg tggttccggg aaacgcagcg cgccgaccc     3600 tgggtctcgc acattcttca cgtccgttcg cagcgtcacc cggatcttcg ccgctaccct    3660
tgtgggcccc ccgcgacgc ttcctgctcc gccctaagt cgggaaggtt ccttgcggtt      3720
cgcggcgtgc cggacgtgac aaacggaagc cgcacgtctc actagtaccc tcgcagacgg    3780
acagcgccag ggagcaatgg cagcgcgccg accgcgatgg gctgtggcca atagcggctg    3840
ctcagcaggg cgcgccgaga gcagcggccg ggaaggggcg gtgcgggagg cggggtgtgg    3900
ggcggtagtg tgggccctgt tcctgcccgc gcggtgttcc gcattctgca agcctccgga    3960
gcgcacgtcg gcagtcggct ccctcgttga ccgaatcacc gacctctctc cccaggggga    4020
tccaccggag cttaccatga ccgagtacaa gcccacggtg cgcgctagcg ctaccggtcg    4080
ccaccatgat tgaacaagat ggattgcacg caggttctcc ggccgcttgg gtggagaggc    4140
tattcggcta tgactgggca caacagacaa tcggctgctc tgatgccgcc gtgttccggc    4200
tgtcagcgca ggggcgcccg gttcttttg tcaagaccga cctgtccggt gccctgaatg     4260
aactgcagga cgaggcagcg cggctatcgt ggctggccac gacgggcgtt ccttgcgcag    4320
ctgtgctcga cgttgtcact gaagcgggaa gggactggct gctattgggc gaagtgccgg    4380
ggcaggatct cctgtcatct caccttgctc ctgccgagaa agtatccatc atggctgatg    4440
caatgcggcg gctgcatacg cttgatccgg ctacctgccc attcgaccac caagcgaaac    4500
atcgcatcga gcgagcacgt actcggatgg aagccggtct tgtcgatcag gatgatctgg    4560
acgaagagca tcagggcctc gcgccagccg aactgttcgc caggctcaag gcgcgcatgc    4620
ccgacggcga ggatctcgtc gtgacccatg gcgatgcctg cttgccgaat atcatggtgg    4680
aaaatggccg cttttctgga ttcatcgact gtggccggct gggtgtggcg gaccgctatc    4740
aggacatagc gttggctacc cgtgatattg ctgaagagct tggcggcgaa tgggctgacc    4800
gcttcctcgt gctttacggt atcgccgctc ccgattcgca gcgcatcgcc ttctatcgcc    4860
ttcttgacga gttcttctga gcgggactct ggggttcgaa atgaccgacc aagcgacgcc    4920
caacctgcca tcacgatggc cgcgatgagt cgacccgggc ggccgcttcc ctttagtgag    4980
ggttaatgct tcgagactcc tcaggtgcag gctgcctatc agaaggtggt ggctggtgtg    5040
gccaatgccc tggctcacaa ataccactga gatctttttc cctctgccaa aaattatggg    5100
gacatcatga agccccttga gcatctgact tctggctaat aaaggaaatt tattttcatt    5160
gcaatagtgt gttggaattt tttgtgtctc tcactcggaa ggacatatgg gagggcaaat    5220
```

```
catttaaaac atcagaatga gtatttggtt tagagtttgg caacatatgc ccatatgctg      5280
gctgccatga acaaaggttg gctataaaga ggtcatcagt atatgaaaca gcccctgct       5340 gtccattcct tattccatag aaaagccttg acttgaggtt agatttttt tatattttgt       5400 tttgtgttat tttttctttt aacatcccta aaattttcct tacatgtttt actagccaga     5460 ttttcctcc tctcctgact actcccagtc atagctgtcc ctcttctctt atggagatcc       5520
ctcgacaatc gatagcgata aggatccgcg tatggtgcac tctcagtaca atctgctctg     5580
atgccgcata gttaagccag ccccgacacc cgccaacacc cgctgacgcg ccctgacggg     5640
cttgtctgct cccggcatcc gcttacgac aagctgtgac cgtctccggg agctgcatgt      5700
gtcagaggtt ttcaccgtca tcaccgaaac gcgcgagacg aaagggcctc gtgatacgcc     5760 tattttata ggttaatgtc atgataataa tggtttctta gacgtcaggt ggcactttc       5820 ggggaaatgt gcgcggaacc cctatttgtt tattttcta aatacattca aatatgtatc      5880
cgcttaccaa tgcttaatca gtgaggcacc tatctcagcg atctgtctat ttcgttcatc     5940
catagttgcc tgactccccg tcgtgtagat aactacgata cgggagggct taccatctgg    6000
ccccagtgct gcaatgatac cgcgggaccc acgctcaccg gctccagatt tatcagcaat    6060
aaaccagcca gccggaaggg ccgagcgcag aagtggtcct gcaactttat ccgcctccat    6120
ccagtctatt aattgttgcc gggaagctag agtaagtagt tcgccagtta atagtttgcg    6180
caacgttgtt gccattgcta caggcatcgt ggtgtcacgc tcgtcgtttg gtatggcttc    6240
attcagctcc ggttcccaac gatcaaggcg agttacatga tcccccatgt tgtgcaaaaa   6300
agcggttagc tccttcggtc ctccgatcgt tgtcagaagt aagttggccg cagtgttatc    6360
actcatggtt atggcagcac tgcataattc tcttactgtc atgccatccg taagatgctt    6420
ttctgtgact ggtgagtact caaccaagtc attctgagaa tagtgtatgc ggcgaccgag    6480
ttgctcttgc ccggcgtcaa tacgggataa taccgcgcca catagcagaa ctttaaaagt    6540
gctcatcatt ggaaaacgtt cttcggggcg aaaactctca aggatcttac cgctgttgag    6600
atccagttcg atgtaaccca ctcgtgcacc caactgatct tcagcatctt ttactttcac    6660
cagcgtttct gggtgagcaa aaacaggaag gcaaaatgcc gcaaaaaagg gaataagggc    6720
gacacggaaa tgttgaatac tcatactctt ccttttcaa tattattgaa gcatttatca     6780
gggttattgt ctcatgagcg gatacatatt tgaatgtatt tagaaaaata acaaataggg    6840
ggttccgcgc acatttcccc gaaaagtgcc acctgtcatg accaaaatcc cttaacgtga    6900
gttttcgttc cactgagcgt cagacccccgt agaaaagatc aaaggatctt cttgagatcc   6960
tttttttctg cgcgtaatct gctgcttgca acaaaaaaa ccaccgctac cagcggtggt    7020
ttgtttgccg gatcaagagc taccaactct ttttccgaag gtaactggct tcagcagagc    7080
gcagatacca aatactgttc ttctagtgta gccgtagtta ggccaccact tcaagaactc    7140
tgtagcaccg cctacatacc tcgctctgct aatcctgtta ccagtggctg ctgccagtgg    7200
cgataagtcg tgtcttaccg ggttggactc aagacgatag ttaccggata aggcgcagcg    7260
gtcgggctga acgggggggtt cgtgcacaca gcccagcttg gagcgaacga cctacaccga    7320
actgagatac ctacagcgtg agctatgaga aagcgccacg cttcccgaag ggagaaaggc    7380
ggacaggtat ccggtaagcg gcagggtcgg aacaggagag cgcacgaggg agcttccagg    7440
gggaaacgcc tggtatcttt atagtcctgt cgggtttcgc cacctctgac ttgagcgtcg    7500
atttttgtga tgctcgtcag gggggcggag cctatggaaa aacgccagca acgcgggctc    7560
```

```
gacagatcca tttaaatttt caccgtcatc accgaaacgc gcgaggcagc tgtggaatgt    7620
gtgtcagtta gggtgtggaa agtccccagg ctccccagca ggcagaagta tgcaaagcat    7680
gcatctcaat tagtcagcaa ccaggtgtgg aaagtcccca ggctcccag caggcagaag     7740 tatgcaaagc atgcatctca attagtcagc aaccatagtc ccgcccctaa ctccgcccat    7800
ccgcccccta actccgccca gttccgccca ttctccgccc catggctgac taatttttttt   7860 tatttatgca gaggccgagg ccgcctcggc cctctgagct attccagaag tagtgaggag    7920
gcttttttgg aggcctaggc ttttgcaaaa agctaattcg agctcggtac ccccaaactt    7980
gacggcaatc ctagcgtgaa ggctggtagg attttatccc cgctgccatc atggttcgac    8040
cattgaactg catcgtcgcc gtgtcccaaa atatggggat tggcaagaac ggagaccgac    8100
cctggcctcc gctcaggaac gagttcaagt acttccaaag aatgaccaca acctcttcag    8160
tggaaggtaa acagaatctg gtgattatgg gtaggaaaac ctggttctcc attcctgaga    8220
agaatcgacc tttaaaggac agaattaata tagttctcag tagagaactc aaagaaccac    8280
cacgaggagc tcattttctt gccaaaagtt tggatgatgc cttaagactt attgaacaac    8340
cggaattggc aagtaaagta gacatggttt ggatagtcgg aggcagttct gtttaccagg    8400
aagccatgaa tcaaccaggc cacctcagac tctttgtgac aaggatcatg caggaatttg    8460
aaagtgacac gttttttccca gaaattgatt tggggaaata taaacttctc ccagaatacc    8520
caggcgtcct ctctgaggtc caggaggaaa aaggcatcaa gtataagttt gaagtctacg    8580
agaagaaaga ctaacaggaa gatgctttca gttctctgc tcccctccta aagctatgca     8640
tttttataag accatggggg atgctcgatc ccctcgcgag ttggttcagc tgctgcctga    8700
ggctggacga cctcgcggag ttctaccggc agtgcaaatc cgtcggcatc caggaaacca    8760
gcagcggcta tccgcgcatc catgccccg aactgcagga gtggggaggc acgatggccg     8820
ctttggtccg gatctttgtg aaggaacctt acttctgtgg tgtgacataa ttggacaaac    8880
tacctacaga gatttaaagc tctaaggtaa atataaaatt tttaagtgta taatgtgtta    8940
aactactgat tctaattgtt tgtgtatttt agattccaac ctatggaact gatgaatggg    9000
agcagtggtg gaatgccttt aatgaggaaa acctgttttg ctcagaagaa atgccatcta    9060
gtgatgatga ggctactgct gactctcaac attctactcc tccaaaaaag aagagaaagg    9120
tagaagaccc caaggacttt ccttcagaat tgctaagttt tttgagtcat gctgtgttta    9180
gtaatagaac tcttgcttgc tttgctattt acaccacaaa ggaaaaagct gcactgctat    9240
acaagaaaat tatggaaaaa tattctgtaa cctttataag taggcataac agttataatc    9300
ataacatact gttttttctt actccacaca ggcatagagt gtctgctatt aataactatg    9360
ctcaaaaatt gtgtaccttt agcttttaa tttgtaaagg ggttaataag gaatatttga    9420
tgtatagtgc cttgactaga gatcataatc agccag                              9456
```

<210> SEQ ID NO 6
<211> LENGTH: 10783
<212> TYPE: DNA
<213> ORGANISM: Artificial Sequence
<220> FEATURE:
<223> OTHER INFORMATION: synthetic vector sequence

<400> SEQUENCE: 6

```
aattcggatc tgcgcagcac catggcctga ataacctct gaaagaggaa cttggttagg       60
taccttctga ggcggaaaga accagctgtg gaatgtgtgt cagttagggt gtggaaagtc     120
cccaggctcc ccagcaggca gaagtatgca aagcatgcat ctcaattagt cagcaaccag    180
```

```
gtgtggaaag tccccaggct ccccagcagg cagaagtatg caaagcatgc atctcaatta      240
gtcagcaacc atagtcccgc ccctaactcc gcccatcccg cccctaactc cgcccagttc      300
cgcccattct ccgccccatg gctgactaat ttttttttatt tatgcagagg ccgaggccgc     360
ctcggcctct gagctattcc agaagtagtg aggaggcttt tttggaggcc taggcttttg      420
caaaaagctt ctcgaggaac ttcagggtga gtctatggga cccttgatgt tttctttccc      480
cttcttttct atggttaagt tcatgtcata ggaaggggag aagtaacagg gtacagttta      540
gaatgggaaa cagacgaatg attgcatcag tgtggaagtc tcaggatcgt tttagtttct      600
tttatttgct gttcataaca attgttttct tttgtttaat tcttgctttc ttttttttc       660 ttctccgcaa ttttttactat tatacttaat gccttaacat tgtgtataac aaaaggaaat    720
atctctgaga tacattaagt aacttaaaaa aaaactttac acagtctgcc tagtacatta     780
ctatttggaa tatatgtgtg cttatttgca tattcataat ctccctactt tattttcttt    840 tattttttaat tgatacataa tcattataca tatttatggg ttaaagtgta atgttttaat   900
atgtgtacac atattgacca aatcagggta attttgcatt tgtaatttta aaaaatgctt     960
tcttctttta atatactttt ttgtttatct tatttctaat actttcccta atctctttct   1020
ttcagggcaa taatgataca atgtatcatg cctctttgca ccattctaaa gaataacagt   1080
gataatttct gggttaaggc aatagcaata tttctgcata taaatatttc tgcatataaa   1140
ttgtaactga tgtaagaggt ttcatattgc taatagcagc tacaatccag ctaccattct   1200
gcttttattt tatggttggg ataaggctgg attattctga gtccaagcta ggcctttttg    1260
ctaatcatgt tcatacctct tatcttcctc ccacagctcc tgggcagtgt ccactcccag    1320
gtccaactgc acctcggttc tatcgaaaac gcgtccacca tgaagtgggt gaccttcatc    1380
tccctgctgt tcctgttctc ctccgcctac tccctgcccg ccaggtggc cttcaccccc    1440 tacgccccg agcccggctc cacctgccgg ctgcgggagt actacgacca gaccgcccag    1500
atgtgctgct ccaagtgctc ccccggccag cacgccaagg tgttctgcac caagacctcc   1560
gacaccgtgt gcgactcctg cgaggactcc acctacaccc agctgtggaa ctgggtgccc   1620
gagtgcctgt cctgcggctc ccggtgctcc tccgaccagg tggagaccca ggcctgcacc   1680
cgggagcaga accggatctg cacctgccgg cccggctggt actgcgccct gtccaagcag   1740
gagggctgcc ggctgtgcgc ccccctgcgg aagtgccggc ccggcttcgg cgtggcccgg   1800
cccggcaccg agacctccga cgtggtgtgc aagccctgcg cccccggcac cttctccaac   1860
accacctcct ccaccgacat ctgccggccc caccagatct gcaacgtggt ggccatcccc   1920
ggcaacgcct ccatggacgc cgtgtgcacc tccacctccc ccaccggtc catggccccc   1980 ggcgccgtgc acctgcccca gccgtgtcc accggtccc agcacaccca gcccacccc    2040 gagccctcca ccgcccctc cacctccttc ctgctgccca tgggccccctc ccccccgcc    2100 gagggctcca ccgcgacga gcccaagtcc tgcgacaaga cccacacctg ccccccctgc    2160
cccgcccccg agctgctggg cggccctcc gtgttcctgt tccccccaa gcccaaggac    2220 accctgatga tctcccggac ccccgaggtg acctgcgtgg tggtggacgt gtcccacgag    2280
gaccccgagg tgaagttcaa ctggtacgtg gacggcgtgg aggtgcacaa cgccaagacc    2340
aagccccggg aggagcagta caactccacc taccgggtgg tgtccgtgct gaccgtgctg    2400
caccaggact ggctgaacgg caaggagtac aagtgcaagg tgtccaacaa ggccctgccc    2460
gcccccatcg agaagaccat ctccaaggcc aagggccagc ccgggagcc ccaggtgtac    2520
```

```
accctgcccc cctccgggga ggagatgacc aagaaccagg tgtccctgac ctgcctggtg    2580
aagggcttct accctccga catcgccgtg gagtgggagt ccaacggcca gcccgagaac    2640
aactacaaga ccaccccccc cgtgctggac tccgacggct ccttcttcct gtactccaag    2700
ctgaccgtgg acaagtcccg gtggcagcag ggcaacgtgt tctcctgctc cgtgatgcac    2760
gaggccctgc acaaccacta cacccagaag tccctgtccc tgtccccgg caagtgatga    2820 ggcgcgcccc tagagtcgac ccgggcggcc gcttcccttt agtgagggtt aatgcttcga    2880
gcagacatga taagatacat tgatgagttt ggacaaacca aactagaat gcagtgaaaa    2940 aaatgcttta tttgtgaaat ttgtgatgct attgctttat ttgtaaccat tataagctgc    3000
aataaacaag ttaacaacaa caattgcatt cattttatgt ttcaggttca gggggagatg    3060
tgggaggttt tttaaagcaa gtaaaacctc tacaaatgtg gtaaaatccg ataaggatcg    3120
atccgggctg gcgtaatagc gaagaggccc gcaccgatcg cccttcccaa cagttgcgca    3180
gcctgaatgg cgaatggaac gcgcctgta gcggcgcatt aagcgcggcg ggtgtggtgg    3240
ttacgcgcag cgtgaccgct acacttgcca gcgccctagc gcccgctcct ttcgctttct    3300
tcccttcctt tctcgccacg ttcgccggct ttccccgtca gctctaaat cggggggctcc    3360 ctttaggggt ccgatttaga gctttacggc acctcgaccg caaaaaactt gatttgggtg    3420
atggttcacg tagtgggcca tcgccctgat agacggtttt tcgccctttg acgttggagt    3480
ccacgttctt taatagtgga ctcttgttcc aaactggaac aacactcaac cctatctcgg    3540
tctattcttt tgatttataa gggattttgc cgatttcggc ctattggtta aaaaatgagc    3600
tgatttaaca atatttaac gcgaatttta acaaaatatt aacgtttaca atttcgcctg    3660
atgcggtatt ttctccttac gcatctgtgc ggtatttcac accgcatacg cggatctgct    3720
ttgcttctca atttcttatt tgcataatga gaaaaaagg aaaattaatt ttaacaccaa    3780
ttcagtagtt gattgagcaa atgcgttgcc aaaaggatg ctttagagac agtgttctct    3840
gcacagataa ggacaaacat tattcagagg gagtacccag agctgagact cctaagccag    3900
tgagtggcac agcattctag ggagaaatat gcttgtcatc accgaagcct gattccgtag    3960
agccacacct tggtaagggc caatctgctc acacaggata gagagggcag gagccagggc    4020
agagcatata aggtgaggta ggatcagttg ctcctcacat ttgcttctga catagttgtg    4080
ttggctagcg ctaccggtcg ccaccatgat tgaacaagat ggattgcacg caggttctcc    4140
ggccgcttgg gtggagaggc tattcggcta tgactgggca acagacaa tcggctgctc    4200 tgatgccgcc gtgttccggc tgtcagcgca ggggcgcccg gttcttttg tcaagaccga    4260 cctgtccggt gccctgaatg aactgcagga cgaggcagcg cggctatcgt ggctggccac    4320
gacgggcgtt ccttgcgcag ctgtgctcga cgttgtcact gaagcgggaa gggactggct    4380
gctattgggc gaagtgccgg ggcaggatct cctgtcatct caccttgctc ctgccgagaa    4440
agtatccatc atggctgatg caatgcggcg gctgcatacg cttgatccgg ctacctgccc    4500
attcgaccac caagcgaaac atcgcatcga gcgagcacgt actcggatgg aagccggtct    4560
tgtcgatcag gatgatctgg acgaagagca tcaggggctc gcgccagccg aactgttcgc    4620
caggctcaag gcgcgcatgc ccgacggcga ggatctcgtc gtgacccatg gcgatgcctg    4680
cttgccgaat atcatggtgg aaaatggccg cttttctgga ttcatcgact gtggccggct    4740
gggtgtggcg gaccgctatc aggacatagc gttggctacc cgtgatattg ctgaagagct    4800
tggcggcgaa tgggctgacc gcttcctcgt gctttacggt atcgccgctc ccgattcgca    4860
gcgcatcgcc ttctatcgcc ttcttgacga gttcttctga cgactgtgcc ttctagttgc    4920
```

```
cagccatctg ttgtttgccc ctccccgtg ccttccttga ccctggaagg tgccactccc    4980
actgtccttt cctaataaaa tgaggaaatt gcatcgcatt gtctgagtag gtgtcattct    5040
attctggggg gtggggtggg gcaggacagc aaggggagg attgggaaga caatagcagg    5100
catgctgggg atgcggtggg ctctatggaa tcgatagcga taaggatccg cgtatggtgc    5160
actctcggtt gccgccgggc gttttttatt ggtgagaatc caagctagag gcatcaaata    5220
aaacgaaagg ctcagtcgaa agactgggcc tttcgtttta tctgttgttt gtcggtgaac    5280
gctctcctga gtaggacaaa tccgccgccc tagacctagg gatatattcc gcttcctcgc    5340
tcactgactc gctacgctcg gtcgttcgac tgcggcgagc ggaaatggct tacgaacggg    5400
gcggagattt cctggaagat gccaggaaga tacttaacag ggaagtgaga gggccgcggc    5460
aaagccgttt ttccataggc tccgcccccc tgacaagcat cacgaaatct gacgctcaaa    5520
tcagtggtgg cgaaacccga caggactata agataccag gcgtttcccc ctggcggctc    5580
cctcgtgcgc tctcctgttc ctgcctttcg gtttaccggt gtcattccgc tgttatggcc    5640
gcgtttgtct cattccacgc ctgacactca gttccgggta ggcagttcgc tccaagctgg    5700
actgtatgca cgaaccccc gttcagtccg accgctgcgc cttatccggt aactatcgtc    5760
ttgagtccaa cccggaaaga catgcaaaag caccactggc agcagccact ggtaattgat    5820
ttagaggagt tagtcttgaa gtcatgcgcc ggttaaggct aaactgaaag gacaagtttt    5880
ggtgactgcg ctcctccaag ccagttacct cggttcaaag agttggtagc tcagagaacc    5940
ttcgaaaaac cgccctgcaa ggcggttttt tcgttttcag agcaagagat tacgcgcaga    6000
ccaaaacgat ctcaagaaga tcatcttatt aatcagataa aatatttcta gatttcagtg    6060
caatttatct cttcaaatgt agcacctgaa gtcagcccca tacgatataa gttgttacta    6120
gtgcttggat tctcaccaat aaaaaacgcc cggcggcaac cgagcgttct gaacaaatcc    6180
agatggagtt ctgaggtcat tactggatct atcaacagga gtccaagcga gctcgatatc    6240
cgtcggcttg aacgaattgt tagacattat ttgccgacta ccttggtgat ctcgcctttc    6300
acgtagtgga caaattcttc caactgatct gcgcgcgagg ccaagcgatc ttcttcttgt    6360
ccaagataag cctgtctagc ttcaagtatg acgggctgat actgggccgg caggcgctcc    6420
attgcccagt cggcagcgac atccttcggc gcgattttgc cggttactgc gctgtaccaa    6480
atgcgggaca acgtaagcac tacatttcgc tcatcgccag cccagtcggg cggcgagttc    6540
catagcgtta aggtttcatt tagcgcctca aatagatcct gttcaggaac cggatcaaag    6600
agttcctccg ccgctggacc taccaaggca acgctatgtt ctcttgcttt tgtcagcaag    6660
atagccagat caatgtcgat cgtggctggc tcgaagatac ctgcaagaat gtcattgcgc    6720
tgccattctc caaattgcag ttcgcgctta gctggataac gccacggaat gatgtcgtcg    6780
tgcacaacaa tggtgacttc tacagcgcgg agaatctcgc tctctccagg ggaagccgaa    6840
gtttccaaaa ggtcgttgat caaagctcgc cgcgttgttt catcaagcct tacggtcacc    6900
gtaaccagca aatcaatatc actgtgtggc ttcaggccgc catccactgc ggagccgtac    6960
aaatgtacgg ccagcaacgt cggttcgaga tggcgctcga tgacgccaac tacctctgat    7020
agttgagtcg atacttcggc gatcaccgct tccctcatga tgtttaactt tgttttaggg    7080
cgactgccct gctgcgtaac atcgttgctg ctccataaca tcaaacatcg acccacggcg    7140
taacgcgctt gctgcttgga tgcccgaggc atagactgta ccccaaaaaa acagtcataa    7200
caagccatga aaaccgccac tgcgccgtta ccaccgctgc gttcggtcaa ggttctggac    7260
```

```
cagttgcgtg agcgcatacg ctacttgcat tacagcttac gaaccgaaca ggcttatgtc    7320
cactgggttc gtgccttcat ccggatatcg acgtctgtgt ggaattgtga gcggataaca    7380
aattcacaca gggccctcgg acaccgagga gaatgtcaag aggcgaacac acaacgtctt    7440
ggagcgccag aggaggaacg agctaaaacg gagcttttttt gccctgcgtg accagatccc    7500
ggagttggaa acaatgaaa atggctcgac agatccattt aaattttcac cgtcatcacc    7560
gaaacgcgcg aggcagctgt gcgtgaggct ccggtgcccg tcagtgggca gagcgcacat    7620
cgcccacagt ccccgagaag ttgggggggag gggtcggcaa ttgaaccggt gcctagagaa    7680
ggtggcgcgg ggtaaactgg gaaagtgatg tcgtgtactg gctccgcctt tttcccgagg    7740
gtgggggaga accgtatata agtgcagtag tcgccgtgaa cgttcttttt cgcaacgggt    7800
ttgccgccag aacacaggta agtgccgtgt gtggttcccg cgggcctggc ctctttacgg    7860
gttatggccc ttgcgtgcct tgaattactt ccacctggct gcagtacgtg attcttgatc    7920
ccgagcttcg ggttggaagt gggtgggaga gttcgaggcc ttgcgcttaa ggagccccctt    7980
cgcctcgtgc ttgagttgag gcctggcctg gcgctgggg ccgccgcgtg cgaatctggt    8040
ggcaccttcg cgcctgtctc gctgcttttcg ataagtctct agccatttaa aatttttgat    8100
gacctgctgc gacgcttttt ttctggcaag atagtcttgt aaatgcgggc caagatctgc    8160
acactggtat ttcggttttt ggggccgcgg gcggcgacgg ggcccgtgcg tcccagcgca    8220
catgttcggc gaggcgggc ctgcgagcgc ggccaccgag aatcggacgg gggtagtctc    8280
aagctggccg gcctgctctg gtgcctggcc tcgcgccgcc gtgtatcgcc ccgccctggg    8340
cggcaaggct ggcccggtcg gcaccagttg cgtgagcgga aagatggccg cttcccggcc    8400
ctgctgcagg gagctcaaaa tggaggacgc ggcgctcggg agagcgggcg ggtgagtcac    8460
ccacacaaag gaaagggcc tttccgtcct cagccgtcgc ttcatgtgac tccacgagt    8520
accgggcgcc gtccaggcac ctcgattagt tctcgagctt ttggagtacg tcgtcttag    8580
gttgggggga ggggttttat gcgatggagt ttccccacac tgagtgggtg gagactgaag    8640
ttaggccagc ttggcacttg atgtaattct ccttggaatt tgccctttttt gagtttggat    8700
cttggttcat tctcaagcct cagacagtgg ttcaaagttt ttttcttcca tttcaggtgt    8760
cgtgaaattc gagctcggta ccccccaaact tgacggcaat cctagcgtga aggctggtag    8820
gattttatcc ccgctgccat catggttcga ccattgaact gcatcgtcgc cgtgtcccaa    8880
aatatgggga ttggcaagaa cggagaccga ccctggcctc cgctcaggaa cgagttcaag    8940
tacttccaaa gaatgaccac aacctcttca gtggaaggta aacagaatct ggtgattatg    9000
ggtaggaaaa cctggttctc cattcctgag aagaatcgac ctttaaagga cagaattaat    9060
atagttctca gtagagaact caaagaacca ccacgaggag ctcattttct tgccaaaagt    9120
ttggatgatg ccttaagact tattgaacaa ccggaattgg caagtaaagt agacatggtt    9180
tggatagtcg gaggcagttc tgtttaccag gaagccatga atcaaccagg ccacctcaga    9240
ctctttgtga caaggatcat gcaggaattt gaaagtgaca cgttttttccc agaaattgat    9300
ttggggaaat ataaacttct cccagaatac ccaggcgtcc tctctgaggt ccaggaggaa    9360
aaaggcatca agtataagtt tgaagtctac gagaagaaag actaacagga agatgctttc    9420
aagttctctg ctcccctcct aaagctatgc atttttataa gaccatgggg gatgctcgat    9480
cccctcgcga gttggttcag ctgctgcctg aggctggacg acctcgcgga gttctaccgg    9540
cagtgcaaat ccgtcggcat ccaggaaacc agcagcggct atccgcgcat ccatgccccc    9600
gaactgcagg agtggggagg cacgatggcc gctttggtcc ggatctttgt gaaggaacct    9660
```

```
tacttctgtg gtgtgacata attggacaaa ctacctacag agatttaaag ctctaaggta    9720
aatataaaat ttttaagtgt ataatgtgtt aaactactga ttctaattgt ttgtgtattt    9780
tagattccaa cctatggaac tgatgaatgg gagcagtggt ggaatgcctt taatgaggaa    9840
aacctgtttt gctcagaaga aatgccatct agtgatgatg aggctactgc tgactctcaa    9900
cattctactc ctccaaaaaa gaagagaaag gtagaagacc ccaaggactt tccttcagaa    9960
ttgctaagtt ttttgagtca tgctgtgttt agtaatagaa ctcttgcttg ctttgctatt   10020
tacaccacaa aggaaaaagc tgcactgcta tacaagaaaa ttatggaaaa atattctgta   10080
acctttataa gtaggcataa cagttataat cataacatac tgtttttcct tactccacac   10140
aggcatagag tgtctgctat taataactat gctcaaaaat tgtgtacctt tagcttttta   10200
atttgtaaag gggttaataa ggaatatttg atgtatagtg ccttgactag aactcctcag   10260
gtgcaggctg cctatcagaa ggtggtggct ggtgtggcca atgccctggc tcacaaatac   10320
cactgagatc tttttccctc tgccaaaaat tatggggaca tcatgaagcc ccttgagcat   10380
ctgacttctg gctaataaag gaaatttatt ttcattgcaa tagtgtgttg gaattttttg   10440
tgtctctcac tcggaaggac atatgggagg gcaaatcatt taaaacatca gaatgagtat   10500
ttggtttaga gtttggcaac atatgcccat atgctggctg ccatgaacaa aggttggcta   10560
taaagaggtc atcagtatat gaaacagccc cctgctgtcc attccttatt ccatagaaaa   10620
gccttgactt gaggttagat tttttttata ttttgttttg tgttattttt tctttaaca    10680 tccctaaaat tttccttaca tgttttacta gccagatttt tcctcctctc ctgactactc   10740
ccagtcatag ctgtccctct tctcttatgg agatccctcg acg                     10783

<210> SEQ ID NO 7
<211> LENGTH: 9709
<212> TYPE: DNA
<213> ORGANISM: Artificial Sequence
<220> FEATURE:
<223> OTHER INFORMATION: synthetic vector sequence

<400> SEQUENCE: 7
aattcggatc tggctccggt gcccgtcagt gggcagagcg cacatcgccc acagtccccg     60
agaagttggg gggaggggtc ggcaattgaa ccggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
aggtaagtgc cgtgtgtggt tcccgcgggc ctggcctctt tacgggttat ggcccttgcg    300
tgccttgaat tacttccacc tggctgcagt acgtgattct tgatcccgag cttcgggttg    360
gaagtgggtg ggagagttcg aggccttgcg cttaaggagc cccttcgcct cgtgcttgag    420
ttgaggcctg gcctgggcgc tggggccgcc gcgtgcgaat ctggtggcac cttcgcgcct    480
gtctcgctgc tttcgataag tctctagcca tttaaatttt tgatgacct gctgcgacgc    540 tttttttctg gcaagatagt cttgtaaatg cgggccaaga tctgcacact ggtatttcgg    600
tttttggggc cgcgggcggc gacgggcccc gtgcgtccca gcgcacatgt tcggcgaggc    660
ggggcctgcg agcgcggcca ccgagaatcg acgggggta gtctcaagct ggccggcctg    720
ctctggtgcc tggtctcgcg ccgccgtgta tcgccccgcc ctgggcggca aggctggccc    780
ggtcggcacc agttgcgtga gcggaaagat ggccgcttcc cggccctgct gcagggagct    840
caaaatggag gacgcggcgc tcgggagagc gggcgggtga gtcacccaca caaaggaaaa    900
```

```
gggcctttcc gtcctcagcc gtcgcttcat gtgactccac ggagtaccgg gcgccgtcca      960
ggcacctcga ttagttctcg agcttttgga gtacgtcgtc tttaggttgg ggggagggt      1020
tttatgcgat ggagtttccc cacactgagt gggtggagac tgaagttagg ccagcttggc     1080
acttgatgta attctccttg gaatttgccc ttttttgagtt tggatcttgg ttcattctca    1140
agcctcagac agtggttcaa agttttttc ttccatttca ggtgtcgtga ctcctgggca      1200
gtgtccactc ccaggtccaa ctgcacctcg gttctatcga aaacgcgtcc accatgaccc     1260
ggctgaccgt gctggccctg ctggccggcc tgctggcctc ctcccgggcc ctgcccgccc     1320
aggtggcctt cacccctac gcccccgagc ccggctccac ctgccggctg cgggagtact      1380
acgaccagac cgcccagatg tgctgctcca agtgctcccc cggccagcac gccaaggtgt     1440
tctgcaccaa gacctccgac accgtgtgcg actcctgcga ggactccacc tacacccagc    1500
tgtggaactg ggtgcccgag tgcctgtcct gcggctcccg gtgctcctcc gaccaggtgg    1560
agacccaggc ctgcacccgg gagcagaacc ggatctgcac ctgccggccc ggctggtact    1620
gcgccctgtc caagcaggag ggctgccggc tgtgcgcccc cctgcggaag tgccggcccg    1680
gcttcggcgt ggcccggccc ggcaccgaga cctccgacgt ggtgtgcaag ccctgcgccc    1740
ccggcacctt ctccaacacc acctcctcca ccgacatctg ccggcccac cagatctgca    1800
acgtggtggc catccccggc aacgcctcca tggacgccgt gtgcacctcc acctccccca    1860
cccggtccat ggccccggc gccgtgcacc tgccccagcc cgtgtccacc cggtcccagc    1920
acacccagcc cacccccgag ccctccaccg ccccctccac ctccttcctg ctgcccatgg    1980
gcccctcccc cccgccgag ggctccaccg gcgacgagcc caagtcctgc gacaagaccc     2040
acacctgccc cccctgcccc gccccgagc tgctgggcgg cccctccgtg ttcctgttcc     2100
cccccaagcc caaggacacc ctgatgatct cccggacccc cgaggtgacc tgcgtggtgg    2160
tggacgtgtc ccacgaggac cccgaggtga agttcaactg gtacgtggac ggcgtggagg    2220
tgcacaacgc caagaccaag cccgggag agcagtacaa ctccacctac cgggtggtgt     2280
ccgtgctgac cgtgctgcac caggactggc tgaacggcaa ggagtacaag tgcaaggtgt    2340
ccaacaaggc cctgccgcc ccatcgaga agaccatctc caaggccaag ggccagcccc     2400
gggagcccca ggtgtacacc ctgccccct cccgggagga gatgaccaag aaccaggtgt    2460
ccctgacctg cctggtgaag ggcttctacc cctccgacat cgccgtggag tgggagtcca    2520
acggccagcc cgagaacaac tacaagacca cccccccgt gctggactcc gacggctcct     2580
tcttcctgta ctccaagctg accgtggaca agtcccggtg gcagcaggc aacgtgttct     2640
cctgctccgt gatgcacgag gccctgcaca accactacac ccagaagtcc ctgtccctgt    2700
ccccggcaa gtgatgaggc gcgccgggcg gccgcttccc tttagtgagg gttaatgctt     2760
cgaggatgag tcgacccggg cggccgcttc cctttagtga gggttaatgc ttcgagactc    2820
ctcaggtgca ggctgcctat cagaaggtgg tggctggtgt ggccaatgcc ctggctcaca    2880
aataccactg agatctttttt ccctctgcca aaaattatgg ggacatcatg aagccccttg    2940
agcatctgac ttctggctaa taaaggaaat ttattttcat tgcaatagtg tgttggaatt    3000
ttttgtgtct ctcactcgga aggacatatg ggagggcaaa tcatttaaaa catcagaatg    3060
agtatttggt ttagagtttg gcaacatatg cccatatgct ggctgccatg aacaaaggtt    3120
ggctataaag aggtcatcag tatatgaaac agcccctgc tgtccattcc ttattccata    3180
gaaaagcctt gacttgaggt tagatttttt ttatattttg ttttgtgtta ttttttttctt   3240
taacatccct aaaatttttcc ttacatgttt tactagccag atttttcctc ctctcctgac    3300
```

```
tactcccagt catagctgtc cctcttctct tatggagatc cctcgacaaa tccgataagg    3360
atcgatccgg gctggcgtaa tagcgaagag gcccgcaccg atcgcccttc ccaacagttg    3420
cgcagcctga atggcgaatg gacgcgccct gtagcggcgc attaagcgcg gcgggtgtgg    3480
tggttacgcg cagcgtgacc gctacacttg ccagcgccct agcgcccgct cctttcgctt    3540
tcttcccttc ctttctcgcc acgttcgccg gctttccccg tcaagctcta atcgggggc    3600 tccctttagg gttccgattt agagctttac ggcacctcga ccgcaaaaaa cttgatttgg    3660
gtgatggttc acgtagtggg ccatcgccct gatagacggt ttttcgccct ttgacgttgg    3720
agtccacgtt ctttaatagt ggactcttgt tccaaactgg aacaacactc aaccctatct    3780
cggtctattc ttttgattta agggatttt gccgatttc ggcctattgg ttaaaaaatg    3840
agctgattta caaatattt aacgcgaatt ttaacaaaat attaacgttt acaatttcgc    3900
ctgatgcggt attttctcct tacgcatctg tgcggtattt cacaccgcat acgcggatct    3960
ggtgtggaaa gtccccaggc tccccagcag gcagaagtat gcaaagcatg catctcaatt    4020
agtcagcaac caggtgtgga agtccccag gctccccagc aggcagaagt atgcaaagca    4080
tgcatctcaa ttagtcagca accatagtcc cgccctaac tccgcccatc ccgcccctaa    4140
ctccgcccag ttccgcccat tctccgcccc atggctgact aattttttt atttatgcag    4200 aggccgaggc cgcctcggcc tctgagctat tccagaagta gtgaggaggc ttttttggag    4260
gcctaggctt ttgcaaagat cgatcaagag acaggatgag gatcgtttcg cgctagcgct    4320
accggtcgcc accatgattg aacaagatgg attgcacgca ggttctccgg ccgcttgggt    4380
ggagaggcta ttcggctatg actgggcaca acagacaatc ggctgctctg atgccgccgt    4440
gttccggctg tcagcgcagg ggcgcccggt tctttttgtc aagaccgacc tgtccggtgc    4500
cctgaatgaa ctgcaggacg aggcagcgcg gctatcgtgg ctggccacga cgggcgttcc    4560
ttgcgcagct gtgctcgacg ttgtcactga agcgggaagg gactggctgc tattgggcga    4620
agtgccgggg caggatctcc tgtcatctca ccttgctcct gccgagaaag tatccatcat    4680
ggctgatgca atgcggcggc tgcatacgct tgatccggct acctgcccat tcgaccacca    4740
agcgaaacat cgcatcgagc gagcacgtac tcggatggaa gccggtcttg tcgatcagga    4800
tgatctggac gaagagcatc aggggctcgc gccagccgaa ctgttcgcca ggctcaaggc    4860
gcgcatgccc gacggcgagg atctcgtcgt gacccatggc gatgcctgct tgccgaatat    4920
catggtggaa aatggccgct tttctggatt catcgactgt ggccggctgg gtgtggcgga    4980
ccgctatcag gacatagcgt tggctacccg tgatattgct gaagagcttg gcggcgaatg    5040
ggctgaccgc ttcctcgtgc tttacggtat cgccgctccc gattcgcagc gcatcgcctt    5100
ctatcgcctt cttgacgagt tcttctgaaa gcgggactct ggggttcgaa atgaccgacc    5160
aagcgacgcc caacctgcca tcacgagatt tcgattccac cgccgccttc tatgaaaggt    5220
tgggcttcgg aatcgttttc cgggacgccg gctggatgat cctccagcgc ggggatctca    5280
tgctggagtt cttcgcccac cccaacttgt ttattgcagc ttataatggt tacaaataaa    5340
gcaatagcat cacaaatttc acaaataaag cattttttc actgcattct agttgtggtt    5400
tgtccaaact catcaatgta tcttatcatg tctgaatcga tagcgataag gatccgcgta    5460
tggtgcactc tcggttgccg ccgggcgttt ttattggtg agaatcctca ggttactcat    5520
atatacttta gattgattta aaacttcatt tttaatttaa aaggatctag gtgaagatcc    5580 ttttttgataa tctcatgacc aaaatccctt aacgtgagtt ttcgttccac tgagcgtcag    5640
```

```
accccgtaga aaagatcaaa ggatcttctt gagatccttt ttttctgcgc gtaatctgct      5700
gcttgcaaac aaaaaaacca ccgctaccag cggtggtttg tttgccggat caagagctac      5760
caactctttt tccgaaggta actggcttca gcagagcgca gataccaaat actgtccttc      5820
tagtgtagcc gtagttaggc caccacttca agaactctgt agcaccgcct acatacctcg      5880
ctctgctaat cctgttacca gtggctgctg ccagtggcga taagtcgtgt cttaccgggt      5940
tggactcaag acgatagtta ccggataagg cgcagcggtc gggctgaacg ggggttcgt       6000 gcacacagcc cagcttggag cgaacgacct acaccgaact gagatacta cagcgtgagc       6060 tatgagaaag cgccacgctt cccgaaggga gaaaggcgga caggtatccg gtaagcggca      6120
gggtcggaac aggagagcgc acgagggagc ttccaggggg aaacgcctgg tatctttata      6180
gtcctgtcgg gtttcgccac ctctgacttg agcgtcgatt tttgtgatgc tcgtcagggg      6240
ggcggagcct atggaaaaac gccagcaacg cggccttttt acggttcctg gccttttgct      6300
ggccttttgc tcacatgttc tttcctgcgt tatcccctga ttctgtggat aaccgtatta      6360
ccgccatgca ttagttatta agaccaataa aaaacgcccg cggcaaccg agcgttctga       6420 acaaatccag atggagttct gaggtcatta ctggatctat caacaggagt ccaagcgagc      6480
tcgatatcaa attacgcccc gccctgccac tcatcgcagt actgttgtaa ttcattaagc      6540
attctgccga catggaagcc atcacaaacg gcatgatgaa cctgaatcgc cagcggcatc      6600
agcaccttgt cgccttgcgt ataatatttg cccatggtga aaacggggc gaagaagttg       6660 tccatattgg ccacgtttaa atcaaaactg gtgaaactca cccagggatt ggctgaaacg      6720
aaaaacatat tctcaataaa ccctttaggg aataggcca ggttttcacc gtaacacgcc       6780
acatcttgcg aatatatgtg tagaaactgc cggaaatcgt cgtggtattc actccagagc      6840
gatgaaaacg tttcagtttg ctcatggaaa acggtgtaac aagggtgaac actatcccat      6900
atcaccagct caccgtcttt cattgccata cgaaattccg gatgagcatt catcaggcgg      6960
gcaagaatgt gaataaaggc cggataaaac ttgtgcttat ttttctttac ggtctttaaa      7020
aaggccgtaa tatccagctg aacggtctgg ttataggtac attgagcaac tgactgaaat      7080
gcctcaaaat gttctttacg atgccattgg gatatatcaa cggtggtata ccagtgatt       7140 tttttctcca ttttagcttc cttagctcct gaaaatctcg ataactcaaa aaatacgccc      7200
ggtagtgatc ttatttcatt atggtgaaag ttggaacctc ttacgtgccg atcaacgtct      7260
cattttcgcc aaaagttggc ccagggcttc ccggtatcaa cagggacacc aggatttatt      7320
tattctgcga agtgatcttc cgtcacaggt atttattcgg atttaaattt tcaccgtcat      7380
caccgaaacg cgcgaggcag ctgtgtagtt attaatagta atcaattacg ggtcattag       7440 ttcatagccc atatatggag ttccgcgtta cataacttac ggtaaatggc ccgcctggct      7500
gaccgcccaa cgacccccgc ccattgacgt caataatgac gtatgttccc atagtaacgc      7560
caatagggac tttccattga cgtcaatggg tggagtattt acggtaaact gcccacttgg      7620
cagtacatca agtgtatcat atgccaagta cgccccctat tgacgtcaat gacggtaaat      7680
ggcccgcctg gcattatgcc cagtacatga ccttatggga ctttcctact tggcagtaca      7740
tctacgtatt agtcatcgct attaccatgg tgatgcggtt ttggcagtac atcaatgggc      7800
gtggatagcg gtttgactca cggggatttc caagtctcca ccccattgac gtcaatggga      7860
gtttgttttg gcaccaaaat caacgggact ttccaaaatg tcgtaacaac tccgccccat      7920
tgacgcaaat gggcggtagg cgtgtacggt gggaggtcta tataagcaga gctggtttag      7980
tgaaccgtca gatcaattcg agctcggtac ccccaaactt gacggcaatc ctagcgtgaa      8040
```

```
ggctggtagg attttatccc cgctgccatc atggttcgac cattgaactg catcgtcgcc    8100
gtgtcccaaa atatggggat tggcaagaac ggagaccgac cctggcctcc gctcaggaac    8160
gagttcaagt acttccaaag aatgaccaca acctcttcag tggaaggtaa acagaatctg    8220
gtgattatgg gtaggaaaac ctggttctcc attcctgaga agaatcgacc tttaaaggac    8280
agaattaata tagttctcag tagagaactc aaagaaccac cacgaggagc tcattttctt    8340
gccaaaagtt tggatgatgc cttaagactt attgaacaac cggaattggc aagtaaagta    8400
gacatggttt ggatagtcgg aggcagttct gtttaccagg aagccatgaa tcaaccaggc    8460
cacctcagac tctttgtgac aaggatcatg caggaatttg aaagtgacac gttttttccca   8520 gaaattgatt tggggaaata taaacttctc ccagaatacc caggcgtcct ctctgaggtc    8580
caggaggaaa aaggcatcaa gtataagttt gaagtctacg agaagaaaga ctaacaggaa    8640
gatgctttca agttctctgc tcccctccta aagctatgca ttttttataag accatggggg   8700 atgctcgatc ccctcgcgag ttggttcagc tgctgcctga ggctgacga cctcgcggag    8760 ttctaccggc agtgcaaatc cgtcggcatc caggaaacca gcagcggcta ccgcgcatc    8820 catgcccccg aactgcagga gtggggaggc acgatggccg cttttggtccg gatctttgtg    8880 aaggaacctt acttctgtgg tgtgacataa ttggacaaac tacctacaga gatttaaagc    8940
tctaaggtaa atataaaatt tttaagtgta taatgtgtta aactactgat tctaattgtt    9000
tgtgtatttt agattccaac ctatggaact gatgaatggg agcagtggtg gaatgccttt    9060
aatgaggaaa acctgttttg ctcagaagaa atgccatcta gtgatgatga ggctactgct    9120
gactctcaac attctactcc tccaaaaaag aagagaaagg tagaagaccc caaggacttt    9180
ccttcagaat tgctaagttt tttgagtcat gctgtgttta gtaatagaac tcttgcttgc    9240
tttgctattt acaccacaaa ggaaaaagct gcactgctat acaagaaaat tatggaaaaa    9300
tattctgtaa cctttataag taggcataac agttataatc ataacatact gttttttctt    9360
actccacaca ggcatagagt gtctgctatt aataactatg ctcaaaaatt gtgtaccttt    9420 agcttttaa tttgtaaagg ggttaataag gaatatttga tgtatagtgc cttgactagc    9480
gactgtgcct tctagttgcc agccatctgt tgtttgcccc tccccgtgc cttccttgac     9540 cctggaaggt gccactccca ctgtcctttc ctaataaaat gaggaaattg catcgcattg    9600
tctgagtagg tgtcattcta ttctggggggg tggggtgggg caggacagca aggggggagga  9660 ttgggaagac aatagcaggc atgctgggga tgcggtgggc tctatggag               9709
```

<210> SEQ ID NO 8
<211> LENGTH: 8967
<212> TYPE: DNA
<213> ORGANISM: Artificial Sequence
<220> FEATURE:
<223> OTHER INFORMATION: synthetic vector sequence
<220> FEATURE:
<221> NAME/KEY: CDC
<222> LOCATION: (1120)..(2526)
<223> OTHER INFORMATION: "n" can mean any nucleotide, as long as the
      resulting amino acid sequence is identical to the Etanercept var1
      sequence. For more detils see description of application.
<220> FEATURE:
<221> NAME/KEY: misc_feature
<222> LOCATION: (1120)..(2525)
<223> OTHER INFORMATION: n is a, c, g, or t

<400> SEQUENCE: 8

```
tcaatattgg ccattagcca tattattcat tggttatata gcataaatca atattggcta     60
```

| | |
|---|---|
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg accccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtacg ccccctattg acgtcaatga | 420 |
| cggtaaatgg cccgcctggc attatgccca gtacatgacc ttatgggact ttcctacttg | 480 |
| gcagtacatc tacgtattag tcatcgctat taccatggtg atgcggtttt ggcagtacat | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaacaactc | 660 |
| cgccccattg acgcaaatgg gcggtaggcg tgtacggtgg gaggtctata taagcagagc | 720 |
| tcgtttagtg aaccgtcaga tcgcctggag acgccatcca cgctgttttg acctccatag | 780 |
| aagacaccgg gaccgatcca gcctccgcgg ccgggaacgg tgcattggaa cgcggattcc | 840 |
| ccgtgccaag agtgacgtaa gtaccgccta tagagtctat aggcccaccc ccttggcttc | 900 |
| gttagaacgc ggctacaatt aatacataac cttatgtatc atacacatac gatttaggtg | 960 |
| acactataga ataacatcca ctttgccttt ctctccacag gtgtccactc ccaggtccaa | 1020 |
| ctgcacctcg gttctatcga aaacgcgtcc accatggccc ccgtggccgt gtgggctgcc | 1080 |
| ctggccgtgg gcctggaact gtgggccgct gcccacgccn nnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |

```
nnnnnnnnnn nnnnnnnnnn nnnnnnnnnn nnnnnnnnnn nnnnnnnnnn nnnnnnnnnn    2520
nnnnnaggcg cgccgggcgg ccgcttccct ttagtgaggg ttaatgcttc gagcagacat    2580
gataagatac attgatgagt ttggacaaac cacaactaga atgcagtgaa aaaaatgctt    2640
tatttgtgaa atttgtgatg ctattgcttt atttgtaacc attataagct gcaataaaca    2700
agttaacaac aacaattgca ttcattttat gtttcaggtt caggggggaga tgtgggaggt    2760 ttttttaaagc aagtaaaacc tctacaaatg tggtaaaatc cgataaggat cgatccgggc    2820
tggcgtaata gcgaagaggc ccgcaccgat cgcccttccc aacagttgcg cagcctgaat    2880
ggcgaatgga cgcgccctgt agcggcgcat taagcgcggc gggtgtggtg gttacgcgca    2940
gcgtgaccgc tacacttgcc agcgccctag cgcccgctcc tttcgctttc ttcccttcct    3000
ttctcgccac gttcgccggc tttccccgtc aagctctaaa tcgggggctc cctttagggt    3060
tccgatttag agctttacgg cacctcgacc gcaaaaaact tgatttgggt gatggttcac    3120
gtagtgggcc atcgccctga tagacggttt ttcgcccttt gacgttggag tccacgttct    3180
ttaatagtgg actcttgttc caaactggaa caacactcaa ccctatctcg gtctattctt    3240
ttgatttata agggattttg ccgatttcgg cctattggtt aaaaaatgag ctgatttaac    3300
aaatatttaa cgcgaatttt aacaaaatat taacgtttac aatttcgcct gatgcggtat    3360
tttctcctta cgcatctgtg cggtatttca caccgcatac gcggatctgc gcagcaccat    3420
ggcctgaaat aacctctgaa agaggaactt ggttaggtac cttctgaggc ggaaagaacc    3480
agctgtggaa tgtgtgtcag ttagggtgtg aaagtccccc aggctcccca gcaggcagaa    3540
gtatgcaaag catgcatctc aattagtcag caaccaggtg tggaaagtcc ccaggctccc    3600
cagcaggcag aagtatgcaa agcatgcatc tcaattagtc agcaaccata gtcccgcccc    3660
taactccgcc catcccgccc ctaactccgc ccagttccgc ccattctccg ccccatggct    3720
gactaatttt ttttatttat gcagaggccg aggccgcctc ggcctctgag ctattccaga    3780
agtagtgagg aggcttttttt ggaggcctag gcttttgcaa aaagcttgat tcttctgaca    3840
caacagtctc gaacttaagg ctagagccac catgattgaa caagatggat tgcacgcagg    3900
ttctccggcc gcttgggtgg agaggctatt cggctatgac tgggcacaac agacaatcgg    3960
ctgctctgat gccgccgtgt tccggctgtc agcgcagggg cgcccggttc ttttttgtcaa    4020 gaccgacctg tccggtgccc tgaatgaact gcaggacgag gcagcgcggc tatcgtggct    4080
ggccacgacg ggcgttcctt gcgcagctgt gctcgacgtt gtcactgaag cgggaaggga    4140
ctggctgcta ttgggcgaag tgccggggca ggatctcctg tcatctcacc ttgctcctgc    4200
cgagaaagta tccatcatgg ctgatgcaat gcggcggctg catacgcttg atccggctac    4260
ctgcccattc gaccaccaag cgaaacatcg catcgagcga gcacgtactc ggatggaagc    4320
cggtcttgtc gatcaggatg atctggacga agagcatcag gggctcgcgc cagccgaact    4380
gttcgccagg ctcaaggcgc gcatgcccga cggcgaggat ctcgtcgtga cccatggcga    4440
tgcctgcttg ccgaatatca tggtggaaaa tggccgcttt tctggattca tcgactgtgg    4500
ccggctgggt gtggcggacc gctatcagga catagcgttg gctacccgtg atattgctga    4560
agagcttggc ggcgaatggg ctgaccgctt cctcgtgctt tacggtatcg ccgctcccga    4620
ttcgcagcgc atcgccttct atcgccttct tgacgagttc ttctgagcgg gactctgggg    4680
ttcgaaatga ccgaccaagc gacgcccaac ctgccatcac gatggccgca ataaaatatc    4740 tttatttttca ttacatctgt gtgttggttt tttgtgtgaa tcgatagcga taaggatccg    4800
```

```
cgtatggtgc actctcagta caatctgctc tgatgccgca tagttaagcc agccccgaca    4860
cccgccaaca cccgctgacg cgccctgacg ggcttgtctg ctcccggcat ccgcttacag    4920
acaagctgtg accgtctccg ggagctgcat gtgtcagagg ttttcaccgt catcaccgaa    4980
acgcgcgaga cgaaagggcc tcgtgatacg cctattttta taggttaatg tcatgataat    5040
aatggtttct tagacgtcag gtggcacttt tcggggaaat gtgcgcggaa ccctatttg    5100
tttattttc taaatacatt caaatatgta tccgctcatg agacaataac cctgataaat    5160
gcttcaataa tattgaaaaa ggaagagtat gagtattcaa catttccgtg tcgcccttat    5220
tcccttttt gcggcatttt gccttcctgt ttttgctcac cagaaacgc tggtgaaagt    5280
aaaagatgct gaagatcagt tgggtgcacg agtgggttac atcgaactgg atctcaacag    5340
cggtaagatc cttgagagtt ttcgccccga agaacgtttt ccaatgatga gcacttttaa    5400
agttctgcta tgtggcgcgg tattatcccg tattgacgcc gggcaagagc aactcggtcg    5460
ccgcatacac tattctcaga atgacttggt tgagtactca ccagtcacag aaaagcatct    5520
tacggatggc atgacagtaa gagaattatg cagtgctgcc ataaccatga gtgataacac    5580
tgcggccaac ttacttctga caacgatcgg aggaccgaag gagctaaccg cttttttgca    5640
caacatgggg gatcatgtaa ctcgccttga tcgttgggaa ccggagctga atgaagccat    5700
accaaacgac gagcgtgaca ccacgatgcc tgtagcaatg gcaacaacgt tgcgcaaact    5760
attaactggc gaactactta ctctagcttc ccggcaacaa ttaatagact ggatggaggc    5820
ggataaagtt gcaggaccac ttctgcgctc ggcccttccg gctggctggt ttattgctga    5880
taaatctgga gccggtgagc gtgggtctcg cggtatcatt gcagcactgg ggccagatgg    5940
taagccctcc cgtatcgtag ttatctacac gacggggagt caggcaacta tggatgaacg    6000
aaatagacag atcgctgaga taggtgcctc actgattaag cattggtaac tgtcagacca    6060
agtttactca tatatacttt agattgattt aaaacttcat ttttaattta aaaggatcta    6120
ggtgaagatc cttttttgata atctcatgac caaaatccct taacgtgagt tttcgttcca    6180
ctgagcgtca gaccccgtag aaaagatcaa aggatcttct tgagatcctt ttttctgcg    6240
cgtaatctgc tgcttgcaaa caaaaaaacc accgctacca gcggtggttt gtttgccgga    6300
tcaagagcta ccaactcttt ttccgaaggt aactggcttc agcagagcgc agataccaaa    6360
tactgtcctt ctagtgtagc cgtagttagg ccaccacttc aagaactctg tagcaccgcc    6420
tacatacctc gctctgctaa tcctgttacc agtggctgct gccagtggcg ataagtcgtg    6480
tcttaccggg ttggactcaa gacgatagtt accggataag cgcagcggt cgggctgaac    6540
ggggggttcg tgcacacagc ccagcttgga gcgaacgacc tacaccgaac tgagatacct    6600
acagcgtgag ctatgagaaa gcgccacgct cccgaaggg agaaaggcgg acaggtatcc    6660
ggtaagcggc agggtcggaa caggagagcg cacgagggag cttccagggg gaaacgcctg    6720
gtatctttat agtcctgtcg ggtttcgcca cctctgactt gagcgtcgat ttttgtgatg    6780
ctcgtcaggg gggcggagcc tatggaaaaa cgccagcaac gcggcctttt tacggttcct    6840
ggccttttgc tggccttttg ctcacatggc tcgacagatc catttaaatt ttcaccgtca    6900
tcaccgaaac gcgcgaggca gctgtggaat gtgtgtcagt tagggtgtgg aaagtcccca    6960
ggctccccag caggcagaag tatgcaaagc atgcatctca attagtcagc aaccaggtgt    7020
ggaaagtccc caggctcccc agcaggcaga agtatgcaaa gcatgcatct caattagtca    7080
gcaaccatag tcccgcccct aactccgccc atcccgcccc taactccgcc cagttccgcc    7140
cattctccgc cccatggctg actaattttt tttatttatg cagaggccga ggccgcctcg    7200
```

```
gcctctgagc tattccagaa gtagtgagga ggcttttttg gaggcctagg cttttgcaaa    7260
aagctaattc gagctcggta cccccaaact tgacggcaat cctagcgtga aggctggtag    7320
gattttatcc ccgctgccat catggttcga ccattgaact gcatcgtcgc cgtgtcccaa    7380
aatatgggga ttggcaagaa cggagaccga ccctggcctc cgctcaggaa cgagttcaag    7440
tacttccaaa gaatgaccac aacctcttca gtggaaggta acagaatctg gtgattatg    7500 ggtaggaaaa cctggttctc cattcctgag aagaatcgac ctttaaagga cagaattaat    7560
atagttctca gtagagaact caaagaacca ccacgaggag ctcattttct tgccaaaagt    7620
ttggatgatg ccttaagact tattgaacaa ccggaattgg caagtaaagt agacatggtt    7680
tggatagtcg gaggcagttc tgtttaccag gaagccatga atcaaccagg ccacctcaga    7740
ctctttgtga caaggatcat gcaggaattt gaaagtgaca cgttttttccc agaaaattgat    7800 ttggggaaat ataaacttct cccagaatac ccaggcgtcc tctctgaggt ccaggaggaa    7860
aaaggcatca agtataagtt tgaagtctac gagaagaaag actaacagga agatgctttc    7920
aagttctctg ctcccctcct aaagctatgc atttttataa gaccatgggg gatgctcgat    7980
cccctcgcga gttggttcag ctgctgcctg aggctggacg acctcgcgga gttctaccgg    8040
cagtgcaaat ccgtcggcat ccaggaaacc agcagcggct atccgcgcat ccatgccccc    8100
gaactgcagg agtggggagg cacgatggcc gctttggtcc gagatctttg tgaaggaacc    8160
ttacttctgt ggtgtgacat aattggacaa actacctaca gagatttaaa gctctaaggt    8220
aaatataaaa ttttttaagtg tataatgtgt taaactactg attctaattg tttgtgtatt    8280
ttagattcca acctatggaa ctgatgaatg ggagcagtgg tggaatgcct ttaatgagga    8340
aaacctgttt tgctcagaag aaatgccatc tagtgatgat gaggctactg ctgactctca    8400
acattctact cctccaaaaa agaagagaaa ggtagaagac cccaaggact tccttcaga    8460 attgctaagt ttttttgagtc atgctgtgtt tagtaataga actcttgctt gctttgctat    8520
ttacaccaca aaggaaaaag ctgcactgct atacaagaaa attatggaaa aatattctgt    8580
aacctttata agtaggcata acagttataa tcataacata ctgttttttc ttactccaca    8640
caggcataga gtgtctgcta ttaataacta tgctcaaaaa ttgtgtacct ttagcttttt    8700
aatttgtaaa ggggttaata aggaatattt gatgtatagt gccttgacta gagatcataa    8760
tcagccatac cacatttgta gaggttttac ttgctttaaa aaacctccca cacctccccc    8820
tgaacctgaa acataaaatg aatgcaattg ttgttgttaa cttgtttatt gcagcttata    8880
atggttacaa ataaagcaat agcatcacaa atttcacaaa taaagcattt tttcactgca    8940
ttctagttgt ggtttgaatt cggatct                                      8967
```

<210> SEQ ID NO 9
<211> LENGTH: 10
<212> TYPE: PRT
<213> ORGANISM: Artificial Sequence
<220> FEATURE:
<223> OTHER INFORMATION: synthetic peptide sequence Pep1

<400> SEQUENCE: 9

Arg Ser Leu Leu Ser Leu Arg Ser Ser Leu
1               5                   10

<210> SEQ ID NO 10
<211> LENGTH: 10
<212> TYPE: PRT
<213> ORGANISM: Artificial Sequence

```
-continued

<220> FEATURE:
<223> OTHER INFORMATION: synthetic peptide sequence Pep2

<400> SEQUENCE: 10

Met His Val Ala Trp Asn Asp Met Cys Pro
1               5                   10
```